(12) United States Patent
Koepf et al.

(10) Patent No.: US 9,206,410 B2
(45) Date of Patent: *Dec. 8, 2015

(54) COMPOSITIONS, METHODS AND KITS FOR PREPARING PLASMINOGEN AND PLASMIN PREPARED THEREFROM

(75) Inventors: Edward Koepf, Holly Springs, NC (US); Myles Lindsay, Garner, NC (US); Rebecca Silverstein, Cary, NC (US); Jennifer Hunt, Raleigh, NC (US); James Rebbeor, Garner, NC (US); Thomas Zimmerman, Raleigh, NC (US); Charles Miller, Apex, NC (US); Anthony Caronna, Cary, NC (US); Kenya Stokes, Cary, NC (US)

(73) Assignee: GRIFOLS THERAPEUTICS INC., Research Triangle Park, NC (US)

( * ) Notice: Subject to any disclaimer, the term of this patent is extended or adjusted under 35 U.S.C. 154(b) by 292 days.

This patent is subject to a terminal disclaimer.

(21) Appl. No.: 13/147,491

(22) PCT Filed: Mar. 2, 2010

(86) PCT No.: PCT/US2010/025898
§ 371 (c)(1), (2), (4) Date: Sep. 23, 2011

(87) PCT Pub. No.: WO2010/101903
PCT Pub. Date: Sep. 10, 2010

(65) Prior Publication Data
US 2012/0009650 A1     Jan. 12, 2012

Related U.S. Application Data

(60) Provisional application No. 61/156,990, filed on Mar. 3, 2009.

(51) Int. Cl.
C12N 9/68   (2006.01)
C07K 1/18   (2006.01)

(52) U.S. Cl.
CPC ....... *C12N 9/6435* (2013.01); *C12Y 304/21007* (2013.01)

(58) Field of Classification Search
None
See application file for complete search history.

(56) References Cited

U.S. PATENT DOCUMENTS

| 2,677,642 A | 5/1954 | Frank et al. |
| 2,677,643 A | 5/1954 | Frank et al. |

(Continued)

FOREIGN PATENT DOCUMENTS

| CA | 2045869 | 12/1991 |
| EP | 0 009 879 A1 | 4/1980 |

(Continued)

OTHER PUBLICATIONS

2003 Amersham Biosciences Sepharose Fast Flow ion exchangers: 5 pages total.*

(Continued)

*Primary Examiner* — Marsha Tsay
(74) *Attorney, Agent, or Firm* — Carl B. Massey, Jr.; Womble Carlyle Sandridge & Rice

(57) ABSTRACT

Compositions and methods for preparing plasminogen, in particular recombinant plasminogen, and compositions and methods of utilizing same for preparing plasmin are provided.

10 Claims, 9 Drawing Sheets

```
  1  MetArgAspValValLeuPheGluLysLysValTyrLeuSerGluCysLysThrGlyAsn
 21  GlyLysAsnTyrArgGlyThrMetSerLysThrLysAsnGlyIleThrCysGlnLysTrp
 41  SerSerThrSerProHisArgProArgPheSerProAlaThrHisProSerGluGlyLeu
 61  GluGluAsnTyrCysArgAsnProAspAsnAspProGlnGlyProTrpCysTyrThrThr
 81  AspProGluLysArgTyrAspTyrCysAspValProGlnCysAlaAlaProSerPheAsp
101  CysGlyLysProGlnValGluProLysLysCysProGlyArgValValGlyGlyCysVal
121  AlaHisProHisSerTrpProTrpGlnValSerLeuArgThrArgPheGlyMetHisPhe
141  CysGlyGlyThrLeuIleSerProGluTrpValLeuThrAlaAlaHisCysLeuGluLys
161  SerProArgProSerSerTyrLysValIleLeuGlyAlaHisGlnGluValAsnLeuGlu
181  ProHisValGlnGluIleGluValSerArgLeuPheLeuGluProThrArgLysAspIle
201  AlaLeuLeuLysLeuSerSerProAlaValIleThrAspLysValIleProAlaCysLeu
221  ProSerProAsnTyrValValAlaAspArgThrGluCysPheIleThrGlyTrpGlyGlu
241  ThrGlnGlyThrPheGlyAlaGlyLeuLeuLysGluAlaGlnLeuProValIleGluAsn
261  LysValCysAsnArgTyrGluPheLeuAsnGlyArgValGlnSerThrGluLeuCysAla
281  GlyHisLeuAlaGlyGlyThrAspSerCysGlnGlyAspSerGlyGlyProLeuValCys
301  PheGluLysAspLysTyrIleLeuGlnGlyValThrSerTrpGlyLeuGlyCysAlaArg
321  ProAsnLysProGlyValTyrValArgValSerArgPheValThrTrpIleGluGlyVal
341  MetArgAsnAsn (SEQ ID NO:1)
```

(56) References Cited

U.S. PATENT DOCUMENTS

| | | | |
|---|---|---|---|
| 2,691,620 A | 10/1954 | Frank et al. |
| 2,701,227 A | 2/1955 | Frank et al. |
| 2,784,145 A | 3/1957 | Frank et al. |
| 3,136,703 A | 6/1964 | Singher |
| 3,226,304 A | 12/1965 | Siiteri et al. |
| 3,255,094 A | 6/1966 | Mather et al. |
| 3,419,472 A | 12/1968 | Siiteri et al. |
| 3,434,929 A | 3/1969 | Buck et al. |
| 3,444,045 A | 5/1969 | Derenzo et al. |
| 3,639,213 A | 2/1972 | Ginger et al. |
| 3,865,692 A | 2/1975 | Holleman et al. |
| 3,950,223 A | 4/1976 | Yugari et al. |
| 3,950,513 A | 4/1976 | Jensen |
| 3,980,772 A | 9/1976 | Ginger et al. |
| 4,082,612 A | 4/1978 | Robbins et al. |
| 4,115,551 A | 9/1978 | Lormeau et al. |
| 4,177,262 A | 12/1979 | Lormeau et al. |
| 4,259,448 A | 3/1981 | Nakamura et al. |
| 4,305,926 A | 12/1981 | Everse et al. |
| 4,361,652 A | 11/1982 | Uemura et al. |
| 4,361,653 A | 11/1982 | Watanabe et al. |
| 4,381,346 A | 4/1983 | Huasin et al. |
| 4,418,052 A | 11/1983 | Wong |
| 4,442,213 A | 4/1984 | Heber et al. |
| 4,446,316 A | 5/1984 | Chazov et al. |
| 4,462,980 A | 7/1984 | Diedrichsen et al. |
| 4,499,073 A | 2/1985 | Tenold |
| 4,551,271 A | 11/1985 | Hochuli et al. |
| RE32,271 E | 10/1986 | Husain et al. |
| 4,631,211 A | 12/1986 | Houghten et al. |
| 4,652,639 A | 3/1987 | Stabinsky |
| 4,663,146 A | 5/1987 | Morser et al. |
| 4,774,087 A | 9/1988 | Wu et al. |
| 4,877,830 A | 10/1989 | Dobeli et al. |
| 4,908,204 A | 3/1990 | Robinson et al. |
| 5,024,829 A | 6/1991 | Berger et al. |
| 5,068,106 A | 11/1991 | Paques et al. |
| 5,096,637 A | 3/1992 | DiLeo et al. |
| 5,112,609 A | 5/1992 | Johnston et al. |
| 5,149,533 A | 9/1992 | Mulvihill et al. |
| 5,165,912 A | 11/1992 | Selmer et al. |
| 5,237,050 A | 8/1993 | Boyle et al. |
| 5,242,828 A | 9/1993 | Bergstrom et al. |
| 5,288,489 A | 2/1994 | Reich et al. |
| 5,290,692 A | 3/1994 | Suzuki et al. |
| 5,304,383 A | 4/1994 | Eibl et al. |
| 5,328,996 A | 7/1994 | Boyle |
| 5,334,384 A | 8/1994 | Mannix et al. |
| 5,371,007 A | 12/1994 | Linnau et al. |
| 5,407,673 A | 4/1995 | Reich et al. |
| 5,407,678 A | 4/1995 | Rose et al. |
| 5,472,692 A | 12/1995 | Liu et al. |
| 5,587,291 A | 12/1996 | Binder |
| 5,629,213 A | 5/1997 | Kornguth et al. |
| 5,728,674 A | 3/1998 | Sprecher et al. |
| 5,767,269 A | 6/1998 | Hirsh et al. |
| 5,776,452 A | 7/1998 | Eibl et al. |
| 5,854,049 A | 12/1998 | Reed et al. |
| 5,868,720 A | 2/1999 | Van Antwerp et al. |
| 5,876,999 A | 3/1999 | Wu et al. |
| 5,879,923 A | 3/1999 | Yago et al. |
| 5,928,218 A | 7/1999 | Gelbfish |
| 6,139,819 A | 10/2000 | Unger et al. |
| 6,183,692 B1 | 2/2001 | Trese et al. |
| 6,207,066 B1 | 3/2001 | Trese et al. |
| 6,218,517 B1 | 4/2001 | Suzuki |
| 6,270,672 B1 | 8/2001 | Turecek et al. |
| 6,309,873 B1 | 10/2001 | Torrens Madrazo et al. |
| 6,312,893 B1 | 11/2001 | Van Ness et al. |
| 6,355,243 B1 | 3/2002 | Novokhatny et al. |
| 6,406,921 B1 | 6/2002 | Wagner et al. |
| 6,413,759 B1 | 7/2002 | Madrazo et al. |
| 6,444,422 B2 | 9/2002 | Ness et al. |
| 6,479,253 B1 | 11/2002 | Silver et al. |
| 6,538,103 B1 | 3/2003 | Ji et al. |
| 6,613,508 B1 | 9/2003 | Ness et al. |
| 6,623,928 B2 | 9/2003 | Van Ness et al. |
| 6,664,112 B2 | 12/2003 | Mulligan et al. |
| 6,694,764 B1 | 2/2004 | Eckstein, Jr. et al. |
| 6,946,438 B1 | 9/2005 | Nagai et al. |
| 6,964,764 B2 | 11/2005 | Zimmerman et al. |
| 6,969,515 B2 | 11/2005 | Jesmok et al. |
| 7,105,327 B1 | 9/2006 | Kuppusamy et al. |
| 7,253,264 B1 | 8/2007 | Lauffler et al. |
| 7,547,435 B2 | 6/2009 | Pakola et al. |
| 7,776,026 B2 | 8/2010 | Trese et al. |
| 8,101,394 B2 * | 1/2012 | Novokhatny ............ 435/219 |
| 8,182,808 B2 * | 5/2012 | Novokhatny ............ 424/94.64 |
| 8,268,782 B2 * | 9/2012 | Rebbeor et al. ............ 514/14.2 |
| 8,512,980 B2 * | 8/2013 | Novokhatny ............ 435/68.1 |
| 2002/0192794 A1 | 12/2002 | Dadd et al. |
| 2003/0012778 A1 | 1/2003 | Zimmerman |
| 2004/0171103 A1 * | 9/2004 | Bradley et al. ............ 435/68.1 |
| 2005/0124036 A1 | 6/2005 | Susilo |
| 2009/0275513 A1 * | 11/2009 | Rebbeor et al. ............ 514/12 |
| 2010/0144622 A1 * | 6/2010 | Lin et al. ............ 514/12 |

FOREIGN PATENT DOCUMENTS

| | | |
|---|---|---|
| EP | 0 256 836 | 2/1988 |
| EP | 0 399 321 A2 | 11/1990 |
| EP | 0397 366 A1 | 11/1990 |
| GB | 904478 A | 8/1962 |
| GB | 985498 A | 3/1965 |
| GB | 2 090 599 A | 7/1982 |
| WO | WO 87/06836 A | 11/1987 |
| WO | WO 93/15189 A | 8/1993 |
| WO | WO 94/23668 A1 | 10/1994 |
| WO | WO 95/04077 | 2/1995 |
| WO | WO 95/20416 A1 | 8/1995 |
| WO | WO 96/38726 A1 | 12/1996 |
| WO | WO 97/15572 | 5/1997 |
| WO | WO 97/27331 A2 | 7/1997 |
| WO | WO 98/37086 | 8/1998 |
| WO | WO 99/05322 | 2/1999 |
| WO | WO 01/81365 A2 | 11/2001 |
| WO | WO 02/50290 | 6/2002 |
| WO | WO 03/054232 A2 | 7/2003 |
| WO | WO 2004/052228 A2 | 6/2004 |
| WO | WO 2005/105990 A2 | 11/2005 |
| WO | WO 2007/047874 A2 | 4/2007 |
| WO | WO 2009/073471 | 6/2009 |

OTHER PUBLICATIONS

Quigley, J.P., et al. 1974 The Journal of Biological Chemistry 249(13): 4306-4311.*

Abe, et al., "Immobilized urokinase column as part of a specific detection system for plasminogen species separated by high-performance affinity chromatography," J. Chromatography, (1991), vol. 565, pp. 183-195.

Abe, T., "Fibrinolytic Influence of monocarbonic acids and some other substances," Proc. Intern. Cong. Hematol., (1962), vol. 3; pp. 1587-1639.

Alkjaersig, N., et aL, "The Activation of Human Plasminogen," J. Biol. Chem., 233(1): 81-85 1958.

Alkjaersig, N., et al, "The Mechanism of Clot Dissolution by Plasmin," J. Clin. Invest., 38(7): 1086-1095 1959.

Ambrus, C., et al., "Insolubilized Activators of the Fibrinolysin System," J. Med. 3:270-281 (1972).

Ambrus, J.L., et al., "Clinical Pharmacology of various types of fibrinolytic enzyme preparations," Am. J. Cardio!., 6:462-475 (1960).

Amor, M. et al , "Thrombectomy with the hydrolysing catheter," Archives des Maladies du Couer et des Vaisseaux, (1997), vol. 90, No. 6,. 797-804.

Amris, C.J., et aL, "Effect of Plasmin Therapy on Blood Coagulation and on Plasma Proteins in Patients with Cancer," Danish Medical Bulletin, 11(5):141-145 (1964).

Amris, C.J., et al., "Infusion of porcine plasmin in man," Scandivay. J. Clin. & Lab. Investigation, (1963), vol. 15, pp. 179-188.

(56) References Cited

OTHER PUBLICATIONS

Amris, C.J., et al., "Turnover and Distribution of ¹¹-Labelled Procine Plasmin in Man and Dog," Danish Medical Bulletin, 11(5):146-152 (1964).
Amris, et al., "Clinical studies on an activator free porcine plasma (plasmin-novo)," SANGRE 9 (BARC), (1964), vol. 61, pp. 12-18.
Andrianov, S.I., et al., "Peculiarities of Hydrolytic Action of Plasmin, Miniplasmin, Microplasmin and Trypsin on Polymeric Fibrin," *Ukr. Biokhim. Zh.*, 64(3): 14-20 (1992).
Anlyan, W., et al., "Experiences with Fibrinolysin in Peripheral Vascular Occlusive Disease," *Am. J. Cardiol.*, 6:507-512 (1960).
Anonick, P., of al., "Regulation of Plasmin, Miniplasmin and Streptokinase—Plasmin Complex by—a-2-Antiplasmin, a-2-Macroglobulin, and Antithrombin III in the Presence of Heparin," *Thrombosis Res.*, 59: 449-462 (1990).
Ambrus, et al., "Clinical and experimental studies on fibrinolytic enzymes," Ann NY Acad Sci., (Aug. 30, 1957), vol. 68, No. 1, p.s. 97-137.
Aronen, H.J, et al., "99mTc-plasmin test in deep vein thrombosis of the leg," Eur J Nucl Med, 10:10-12 (1985).
Barrett, A.J., et al., "The Electrophoretically 'Slow' and 'Fast' Forms of the a2-Macroglobulin Molecule," *Biochem. J.*, 181:401-418 (1979).
Barth, K.H. et al., "Multicenter prospective randomized comparison between a mechanical thrombectomy systems (OASIS) and pule-spray thrombolysis for thrombosed hemodialysis grafts," Radiology, (Nov. 1998) vol. 209P, Supp. [S]: 714.
Beathard, G. A., "Mechanical versus pharmacomechanical thrombolysis for the treatment of thrombosed dialysis access grafts," Kidney International, (1994), vol. 45, pp. 1401-1406.
Becker, Gary J., Local Thrombolytic Therapy: Bridging the 'Generation Gap,' *Am. J. RoentgenoL*, 140(2): 403-405 (1983).
Bennett, D., et al., "Kinetic Characterization of the Interaction of Biotinylated Human Interleukin 5 with an Fc Chimera of its Receptor a Subunit and Development of an ELISA Screening Assay using Real-Time Interaction Biosensor Analysis," *I Molecular Recognition*, 8: 52-58 (1995).
Bhisitkul, R.B., "Anticipation for enzymatic vitreolysis," *Br. J. OphthalmoL*, 85: 1-3 (2001).
Binder, B.R., et al., "Purification and Characterization of Human Vascular Plasminogen Activator Derived from Blood Vessel Perfusates," *Journal of Biological Chemistry*, 254(6):1998-2003 (1979).
Bookstein, J.J., et al., How I Do It: Pulse-spray pharmacomechanical thrombolysis, Cardiovasc. Intervent Radiol., (1992) vol. 15, pp. 228-233.
Boucek, R., et al., "Segmental Perfusion of the Coronary Arteries with Fibrinolysin in Man Following a Myocardial Infarction," *Am. J. Cardiol.*, 6:525-533 (1960).
Bowie, J.U., et al., "Deciphering the Message in Protein Sequences: Tolerance to Amino Acid Substitutions," *Science*, 247: 1306-1310 (1990).
Boyles, P.W., et al., "Comparative effectiveness of intravenous and intra-arterial fibrinolysin therapy," *Am. J. Cardio!.*, 6:439-446 (1960).
Browse, N., "Deep Vein Thrombosis," British Medical Journal, 4:676-678 (1969).
Burck, P.J., et al., "Characterization of a Modified Human Tissue Plasminogen Activator Comprising a Kringle-2 and a Protease Domain,"*J Biol. Chem.*, 265(9): 5170-5177 (1990).
Burgin, J. and J. Shaller, "Expression, Isolation acid Characterization of a Mutated Human Plasminogen Kringle 3 with a Functional Lysine Binding Site," *Cell. Mol. Life. Sci.* 55: 135-141 (1999).
Burnouf-Radosevich et al., "Nanofiltration, A New Specific Virus Elimination Method Applied to High-Purity Factor IX and Factor XI Concentrates," Vox Sang 67(2): 132-8 (1994) (abstract only).
Caballero, AR., et al., "Cloning, Expression, Sequence Analysis and Characterization of Streptokinases Secreted by Porcine and Equine isolates of *Streptococcus equisimilis,*" *Infection and Immunity*, 67(12) :6478-6486 (1999).

Cao, Y., et al., "Kringle Domains of Human Angiostatin," *J. Biol. Chem.*, 271(46): 29461-29467 (1996).
Castellino, F.J. and J.R. Powell, "Human Plasminogen," *Meth. Enzymology* 80:365-378 (1981).
Castellino, F.J., and S.G. McCance, "The kringle domains of human plasminogen," *Ciba Found. Symp.*, 212: 46-65 (1997).
Castellino, F.J., et al., "Rabbit Plasminogen and Plasmin Isozymes," *Methods in Enzymology*, 45:273-286 (1976).
Chang, Y., et al., "Structure and Ligand Binding Determinants of the Recombinant Kringle 5 Domain of Human Plasminogen," *Biochemistry*, 37: 3258-3271 (1998).
Chase, T. and E. Shaw, "Titration of Trypsin, Plasmin, and Thrombin with p-Nitrophenyl 0-Guanidinobenzoate HCI," *Methods EnzymoL*, 19: 20-27 (1970).
Christensen et al., Stopped-flow fluorescence kinetics of bovine α2-antiplasmin inhibition of bovine midiplasmin, Biochem. J. 305:97-102 (1995).
Cload, S.T., et al., "Development of Improved tRNAs for in vitro biosynthesis of proteins containing unnatural amino acids," *Chem. Biol.*, 3: 1033-1038 (1996).
Collen D., et al., "On the Regulation and Control of Fibrinolysis," *Throm. Haemost.*, 43: 77-89 (1980).
Collen D., et al., "Thrombolysis with human extrinsic (tissue-type) plasminogen activator in rabbits with experimental jugular vein thrombosis. Effect of molecular form and dose of activator, age of the thrombus, and route of administration," *J. of Clin. Invest.*, 71(2):368-376 (1983).
Cunningham, B.C., and J.A. Wells, "High-Resolution Epitope Mapping of hGH-Receptor Interactions by Alanine-Scanning Mutagenesis," *Science*, 244: 1081-1085 (1989).
Dahl, 0.E., et al., "99mTc-Plasmin Uptake Test is Unreliable for Diagnosing Asymptomatic Deep Vein Thrombosis After Hip Replacement Surgery," Thrombosis Research, 62:781-784 (1991).
De Renzo, E.C., et al., "Preparation and Certain Properties of Highly Purified Streptokinase," *J. Biol. Chem.* 242(3): 533-542 (1967).
de Vos, A.M., et al., "Human Growth Hormone and Extracellular Domain of Its Receptor: Crystal Structure of the Complex," *Science*, 255: 306-312 (1992).
Deacon, et al., "Technetium 99m-plasmin: a new test for the detection of deep vein thrombosis," Eur J. Nucl. Med., (1980), vol. 53, No. 631, pp. 673-677.
Decision of the Board of Patent Appeals and Interferences dated Feb. 19, 2008 in Appeal No. 2007-0545, Ex parte Thomas P. Zimmerman, Valery Novokhatny, Shang Jiang and James' Colancleve (with claims considered on Appeal).
Deutsch, D.G. and E.T. Mertz, "Plasminogen: purification from human plasma by affinity chromatography," *Science* 170:1095-1096 (1970).
Douglas, J.T., et al., "The Two-Domain NK1 Fragment of Plasminogen: Flding, Ligand Binding, and Thermal Stability Profile,"*Biochemistry*, 41(10): 3302-3310 (2002).
Dupe, F et al., "Acyl-enzymes as thrombolytic agents in dog models of venous thrombosis and pulmonary embolism," Thrombosis and Haemostasis, (1981), vol. 51, No. 2, pp. 248-253.
Edenbrandt, C.M., et al., "Comparison between 99Tcm-porcine plasmin and 99Tcm-labelled erythrocytes in diagnosis of deep vein thrombosis," Clinical Physiology 4:243-252 (1984).
Edenbrandt, C.M., et al., "Diagnosis of Deep Venous Thrombosis by 99mTc-Human Serum Albumin Microcolloid," Eur J Nucl Med 8:332-334 (1983).
Edenbrandt, C.M., et al., "Follow-up of circulatory changes secondary to deep venous thrombosis with special regards to radionuclide tests," Clinical Physiology 6:153-161 (1986).
Edenbrandt, C.M., et al., "Return to normal of 99mTc-plasmin test after deep venous thrombosis and its relationship to vessel wall fibrinolysis," Eur J Nucl Med 12:197-200 (1986).
Einarsson, M., et al., "Characterization of Highly Purified Native Streptokinase and Altered Streptokinase After Alkaline Treatment," *Biochim. Biophys. Acta* 568:19-29 (1979).
Ellman, J., et al., "Biosynthetic Method for Introducing Unnatural Amino Acids Site-Specifically into Proteins," *Methods Enzym.*, 202: 301-336 (1991).

(56) References Cited

OTHER PUBLICATIONS

European Supplementary Partial Search Report (EP 00 97 8572, dated Jul. 16, 2004).
European Supplementary Partial Search Report (EP 00 99 0910, dated May 25, 2004).
European Supplementary Partial Search Report (EP 00 99 1956, dated Jun. 1, 2004).
Extended European Search Report (EP 1 956 082 AI, dated Jul. 10, 2008).
Freitag, H., et al., "Lys-plasminogen as an Adjunct to Local Intra-arterial Fibrinolysis of Carotid Territory Stroke: Laboratory and Clinical Findings," *Neuroradiology*, 38:181-185 (1996).
Gandorfer, A., et al., "Posterior Vitreous Detachment Induced by Microplasmin," *OVS*, 45(2): 641-647 (2004).
Gandorfer, A., et al., "Ultrastructure of the viteoretinal interface following plasmin assisted vitrectomy," *Br. J. Ophthalmol.*, 85: 6-10 (2001).
GE Healthcare—Affinity chromatography (Data File 18-1139-38 AC—first published Sep. 2000).
Goretzki, L., et al., "Binding of the NG2 Proteoglycan to Kringle Domains Modulates the Functional Properties of Angiostatin and Plasmin(ogen)," *J. Biol. Chem.*, 275(37): 2862528633 (2000).
Greig, at al., "Protamine-Heparin complex as a substrate for plasmin," Biochim. Biophys. Ada., (1963), vol. 67, pp. 658-668.
Gribskov, M., and Richard R. Burgess, "Sigma factors from *E. coli*, B. subtilis, phage SP01, and phage T4 are homologous proteins," *Nucl. Acids Res.*, 14(6): 6745-6763 (1986).
Hagenson, M.J. et al., "Expression of Streptokinase in *Pichia pastoris* yeast," *Enzyme. Microb. Technol.* 11:650-656 (1989).
Haidacher, D., et al., "Temperature effects in hydrophobic interaction chromatography," Proc Natl Acad Sci USA 93:2290-2295 (1996).
Hedner, U., at al., "Effects of Porcine Plasmin on the Coagulation and Fibdnolytic Systems in Humans," *Blood*, 51(1):157-164 (1978).
Holmberg, L., et al., "Purification of Urokinase by Affinity Chromatography," *Biochim. Biophys. Acta.*, aaa 215-222 (1976).
Hoover, G.J., et al., "Amino Acids of the Recombinant Kringle 1 Domain of Human Plasminogen that Stabilize Its Interaction with 0)-Amino Acids," *Biochemistry*, 32(41): 10936-10943 (1993).
Horrevoets, A.J.G., et al., "Production and Characterization of Recominant Human Plasminogen (S741 C-Fluorescein): A Novel Approach to Study Zymogen Activation Without Generation of Active Protease," *J. Bio. Chem.*, 272(4): 2176-2182 (1997).
Horrevoets, A.J.G., et al., "The Activation-resistant Comformation of Recombinant Human Plasminogen Is Stabilized by Basic Residues in the Amino-terminal Hinge Region," *J. Bio. Chem.*, 270(26): 15770-15776 (1995).
Houghten, R.A., "General method for the rapid solid-phase synthesis of large numbers of peptides: Specificity of antigen-antibody interaction at the level of individual amino acids," *Proc. Natl. Acad. Sci. USA*, 82: 5131-5135 (1985).
Pharmacia Biotech., Data File: 18-1117-58 (AA Edition), Sephadex® ion exchange media; Ion exchange chromatography. Downloaded from world wide web on Dec. 11, 2010 (http://www.chembio.uoguelph.ca/educmat/chm357/sephadex.pdf).
Martin, L., "Acid-Base Balance," in Pulmonary Physiology in Clinical Practice, The Essentials for Patient Care and Evaluation, Chapter 7, pp. 1-4. Downloaded from world wide web on Nov. 29, 2011 (http://lakesidepress.com/pulmonary/books/physiology/chap7_1.htm).
Hunt and Novokhatny, *Journal of Thrombosis and Haemostasis* 2005; 3(1): Abstract No. P0781, for 20[th]International Society on Thrombosis and Haemostasis Congress, Sydney, Australia.
Hunt and Novokhatny, Poster presented Tuesday, Aug. 9, 2005 at 20[th]International Society on Thrombosis and Haemostasis Congress, Sydney, Australia.
Hunt, J.A., et al., "Simplified Recombinant Plasmin: Production and Functional Comparison of a Novel Thrombolytic Molecule with Plasma-Derived Plasmin," *Thromb. Haemost.*, 100: 413419 (2008).
International Search Report (PCT/US03/34020, dated Jul. 27, 2004).

International Search Report (PCT/US05/013562, dated Nov. 3, 2005).
International Search Report (PCT/US06/040940, dated Oct. 18, 2006).
Ito, et al., "Separation of Human Glu-Plasminogen, Lys-Plasminogen and Plasmin by High-Performance Affinity Chromatography on Asahipak GS Gel Coupled with pAminobebnzamidine," Journal of Chromatography, 348: 199-204 (1985).
IX. Plasmin in "Pharmaceutical Enzymes" (eds. R. Ruyssen & A. Lauwers)—Story Scientia, Gent, Belgium, (1978), pos. 123-131.
Jespersen, J., et al., The autodigestion of human plasmin follows a bimolecular mode of reaction subject to product inhibition, *Thromb. Res.* 41(3):395-404 (1986).
Johanson, K., et al., "Binding Interactions of Human Interleukin 5 with Its Receptor a Subunit," *J. Biol. Chem.*, 270(16): 9459-9471 (1995).
Johnson, A.J., et al., "Assay methods and standard preparations for plasmin, plasminogen and urokinase in purified systems, 1967-1968," *Thrornb. Diath. Haemorrh.*, 21(2):259-72 (1969).
Kirkwood, T.B.L., at al., "A standard for human plasmin," *Thromb. Diath. Haemorrh.*, 34(1):20-30 (1975).
Kitamoto, Y., et al., "A Femoral Vein Catheter with Immobilized Urokinase (UKFC) as an Antithrombotic Blood Access," *Trans. Am. Soc. Artif. Intern. Organs*, 33:136-139 (1987).
Kline, D.L. and J.B. Fishman, Preparation, Stabilization and Some Properties of Purified Human Plasmin, *Thromb. Diath. Haemorrh.*, 11:75-84 (1964).
Kline, D.L., "The Purification and Crystallization of Plasminogen (Profibrinolysin)," *Journal of Biological Chemistry* 204:949-955 (1953).
Knight, L.C., "Radiopharmaceuticals for Thrombus Detection," Seminars in Nuclear Medicine, 20(1):52-67 (1990).
Kolev, K., et al., "Functional Evaluation of the Structural Features of Proteases and Their Substrate in Fibrin Surface De radation," *J. Biol. Chem.*, 272(21): 13666-75 (1997).
Komorowicz, E., et al., "Fibrinolysis with Des-Kringle Derivatives of Plasmin and Its Modulation by Plasma Protease Inhibitors," *Biochemistry*, 37(25): 9112-9118 (1998).
Kulisek, E.S., et al., "A Chromogenic Assay for the Detection of Plasmin Generated by Plasminogen Activator Immobilized on Nitrocellulose Using a para-Nitroanilide Synthetic Peptide Substrate," *Analytical Biochemistry* 177: 78-84 (1989).
Lagerstedt, C., et al., "99mTc plasmin in 394 consecutive patients with suspected deep venous thrombosis," Eur J Nucl Med, 15:771-775 (1989).
Langer-Safer et al., Replacement of finger and growth factor domains of tissue plasminogen activator with plasminogen kringle 1, J. Biol. Chem. 265(6):3715-3723 (Feb. 25, 199).
Larsen, V., "Fibrinolytic Enzyme in the Treatment of Patients with Cancer," *Danish Medical Bulletin*, 2(5):137-140 (1964).
Larson, V., at al., "Fibrinolytic Treatment with Activator-Free Porcine Plasmin," *Scand. J. Clin. Invest* 18(Suppl. 89):34-73 (1966).
Lazzaro, C.R. et al., "Modified use of the arrow-trerotola percutaneous thrombolytic device for the treatment of trombosed hemodialysis access grafts'," J. Vasc Inter Radiol, (Sep. 1999), vol. 10, No. 8, pp. 1025-1031.
Lee, H., et al., "Disruption of Interkringle Disulfide Bond of Plasminogen Kringle 1-3 Changes the Lysine Binding Capability of Kringle 2, But Not Its Antiangiogenic Activity," *Arch. Biochem. Biophys.*, 375(2): 359-363 (2000).
Lerch, P.G., et al., "Localization of Individual Lysine-Binding Regions in Human Plasminogen and Investigations on Their Complex-Forming Properties," *Eur. I Biochem.*, 107(1): 7-13 (1980).
Li, X., et al., "Posterior Vitreous Detachment with Plasmin in the isolated Human Eye," *Graefe's Arch. Clin. Exp. Ophthalmol.*, 240:56-62 (2002).
Lijnen, H.R., et al., "Activation of plasminogen by pro-urokinase," *J. Biol. Chem.*, 261(1):1253-1258 (1986).
Lin, L-F., et al., "Epsilon Amino Caproic Acid Inhibits Streptokinase—Plasminogen Activator Complex Formation and Substrate Binding through Kringle-Dependent Mechanisms," *Biochemistry*, 39: 4740-4745 (2000).

(56) References Cited

OTHER PUBLICATIONS

Ling, C.M., et al., "Mechanism of formation of bovine plasminogen activator from human plasmin," *J. Biol. Chem.*, 240(11):4213-8 (1965).

Lippschutz, E.L., et aL, "Controlled study of the treatment of coronary occulsion with urokinase-activated human plasmin," *Am. J. Cardiot*, 16:93-98 (1965).

Lizano, S., et al., "Streptokinase-Mediated Plasminogen Activation Using a Recombinant Dual Fusion Protein Construct. A Novel Approach to Study Bacterial-Host Protein Interactions," *J. Microbiol. Methods*, 23: 261-280 (1995).

Lucas, M.A., et al., "The Binding of Human Plasminogen to Fibrin and Fibrinogen," *J. Biol. Chem.*, 258(7): 4249-4256 (1983).

Madison, E.L., "Probing Structure-Function Relationships of Tissue-Type Plasminogen Activator by Site-Specific Mutagenesis," *Fibrinolysis* 8 Supp.1:221-236 (1994).

Malke, H., et al., "Expression of a Streptokinase Gene from *Streptoccis equisimilisin Streptococcus sanguis*," *Mot. Gen. Genet*. 196: 360-363 (1984).

Malke, H., et al., "Nucleotide Sequence of the Streptokinase Gene from Streptococcus equisimilis H46A," *Gene* 34: 357-362 (1985).

Malke, H., et al., "Streptokinase: Cloning, Expression and Excretion by *Escherichia coli*," *Proc. Nat'l Acad. Sci.* 81:3557-3561 (1984).

Marder, V.J., et al., "Haemostatic Safety of a Unique Recombinant Plasmin Molecule Lacking Kringles 2-5," *Thromb. Haemost.*, 104: 780-787 (2010).

Marder, V.J., et al., "Plasmin Induces Local Thrombolysis without Causing Hemorrhage: A Comparison with Tissue Plasminogen Activator in the Rabbit," Thromb Haemost, 86:739-745 (2001).

Martin, at al., "Pulmonary Physiology in Clinical Practice, The Essentials for Patient Care and Evaluation," The C.V. Mosby Company, 1987, Chap. 7, Acid-base balance,.129-146.

Mathey D.G., et al., "Intravenous Urokinase in Acute Myocardial Infarction," *Am. J. Cardiol.*, 55:878-882 (1985).

Matsuka, Y.V., et al., "Fluorescence spectroscopic analysis of ligand binding to kringle 1+2+3 and kringle 1 fragments from human plasminogen," *Eur. J. Biochem.*, 190: 93-97 (1990).

McCance, S., et al., "Amino Acid Residues of the Kringle-4 and Kringle-5 Domains of Human Plasminogen that Stabilize their Interactions with 0-Amino Acid Ligands," *J. Biol. Chem.*, 269(51): 32405-32410 (1994).

Medynski, D., et al., "Refolding, purification, and activation of miniplasminogen and microplasminogen isolated from *E. coli* inclusion bodies," *Protein Expression and Purification* 52:395-402 (2007).

Menhart, N., et al., "Functional Independence of the Kringle 4 and Kringle 5 Regions of Human Plasminogen," *Biochemistry*, 32: 8799-8806 (1993).

Milne, R.M., et al., "Postoperative Deep Venous Thrombosis: A Comparison of Diagnostic Techniques," Lancet, 2 (7722):445-447 (1971).

Mizutani et al. "Potential thrombolysis under selective infusion of autolotous plasmin (AP) solution," *Japanese Heart Journal*, 30(5):723-732 (1989).

Moser, K., "Effects of Intravenous Administration of Fibrinolysin (Plasmin) in MaR" *Circulation*, 20:42-55 (1959).

Motta, A., et al., "Complete Assignment of the Aromatic Proton Magnetic Resonance Spectrum of the Kringle 1 Domain from Human Plasminogen: Structure of the Ligand-Binding Site," *Biochemistry*, 26(13): 3827-3836 (1987).

Mukhopadhyay, A., "Inclusion Bodies and Purification of Proteins in Biologically Active Forms," *Advances in Bio. Eng./Biotech.* 56:61-109 (1997).

Nahum, L.H., et al., "Fibrinolysis. II. Evaluation of enzymatic thrombolysis: Experiments with plasmin preparations in arterial, venous thrombosis," *Conn. Med.* 24:139-46 (1960).

Nilsson, T. and B. Wiman, On the structure of the stable complex between plasmin and alpha-2-antiplasmin, *FEBS Lett.*, 142(1):111-114 (1982).

Noren, C.J., et al., "A General Method for Site-Specific Incorporation of Unnatural Amino Acids into Proteins," *Science*, 244: 182-188 (1989).

Novokhatny, V. et al. "Thrombolytic potential of locally delivered active plasmin (Pm): In vitro assessment and in vivo comparison with tPA in the rabbit jugular vein trombosis model," Blood, 92(10) Suppl. 2, Abstract 3400. (Nov. 15, 1998).

Novokhatny, V., and Stanislav A. Kudinov, "Domains in Human Plasminogen," J. MoL Biol., 179: 215-232 (1984).

Novokhatny, V., at al., "Analysis of Ligand Binding to Kringles 4 and 5 Fragments from Human Plasminogen," *Thromb Res.*, 53(3): 243-52 (1989).

Novokhatny, V., et al., "Thrombolytic potency of acid-stabilized plasmin: superiority over tissue-type plasminogen activator in an in vitro model of catheter-assisted thrombolysis," *J Thromb. Haemost.*, 1(5): 1034-1041 (2003).

Novokhatny, V., et al., "Domain Structure and Domain-Domain Interaction of recombinant Tissue Plasminogen Activator," *J. Biol. Chem.* 266(20):12994-13002 (1991).

Obukowicz, M.G., et al., "Secretion of Active Kringle-2—Serine Protease in *Escherichia coli*," *Biochemistry* 29:9737-9745 (1990).

Ouellette, "Introduction to General, Organic, and Biological Chemistry," Second Edition (1988). The Ohio State University. Macmillan Publishing Company, New York, NY, pp. 288-290.

Owunwanne, et al., "Technetium Tc 99m plasmin in the diagnosis of inflammatory disease," Eur J. Nucl. Med., (1987), vol. 12, No. 10, pp. 496-499.

Patthy, L., et al., "Evolution of the Proteases of Blood Coagulation and Fibrinolysis by Assembly from Modules," *Cell* 41:657-663 (1985).

Perrson, B. and Darte, L., "Labeling Plasmin with Technetium-99m for Scintigraphic Localization of Thrombi," International Journal of Applied Radiation and Isotopes, 28:97-104 (1977).

Petitpretz, P., et al., "Effects of a single bolus of urokinase in patients with life-threatening pulmonary emboli: a descriptive trial," *Circulation*, 70(5): 861-866 (1984).

Powell, J.R., and Francis J. Castellino, "Activation of Human Neo-Plasminogen-Va1442 by Urokinase and Streptokinase and a Kinetic Characterization of Neo-Plasmin-Va1442," *J. Biol. Chem.*, 255(11): 5329-5335 (1990).

Quigley, J.P., "Plasminogen, the Serum Proenzyme Activated by Factors from Cells Transformed by Oncogenic Viruses," *J. Bio. Chem.* 249(13): 4300-4311 (1974).

Rasmussen, A., et al., "Distinction by Radioisotope Technique of a Subgroup with Increased Thrombophilic Potential among Patients Submitted to Major Abdominal Surgery," Journal of Medicine, 17(5-6):357-364 (1986).

Rejante, M.R. and M. Llinas, "Solution structure of the e-aminohexanoic acid complex of human plasminogen kringle 1," *Eur. J. Biochem.*, 221(3): 939-949 (1994).

Rimon, A., et al., "Studies on the Activation of Plasminogen: Preparation and Properties of an Insoluble Derivative of Streptokinase," *Biochem. Biophy. Acta* 73: 301-310 (1963).

Robbins, K.C. and L Summaria, "Plasminogen and Plasmin," *Meth. Enzymol.* 45:257-273 (1976).

Robbins, K.C. et al. "Purification of Human Plasminogen and Plasmin by Gel Filtration of Sephadex and Chromatography on Diethylaminoethyl Sephadex". Journal of Biological Chemistry (1963), vol. 238, pp. 952-962.

Robbins, K.C., et al., "The peptide chains of human plasmin. Mechanism of activation of human plasminogen to plasmin," *J. BioL Chem.*, 242(10):2333-42 (1967).

Robbins, KC., et al., "Human Plasminogen and Plasmin," *Methods in Enzymology*, 19:184-199 (1970).

S. Husain, "A single-step separation of the one-and two-chain forms of tissue plasminogen activator'," Arch Biochem Biophys., (1991), vol. 285, p.s. 373-376.

Sakata, Y., at al., "Differential binding of plasminogen to crosslinked and noncrosslinked fibrins: its significance in hemostatic defect in factorXIII deficiency," Blood, 63:1393-1401 (1984).

Schmer• "The purification of bovine thrombin by affinity chromatography on benzamidine-agarose," *Hoppe Seyler's Z Physiol Chem.*, 353: 810-814 (1972).

(56) References Cited

OTHER PUBLICATIONS

Schwartz, R.M. and M.O. Dayhoff, "Matrices for Detecting Distant Relationships," *Atlas of Protein Sequence and Structure*, 5(3): 353-358 (1978).
Segel, "How to solve mathematical problems in general biochemsitry," Biochemical Calculations, $2^{nd}$ Edition (1976), pis. 83-85.
Seifert, V., et a/., "Efficacy of Single Intracisternal Bolus Injection of Recombinant Tissue Plasminogen Activator to Prevent Delayed Cerebral Vasospasrn after Experimental Subarachnoid Hemorrhage," *Neurosurgery*, 25(4): 590-598 (1989).
Semba et al., "Iliofemoral deep venous thromosis: Aggressive therapy with catheter-directed thrombolysis," Radiology, (1994), vol. 191, pis. 487-494.
Sgouris, J,T, et al. "The preparation of human fibrinolysin (plasmin)," *Vox Sang.*, 5:357-76 (1960).
Sherry S., "The Origin of Thrombolytic Therapy," *J. Am. Coll. Cardiol.*, 14(4):1085-1092 (1989).
Shi, et al., "Differential autolysis of human plasmin at various pH levels," Thrombosis Research, 1988, vol. 51, pp. 355-364.
Shi, G-Y., et al., "Function of Streptokinase Fragments in Plasminogen Activation," *Biochem. J.* 304: 235-241 (1994).
Shi, G-Y., et al., "Kringle Domains and Plasmin Denaturation," *Biochem. Biophys. Res. Comm.*, 178(1): 360-368 (1991).
Shimura, et al., "High-performance affinity chromatography of plasmin and plasminogen on a hydrophilic vinyl-polymer gel coupled with p-aminobenzamicline," J. Chromatography, (1984), vol. 292, pp. 369-382.
Smith, L.J., et al., "Human Interleukin 4: The Solution Structure of a Four-helix Bundle Protein," *J. MoL Biol.*, 224: 899-904 (1992).
Smith, T.F., and Michael S. Waterman, "Comparison of Biosequences," *Advances in Applied Mathematics*, 2: 482-489 (1981).
Söhndel, S., et al., "Recombinant Gene Expression and 1H NMR characteristics of the Kringle (2+3) Supermodule: Spectroscopic/Functional Individuality of Plasminogen Kringle Domains," *Biochemistry* 35:2357-2364 (1996).
Sottrup-Jensen, L., et al., "The Primary Structure of Human Plasminogen: Isolation of Two Lysine-Binding Fragments and One "Mini-" Plasminogen (MW, 38,000) by Elastase-Catalyzed-Specific Limited Proteolysis," *Prog. Chem. Fibrinol. Thrombol.*, 3: 191-209 (1978).
Stewart, D., et al., "Distinct dose-dependent effects of plasmin and TPA on coagulation and hemorrhage," *Blood*, 101(8): 3002-3007 (2003).
Suenson, E. and Thorsen, S., "Secondary-site binding of Glu-plasmin, Lys-plasmin and miniplasmin to fibrin," Biochem. J., 197:619-628 (1981).
Sugitachi, A., et al., "Immobulization of Plasminogen Activator, Urokinase, on Nylon," *Thrombos. Haemostas (Stuttg.)* 39: 426-436 (1978).
Summaria, L., et al., The specific mechanism of activation of human plasminogen to plasmin, *J. Biol. Chem.*, 242(19):4279-83 (1967).
Summaria, L., et al., "Recombinant human Lys-plasmin and the Lys-plasmin streptokinase complex,"*J. Biol. Chem*, 254(14):6811-4 (1979).
Supplementary Partial European Search Report (EP 00 99 1956, dated Dec. 17, 2004).
Tengborn, L, et al., "Demonstration of 99m-Tc-Labelled Plasmin an the Surface of Ex Vivo Thrombi," Thrombosis Research, 28:783-791 (1982).
Thewes, T., of al., "Ligand Interactions with the Kringle 5 Domain of Plasminogen," *J. Biol. Chem.*, 265(7): 3906-3915 (1990).
Trese, M.T., "Enzymatic Vitreous Surgery," *Seminars in Ophthalmology*, 15(2): 116-121 (2000).
Ueshima, S., et al., "Stabilization of plasmin by lysine derivatives," *Clin. Chim. Acta.*, 245(1):7-18 (1996).

Uflacker R, et al., "Treatment of thrombosed dialysis access grafts: Randomized trial of surgical thrombectomy versus mechanical thrombectomy with the amplatz device'," JVIR, (1996), vol. 7, No. 2, pp. 185-192.
Vali, Z. and Patthy, L, "The Fibrin-binding Site of Human Plasminogen," Journal of Biological Chemistry, 269 (22)13690-13694 (1984).
Van Zonneveld, A-J., et al., "Autonomous functions of structural domains on human tissue-type plasminogen activator," *PNAS*, 83: 4670-4674 (1986).
Verstraete, M., The Fibrinolytic System: from Petri Dishes to Genetic Engineering, *Thrombosis and Haemostasis*, 74(1):25-35 (1995).
Verstraeten, T.C., et al., "Pharmacologic Induction of Posterior Vitreous Detachment in the Rabbit," *Arch Ophthalmol.,*, 111: 849-854 1993.
Walker, B., et al., "Strategies for the inhibition of serine proteases," CMLS. Cell. Mol. Life Sci., vol. 58, (2001), pp. 596-624.
Wang, F., et al., "Safety and Efficacy of Displase and Plasmin in Pharmacologic Vitreolysis," *OVS*, 45(9): 3286-3290 (2004).
Wang, J., et al., "Structure and Function of Microplasminogen: I. Methionine Shuffling, Chemical Proteolysis, and Proenzyme Activation," *Protein Sci.* 4:1758-1767 (1995).
Wang, S., et al., "Deletion of Ile 1 Changes the Mechanism of Streptokinase: Evidence for the Molecular Sexuality Hypothesis," *Biochemistry*, 38: 5232-5240 (1999).
Wang, Z-L, et al., "PVD Following Plasmin But Not Hyaluronidase: Implications for Combination Pharmacologic Vitreolysis Therapy," *Retina*, 25: 38-43 (2005).
Whisenant, B. K., et al., "Rheolytic thrombectomy with the possis AngioJet¨. Technical considerations and Initial clinical experience," J. of Invasive Cardiology, vol. 11, No. 7, (Jul. 1999), pp. 421-426.
Williams, J.G., et al., "Autologous Plasmin Enzyme in the Surgical Management of Diabetic Retinopathy," *Ophthalmology* 108(10): 1902-1905 (2001).
Wiman, B and Desire Collen, "Molecular Mechanism of Physiological Fibrinolysis," *Nature*, 272: 549-550 (1978).
Wiman, B. and Desire Collen, "On the Kinetics of the Reaction between Human Antiplasmin and Plasmin," *Eur. J. Biochem.*, 84: 573-578 (1978).
Wiman, B., "Affinity-chromatographic purification of human alpha 2-antiplasmin," *Biochem. J.*, 191M:229-232 (1980).
Wiman, B., et al., "On the Specific Interaction Between the Lysine-Binding Sites in Plasmin and Complementary Sites in a2—Antiplasmin and in Fibrinogen," *Biochim. Biophys. Acta*, 579: 142-154 (1979).
Wiman, B., and Per Wallén, "Activation of Human Plasminogen by an Insoluble Derivative of Urokinase Structural Changes of Plasminogen in the course of Activation to Plasmin and Demonstration of a Possible Intermediate Compound," *Eur. J. Biochem.*, 36(1): 25-31 (1973).
Wohl, R.C., et al., "Kinetics of Activation of Human Plasminogen by Different Activator Species at pH 7.4 and 37° C.," *J. Biol. Chem.*, 255(5): 2005-2013 (1980).
Wohl, R.C., et al., "Steady State Kinetics of Activation of Human and Bovine Plasminogens by Streptokinase and Its Equimolar Complexes with Various Activated Forms of Human Plasminogen," *J. Biol. Chem.*, 253(5): 1402-1407 (1978).
Wong, S-L., et al., "Engineering and Production of Streptokinase in a Bacillus subtilis Expression-Secretion System," *Applied and Env. Microbiol.* 60(2): 517-523 (1994).
Wu, S-C., et al., A Fast-Acting Modular-Structured Staphylokinase Fusion with Kringle-1 From Human Plasminogen as the Fibrin-Targeting Domain Offers Improved Clot Lysis Efficacy, *J. Biol. Chem.* 278(20):18199-181206 (2003).
Wu, T P. et al., "The structure of recombinant plasminogen kringle 1 and the fibrin binding site," *Blood CoaguL Fibrinolysis*, 5(2): 157-166 (1994).
Wu, X-C., et al., "Engineering of Plasmin-Resistant Forms of Streptokinase and their Production in Bacillus subtilis: Streptokinase with Longer Functional Half-Life," *Applied and Envir. Micro.*, 64(3):824-829 (1998).

(56) References Cited

OTHER PUBLICATIONS

Zajicek, J., et al., "The Effects of Ligand Binding on the Backbone Dynamics of the Kringle 1 Domain of Human Plasminogen," *J. MoL Biol.*, 301(2): 333-347 (2000).

Zeit, R M., "Arterial and venous embolization: Declotting of dialysis shunts by direct injection of streptokinase," Radiology, (1986), vol. 159, No. 3, pp. 639-641.

CN 1167823A (Huang, C.) Dec. 17, 1997 (abstract) [online] Retrieved from Thomson Innovation, p. 1.

JP 0207 8633 (Green Cross Corp.) Mar. 19, 1990 (abstract) [online] Retrieved from Thomson Innovation, pp. 1-2.

JP 0906 5895 (Nitto Boseki Co. Ltd.) Mar. 11, 1997 (abstract) [online] Retrieved from Thomson Innovation, pp. 1-2.

RO 103 682 (Cantacuzino Inst.) Dec. 9, 1991 (abstract) [online] Retrieved from Espacenet, p. 1.

\* cited by examiner

FIGURE 1

```
  1  MetArgAspValValLeuPheGluLysLysValTyrLeuSerGluCysLysThrGlyAsn
 21  GlyLysAsnTyrArgGlyThrMetSerLysThrLysAsnGlyIleThrCysGlnLysTrp
 41  SerSerThrSerProHisArgProArgPheSerProAlaThrHisProSerGluGlyLeu
 61  GluGluAsnTyrCysArgAsnProAspAsnAspProGlnGlyProTrpCysTyrThrThr
 81  AspProGluLysArgTyrAspTyrCysAspValProGlnCysAlaAlaProSerPheAsp
101  CysGlyLysProGlnValGluProLysLysCysProGlyArgValValGlyGlyCysVal
121  AlaHisProHisSerTrpProTrpGlnValSerLeuArgThrArgPheGlyMetHisPhe
141  CysGlyGlyThrLeuIleSerProGluTrpValLeuThrAlaAlaHisCysLeuGluLys
161  SerProArgProSerSerTyrLysValIleLeuGlyAlaHisGlnGluValAsnLeuGlu
181  ProHisValGlnGluIleGluValSerArgLeuPheLeuGluProThrArgLysAspIle
201  AlaLeuLeuLysLeuSerSerProAlaValIleThrAspLysValIleProAlaCysLeu
221  ProSerProAsnTyrValValAlaAspArgThrGluCysPheIleThrGlyTrpGlyGlu
241  ThrGlnGlyThrPheGlyAlaGlyLeuLeuLysGluAlaGlnLeuProValIleGluAsn
261  LysValCysAsnArgTyrGluPheLeuAsnGlyArgValGlnSerThrGluLeuCysAla
281  GlyHisLeuAlaGlyGlyThrAspSerCysGlnGlyAspSerGlyGlyProLeuValCys
301  PheGluLysAspLysTyrIleLeuGlnGlyValThrSerTrpGlyLeuGlyCysAlaArg
321  ProAsnLysProGlyValTyrValArgValSerArgPheValThrTrpIleGluGlyVal
341  MetArgAsnAsn (SEQ ID NO:1)
```

FIGURE 2

```
-19                     1
MEHKEVVLLLLLFLKSGQGEPLDDYVNTQGASLFSVTKKQLGAGSIEECAAKCEEDEEFTCRAFQ

78
YHSKEQQCVIMAENRKSSIIIRMRDVVLFEKKVYLSECKTGNGKNYRGTMSKTKNGITCQKWSST 136     143       153       162
SPHRPRFSPATHPSEGLEENYCRNPDNDPQGPWCYTTDPEKRYDYCDILECEEECMHCSGENYDG
    kringle 1

234
KISKTMSGLECQAWDSQSPHAHGYIPSKFPNKNLKKNYCRNPDRELRPWCFTTDPNKRWELCDIP
        kringle 2

RCTTPPPSSGPTYQCLKGTGENYRGNVAVTVSGHTCQHWSAQTPHTHNRTPENFPCKNLDENYCR
                                                            kringle 3

324
NPDGKRAPWCHTTNSQVRWEYCKIPSCDSSPVSTEQLAPTAPPELTPVVQDCYHGDGQSYRGTSS

426
TTTTGKKCQSWSSMTPHRHQKTPENYPNAGLTMNYCRNPDADKGPWCFTTDPSVRWEYCNLKKCS
            kringle 4

GTEASVVAPPPVVLLPDVETPSEEDCMFGNGKGYRGKRATTVTGTPCQDWAAQEPHRHSIFTPET
                                                            kringle 5
                    532       542                    561
NPRAGLEKNYCRNPDGDVGGPWCYTTNPRKLYDYCDVPQCAAPSFDCGKPQVEPKKCPGRVVGGC

VAHPHSWPWQVSLRTRFGMHFCGGTLISPEWVLTAAHCLEKSPRPSSYKVILGAHQEVNLEPHVQ

EIEVSRLFLEPTRKDIALLKLSSPAVITDKVIPACLPSPNYVVADRTECFITGWGETQGTFGAGL

LKEAQLPVIENKVCNRYEFLNGRVQSTELCAGHLAGGTDSCQGDSGGPLVCFEKDKYILQGVTSW

791
GLGCARPNKPGVYVRVSRFVTWIEGVMRNN  (SEQ ID NO: 2)
```

FIGURE 3

```
HK1  CKTGNGKNYR  GTMSKTKNGI  TCQKWSSTSP  HR-PRFSPAT  HPSEGLEENY
HK2  CMHCSGENYD  GKISKTMSGL  ECQAWDSQSP  HA-HGYIPSK  FPNKNLKKNY
HK3  CLKGTGENYR  GNVAVTVSGH  TCQHWSAQTP  HT-HNRTPEN  FPCKNLDENY
HK4  CYHGDGQSYR  GTSSTTTGK   KCQSWSSMTP  HR-HQKTPEN  YPNAGLTMNY
HK5  CMFGNGKGYR  GKRATTVTGT  PCQDWAAQEP  HRHSIFTPET  NPRAGLEKNY (con't)
HK1  CRNPDNDPQG  PWCYTTDPEK  RYDYCDILEC     (SEQ ID NO:3)
HK2  CRNPDRE-LR  PWCFTTDPNK  RWELCDIPRC     (SEQ ID NO:4)
HK3  CRNPDGK-RA  PWCHTTNSQV  RWEYCKIPSC     (SEQ ID NO:5)
HK4  CRNPDAD-KG  PWCFTTDPSV  RWEYCNLKKC     (SEQ ID NO:6)
HK5  CRNPDGDVGG  PWCYTTNPRK  LYDYCDVPQC     (SEQ ID NO:7)
```

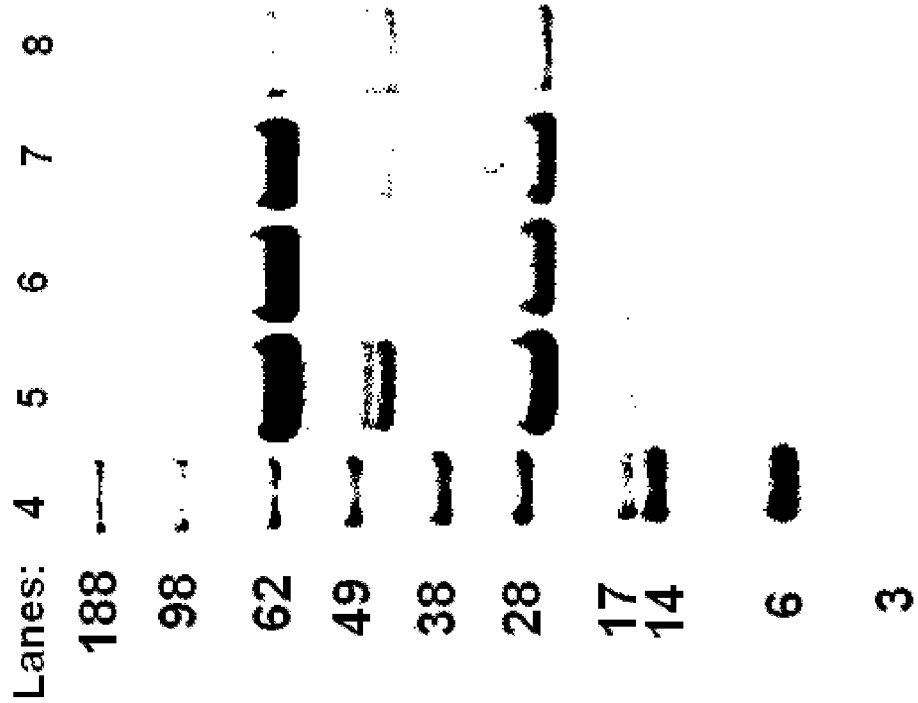

COMPOSITIONS, METHODS AND KITS FOR PREPARING PLASMINOGEN AND PLASMIN PREPARED THEREFROM

CROSS-REFERENCE TO RELATED APPLICATIONS

This application is a national phase of International Application PCT/US10/025898, filed Mar. 2, 2010, which claims priority under 35 USC §119 to U.S. Provisional Application No. 61/156,990, filed Mar. 3, 2009, each of which is herein incorporated by reference in its entirety.

FIELD OF THE INVENTION

This invention relates to both a method for preparing plasminogen and a method for preparing plasmin from the plasminogen, in particular recombinant plasminogen. This invention also relates to compositions and kits comprising recombinant plasminogen and/or plasmin prepared therefrom.

BACKGROUND OF THE INVENTION

The production of large quantities of relatively pure polypeptides and proteins is important for the manufacture of many pharmaceutical formulations. For production of many proteins, recombinant DNA techniques have been employed in part because large quantities of exogenous proteins can be expressed in host cells.

Plasmin, the principle fibrinolytic enzyme in mammals, is a serine protease with trypsin-like specificity that is derived from the inactive zymogen precursor plasminogen circulating in plasma. Plasminogen itself is a 790 amino acid polypeptide having an N-terminus glutamate residue. Plasminogen activators such as streptokinase, tissue plasminogen activator (tPA) or urokinase will cleave the single-chain plasminogen molecule to produce active plasmin at the Arg560-Val561 peptide bond. The resulting two polypeptide chains of plasmin are held together by two interchain disulfide bridges. The light chain of 25 kDa carries the catalytic center and is homologous to trypsin and other serine proteases. The heavy chain (60 kDa) consists of five triple-loop kringle structures with highly similar amino acid sequences. Some of these kringles contain so-called lysine-binding sites that are responsible for plasminogen and plasmin interaction with fibrin, α2-antiplasmin, or other proteins.

Plasmin as a potential thrombolytic agent has numerous technical difficulties. These difficulties include the challenge of preparing pure plasmin that is relatively free of functional traces of the plasminogen activator used to generate plasmin from its inactive precursor, plasminogen. Preparations of plasmin are typically extensively contaminated by plasminogen activator, streptokinase or urokinase, and the thrombolytic activity has been, therefore, attributed to the contaminating plasminogen activators rather than to plasmin itself. The contaminating plasminogen activators could also trigger systemic bleeding other than at the targeted site of thrombosis. Another important technical factor limiting clinical use of plasmin is that plasmin, as a serine protease with broad specificity, is highly prone to autodegradation and loss of activity. This circumstance provides severe challenges to the production of high-quality plasmin, to the stable formulation of this active protease for prolonged periods of storage prior to use, and to safe and effective administration of plasmin to human patients suffering from occlusive thrombi.

Preparative isolation of recombinant plasminogen or plasmin prepared from recombinant plasminogen resulting in pharmaceutical purity and sufficient yield has eluded the art. Thus, there is need for compositions and methods for preparing a recombinant plasminogen and plasmin prepared from recombinant plasminogen activated by a plasminogen activator.

SUMMARY OF THE INVENTION

There is now provided compositions and methods for preparing a plasminogen; and for preparing a plasmin therefrom.

In one aspect, the present invention provides a method for preparing plasminogen. The method comprises contacting a composition comprising a plasminogen with a cation-exchange medium under a cation-exchange condition that is sufficient for the cation-exchange medium to bind the plasminogen.

In another aspect, the present invention provides a method for preparing plasminogen, the method comprising:

(a) expressing a recombinant plasminogen using a recombinant expression system under an expression condition sufficient to produce a recombinant plasminogen inclusion body;

(b) contacting the recombinant plasminogen inclusion body with a solubilization buffer under a solubilization condition sufficient to obtain a solubilized recombinant plasminogen inclusion body;

(c) contacting the solubilized recombinant plasminogen inclusion body with a refolding solution under a refolding condition to obtain a composition comprising the recombinant plasminogen;

(d) diafiltering the composition subsequent to step (c);

(e) contacting the composition with a cation-exchange medium under an ion-exchange condition that is sufficient for the cation-exchange medium to bind the recombinant plasminogen;

(f) eluting the recombinant plasminogen captured by the cation-exchange medium to obtain a cation-exchange medium eluate comprising the recombinant plasminogen;

(g) contacting the cation-exchange medium eluate with a first affinity medium under a first affinity condition that is sufficient for the first affinity medium to bind the recombinant plasminogen; and (h) eluting the recombinant plasminogen bound by the first affinity medium to obtain a plasminogen solution comprising the recombinant plasminogen.

In other aspects, the present invention provides a method for preparing plasmin, the method comprising:

(a) contacting a composition comprising a plasminogen with a cation-exchange medium under a cation-exchange condition that is sufficient for the cation-exchange medium to bind the plasminogen;

(b) contacting the plasminogen with a plasminogen activator in an activation solution under an activation condition sufficient to convert the plasminogen to a plasmin; and (c) contacting the plasmin with an anion-exchange medium under an anion-exchange condition such that the anion-exchange medium preferentially binds the plasminogen activator relative to the plasmin.

In one aspect, the present invention provides a method for preparing a plasmin. The method comprises: contacting a composition comprising the plasmin with an anion exchanger whereby, if present in the composition, a proteinaceous material having an isoelectric point below that of the plasmin is separated from the plasmin.

Also provided is a plasminogen and/or a plasmin prepared in accordance with the methods of the present invention.

Also provided are kits comprising one or more of the compositions of the present invention.

BRIEF DESCRIPTION OF THE DRAWINGS

FIG. 1 shows one embodiment of a recombinant plasminogen amino acid sequence (SEQ ID NO:1).

FIG. 2 shows the amino acid sequence of a human plasminogen (SEQ ID NO:2), showing the 19-residue leader sequence numbered as −19 to −1, and the plasminogen sequence shown as residues 1-791. A number of features are shown, including the following: one embodiment of a recombinant plasminogen amino acid sequence (shaded region corresponds to the amino acid sequence as set forth in SEQ ID NO:1); kringle domains 1-5 (double underscore); glycosylations sites Asn289 and Thr346 (in bold); the Arg-Val activation site ($R^{561}V^{562}$ in bold); and lysine-binding sites in kringle 1 (in underscore and with specific position numbering).

FIG. 3 shows polypeptide sequence comparisons (i.e., a gap alignment) between the five kringle domains (1-5) of native human plasmin(ogen). Amino acid residues that are identical to those of the same relative position in kringle 1 are shown in underscore.

FIG. 9 is a SDS-PAGE.

DESCRIPTION OF THE INVENTION

I. Plasminogen

Figure 4:
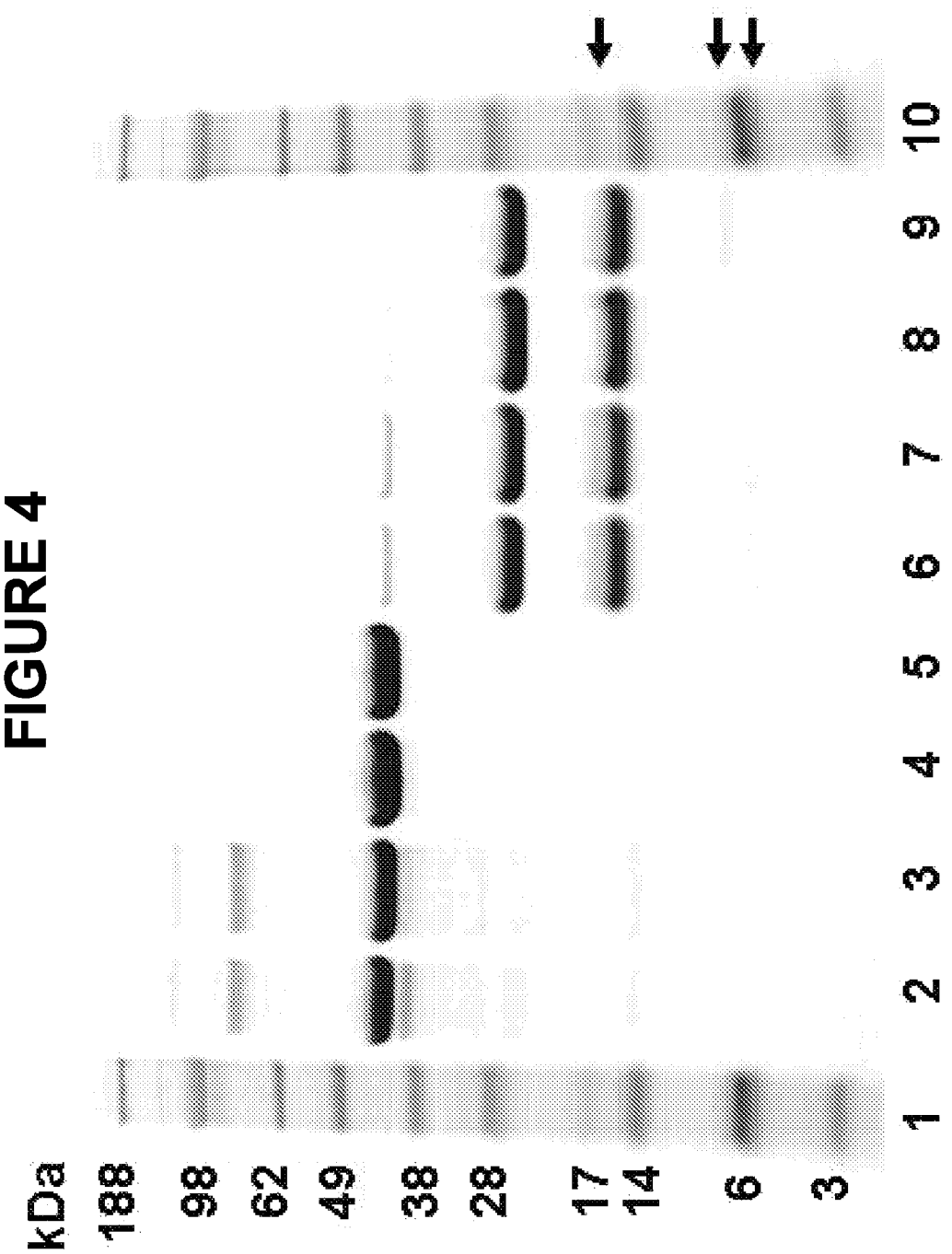
FIG. 4 shows a sodium dodecyl sulfate polyacrylamide gel electrophoresis (SDS-PAGE) gel of purification intermediates. Samples were run on a 4-12% polyacrylamide gel, under reducing conditions, and stained with Coomassie Blue R-350 dye. Gel lanes 2-9 were each loaded with 3.5 μg of total protein. Lanes 1 and 10, molecular weight markers; lane 2, solubilized inclusion bodies; lane 3, refolded recombinant plasminogen; lane 4, SP-SEPHAROSE™ eluate; lane 5, ECH-Lysine SEPHAROSE™ eluate; lane 6, plasmin; lane 7, Benzamidine SEPHAROSE™ load; lane 8, Benzamidine SEPHAROSE™ eluate; lane 9, final formulation plasmin. Arrows to the right of the gel indicate autolysis products of plasmin.

In one aspect, the present invention provides a method for preparing plasminogen, the method comprising:
contacting a composition comprising a plasminogen with a cation-exchange medium under a cation-exchange condition that is sufficient for the cation-exchange medium to bind the plasminogen.

The amino acid sequence of the plasminogen can correspond to or be based on any species including, but not limited to, a human, murine, bovine, ovine, porcine, equine, and avian, in native sequence or in a genetically engineered form, and from any source, whether natural, synthetic, or recombinantly produced. In one embodiment, the plasminogen corresponds to or is based on a human plasminogen.

In one embodiment, the plasminogen is recombinant plasminogen.

A. Cation-Exchange Chromatography

The cation-exchange medium can be a solid phase that binds the plasminogen present in the composition. The cation-exchange chromatography medium can be selected from any of the group of media commonly described as cation-exchange media, preferably a strong cation-exchange medium. The medium can possess a chemistry or a ligand coupled thereto that can allow for selective or preferential capture of the plasminogen from the composition. Useful chromatography media comprise a support and one or more ligand(s) bound thereto that provide(s) the selective or preferential binding capability for the plasminogen. Useful supports include, by way of illustrative example, polysaccharides such as agarose and cellulose, organic polymers such as polyacrylamide, methylmethacrylate, and polystyrene-divinylbenzene copolymers. It should be recognized that it is not intended herein to imply that only organic substrates are suitable for medium substrate use, since inorganic support materials such as silica and glasses also can be used.

In some embodiments, the cation-exchange medium is in the form of beads, which can be generally spherical, or alternatively the cation-exchange medium can be usefully provided in particulate or divided forms having other regular shapes or irregular shapes. Or, the medium can be in a membrane format. The cation-exchange medium can be of porous or nonporous character, and the medium can be compressible or incompressible. Preferred cation-exchange media will be physically and chemically resilient to the conditions employed in the plasminogen purification process including pumping and cross-flow filtration, and temperatures, pH, and other aspects of the various compositions employed. A wide variety of cation exchange media, for example, those wherein the coupled ligand is sulphopropyl or methylsulphate, are known in the art.

In one embodiment, the cation-exchange medium comprises a ligand coupled to a support, wherein the ligand is sulfopropyl (SP), wherein the support is an agarose. For example, cation-exchange chromatography can be performed in an SP-SEPHAROSE™ column format. SEPHAROSE™ is a registered trade mark for agarose gel in bead form.

Preferably, the cation-exchange condition is sufficient for the cation-exchange medium to selectively or preferentially bind the plasminogen present in the composition relative to one or more contaminating molecules that may also be present in the composition. The contaminating molecule can be a substance present in the composition that is different from the desired plasminogen molecule and is desirably excluded from the final plasminogen product. Contaminants can include, but are not limited to, nucleic acids, polypeptides including, but not limited to, unfolded and misfolded plasminogens, cell debris, endotoxins, etc.

For example, the composition can be passed over an SP column equilibrated with a suitable buffer. The pH of the suitable buffer can be at least about pH 3.0, illustratively, at least about: pH 3.0, 4.0, 5.0, 6.0, 7.0, 8.0, and 9.0. In some embodiments, the suitable buffer has an acidic pH, preferably at least about pH 4.0. In another embodiment, the suitable buffer has an alkaline pH, preferably a Tris-based buffer at least about pH 8.0. Following the load step, the column can be washed with the equilibration buffer or a different buffer so long as a substantial amount of the recombinant plasminogen remains bound to the medium.

In another embodiment, the method further comprises eluting the recombinant plasminogen that is bound by the cation-exchange medium to obtain a cation-exchange medium eluate comprising the recombinant plasminogen. For example, the medium-bound recombinant plasminogen can be eluted from the cation-exchange medium with an elution buffer comprising a suitable concentration of a salt. In one embodiment, a Tris-based buffer comprising at least about 200 mM NaCl is used to elute the recombinant plasminogen from an SP column.

B. Affinity Chromatography

The cation-exchange eluate comprising the recombinant plasminogen can be loaded directly onto a suitable affinity medium for affinity chromatography. Alternatively, the eluate can be subjected to further preparation steps prior to affinity chromatography. In some embodiments, the method for preparing plasminogen further comprises contacting the cation-exchange medium eluate with a first affinity medium under a first affinity condition that is sufficient for the affinity medium to bind the plasminogen.

In one embodiment, the first affinity medium comprises a ligand coupled to a support, wherein the ligand has affinity for the plasminogen.

The first affinity medium can be a solid phase that binds the plasminogen present in the composition. The medium can possess a chemistry or a ligand coupled thereto that can allow for selective or preferential capture of the plasminogen from the composition by way of affinity interactions. Useful affinity chromatography media comprise a support and one or more ligand(s) bound thereto that provide(s) the selective or preferential binding capability for the plasminogen. Useful supports include, by way of illustrative example, polysaccharides such as agarose and cellulose, organic polymers such as polyacrylamide, methylmethacrylate, and polystyrene-divinylbenzene copolymers. It should be recognized that it is not intended herein to imply that only organic substrates are suitable for medium substrate use, since inorganic support materials such as silica and glasses also can be used.

In some embodiments, the affinity medium is in the form of beads, which can be generally spherical, or alternatively the affinity medium can be usefully provided in particulate or divided forms having other regular shapes or irregular shapes. The affinity medium can be of porous or nonporous character, and the medium can be compressible or incompressible. Preferred affinity media will be physically and chemically resilient to the conditions employed in the plasminogen purification process. A wide variety of affinity media, for example, those wherein the coupled ligand is a lysine, an antibody, or metal ion, are known in the art.

In one embodiment, the affinity medium comprises a ligand coupled to a support. In another embodiment, the ligand is lysine, wherein the support is an agarose. For example, the first affinity medium can be performed in an ECH Lysine SEPHAROSE™ column format.

C. Recombinant Plasminogen

In some embodiments, the plasminogen is a recombinant plasminogen. For example, a nucleic acid molecule coding for the plasminogen of the present invention can be prepared from several sources, for example, through chemical synthesis using the known DNA sequence or by the use of standard cloning techniques known to those skilled in the art. cDNA clones carrying the plasminogen coding sequence can be identified by use of oligonucleotide hybridization probes specifically designed based on the known sequence of the plasminogen.

In one embodiment, the recombinant plasminogen, or a variant thereof, of the present invention is a recombinant zymogen that is capable of becoming activated to a functional plasmin enzyme following an activation event that at least involves proteolytic cleavage of an Arg-Val peptide bond located between the kringle domain and the serine protease domain of the zymogen.

The recombinant plasminogen, or variants, fragments, derivatives or analogs thereof, can have fibrin- and antiplasmin-binding as well as activation properties of full-length native human plasminogen. In various embodiments, the recombinant plasminogen and/or the plasmin derived therefrom can be characterized by at least one of the following:

i) in particular embodiments, lower molecular weights relative to native full-length plasmin(ogen) molecules resulting in increased specific activity (per mg of protein);

ii) in particular embodiments, lack of at least two glycosylation sites found in the native protein, combined with relatively low molecular weights, facilitates recombinant production of this protein using relatively inexpensive expression systems;

iii) in particular embodiments, the ability of the plasminogen to be activated by the plasminogen activator streptokinase, urokinase, tPA, and/or staphylokinase;

iv) in particular embodiments, the presence of a single N-terminal kringle domain homologous to a kringle domain of native human plasminogen, wherein the fibrin-binding properties of plasmin, which are important for thrombolytic efficacy, are preserved;

v) in particular embodiments, the presence of α2-antiplasmin-binding sites on the single N-terminal kringle domain homologous to a kringle domain of native human plasminogen, which can allow the plasmins to be inhibited rapidly by this physiological inhibitor of plasmin (a feature which can prevent bleeding);

vi) in particular embodiments, absence of kringle 5, which retains the primary binding site for intact, undigested fibrin (ogen), can allow use of the plasmin with reduced depletion of circulating fibrinogen;

vii) in particular embodiments, presence of a single N-terminal kringle domain homologous to a kringle domain of native human plasminogen, wherein the last four amino acid residues within the kringle domain are V, P, Q, and C, provides a native-like linkage to the serine protease domain (i.e., a linkage similar to the naturally occurring domain juncture between the kringle 5 domain and the serine protease domain of human plasminogen); and viii) in particular embodiments, following expression of the recombinant plasminogen, its N-terminus may be cleaved back (e.g., cleaved back during activation) to provide a native-like N-terminus.

In other embodiments, the recombinant plasminogen has a single-kringle-region N-terminal to the activation site and serine protease domain. In some embodiments, the single kringle region containing molecules can comprise additional sequences (additional N-terminal sequences derived from those of native kringle regions of a native plasminogen) N-terminal to the activation site. The N-terminal kringle domains can include kringle sequences of kringles 1 and 4 of native plasmin(ogen) and functional equivalents thereof. Further, particular embodiments of the recombinant plasminogens and the plasmins prepared therefrom can exhibit reduced immunogenicity by virtue of native-like structures. For example, in some embodiments, the recombinant plasminogen has an N-terminus identical to that of one of the naturally occurring forms of human plasma-derived plasminogen, which upon activation by the plasminogen activator (e.g., streptokinase), produces plasmin polypeptides comprising native-like N-termini. Additionally, in other embodiments, the recombinant plasminogen can have a sequence between the Kringle and Serine protease domains that is similar to the junction between Kringle 5 and the SP domain in naturally-occurring human plasmin.

In another embodiment, the present invention provides a method for preparing a recombinant plasminogen, wherein the recombinant plasminogen comprises the sequence shown in SEQ ID NO:1 (FIG. 1). In one embodiment, the recombinant plasminogen polypeptide is at least 90% or 95%, or 98% identical to the sequence shown in SEQ ID NO:1. In other embodiments, the recombinant plasminogen comprises a single kringle domain that is at least 90% or 95%, or 98% identical to the kringle 1 or kringle 4 domain of native human plasminogen; and the C-terminal domain is at least 90% or 95%, or 98% identical to the activation site and serine protease domain of human plasminogen. In some embodiments, the recombinant plasminogen polypeptide has an amino acid sequence as shown in SEQ ID NO:1, and conservative substitutions thereof. In other embodiments, the polypeptide has an arginine residue at a relative position analogous to that of position 85 of the amino acid sequence shown in SEQ ID NO:1.

In other embodiments, the recombinant plasminogens have a single kringle region N-terminal to the activation site and serine protease domain, wherein residues at certain positions of the single N-terminal kringle domain of the plasminogen are conserved relative to kringle 1 of native human plasminogen. These can be residues at positions associated with disulfide bridging and lysine binding, and include Cys84, Cys105, Cys133, Cys145, Cys157, and Cys162, and Pro136-Pro140, Pro143-Tyr146, and Arg153-Tyr156, respectively (positions numbered as shown in SEQ ID NO:2 (FIG. 2). Additionally, particular embodiments of the recombinant plasminogen can be characterized chemically by contrast to mini-plasmin(ogen) which has an analogous domain composition (i.e., kringle-serine protease (K-SP) (see Sottrup-Jensen, L., et al., Progress in Chemical Fibrinolysis and Thrombolysis, Vol. 3, (Eds: J. F. Davidson, et al.) Raven Press, New York (1978)) but, inter alia, lacks an arginine (Arg) at a relative position analogous to that of position 85 of the amino acid sequence shown in SEQ ID NO:1 (FIG. 1). In some embodiments, the recombinant plasminogen of the invention comprises a single N-terminal kringle domain comprising an Arg residue at a relative position analogous to that of position 85 of the amino acid sequence shown in SEQ ID NO:1. Non-limiting examples of a relative position analogous to that of position 85 of the amino acid sequence shown in SEQ ID NO:1 include Arg(153), Arg(234), Arg(324), and Arg(426) positions of the amino acid sequence shown in SEQ ID NO:2 (FIG. 2).

In other embodiments, the specific positions of the named residues can vary somewhat while still being present in the polypeptide at structurally and functionally analogous positions (i.e. relative to the kringle structure of the N-terminal domain; see Chang, Y., et al. as discussed above). In some embodiments, the single N-terminal kringle domain of the plasmin(ogen) polypeptide has at least one residue greater percent identity with kringle 1 or kringle 4 of native human plasminogen than with kringle 5 of native human plasminogen.

Further, in particular embodiments, the recombinant plasminogen can be characterized functionally by contrast to mini-plasmin(ogen). In one embodiment, the plasmin prepared from the recombinant plasminogen exhibits an increased rate of inhibition by $\alpha_2$-antiplasmin, e.g., as much as about one or two orders of magnitude faster than the rate of inhibition of mini-plasmin.

Characterization of the single N-terminal kringle domain of the plasminogen as "N-terminal" means only that the domain is present N-terminal to the activation site and does not mean that additional amino acid residues N-terminal to the domain itself are not present. Further, the number and identity of residues interposed between the most C-terminal cysteine residue of the single N-terminal kringle domain (i.e., the most C-terminal Cys residue shown in FIG. 3) and the activation site of plasminogen can be varied without departing from the scope of the present invention. One of skill in the art will be able to determine these variations (kringle 1-like binding of co aminocarboxylic acids, without substantial increase in size of the deletion mutant or introduction of potentially problematic glycosylation sites) without undue experimentation based on the disclosure herein and the references cited herein for guidance regarding kringle 1 function and structure.

It will further be appreciated that, depending on the criteria used, the exact "position" or sequence of the kringle, activation site, and serine protease domains of the recombinant plasminogen can differ slightly in particular variations within the scope of the present invention. For example, the exact location of the kringle domain relative to the activation site can vary slightly and/or the sequence N-terminal to the kringle domain can vary in length. Such variants can include, but are to limited to, deletions, insertions, inversions, repeats, and substitutions. Guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Thus, variants, fragments, derivatives or analogs of the polypeptide of SEQ ID NO:1 can be (i) ones in which one or more of the amino acid residues (e.g., 3, 5, 8, 10, 15 or 20 residues) are substituted with a conserved or non-conserved amino acid residue (preferably a conserved amino acid residue). Such substituted amino acid residues may or may not be one encoded by the genetic code, or (ii) ones in which one or more of the amino acid residues includes a substituent group (e.g., 3, 5, 8, 10, 15 or 20), or (iii) ones in which the mature polypeptide is fused with another compound, such as a compound to increase the half-life of the polypeptide (for example, polyethylene glycol), or (iv) ones in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given plasminogen polypeptide will not be more than 50, 40, 30, 25, 20, 15, 10, 5 or 3.

Amino acids in the recombinant plasminogen that are essential for function can be identified by methods known in the art, such as site-directed mutagenesis or alanine-scanning mutagenesis (Cunningham and Wells, Science 244:1081-1085 (1989)). The latter procedure introduces single alanine mutations at every residue in the molecule. The resulting mutant molecules are then tested for biological activity, e.g., as shown in the examples provided herein. Sites that are critical for ligand binding can also be determined by structural analysis such as crystallization, nuclear magnetic resonance or photoaffinity labeling (Smith, et al., J. Mol. Biol. 224:399-904 (1992) and de Vos, et al. Science 255:306-312 (1992)). Even if deletion of one or more amino acids from the N-terminus of a protein results in modification or loss of one or more biological functions of the protein, other biological activities can still be retained.

It is also contemplated that recombinant plasminogens can be produced by solid phase synthetic methods. See Houghten, R. A., Proc. Natl. Acad. Sci. USA 82:5131-5135 (1985); and U.S. Pat. No. 4,631,211 to Houghten et al. (1986).

Polypeptides having an amino acid sequence of an indicated percent identity to a reference amino acid sequence of SEQ ID NO:1 can be determined using the methods, including computer-assisted methods, indicated above regarding polynucleotides. Polypeptide amino acid sequences are examined and compared just as are the nucleotide sequences in the foregoing discussion. One of skill in the art will recognize that such concepts as the molecular endpoints discussed for polynucleotides will have direct analogs when considering the corresponding use of such methods and programs for polypeptide analysis. For example, the manual corrections discussed regarding polynucleotides refer to 5' and 3' endpoints of nucleic acids, but the same discussion will be recognized as applicable to N-termini and C-termini of polypeptides.

The invention also encompasses recombinant plasminogen polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications can be carried out by known techniques, including but not limited, to specific chemical cleavage by cyanogen bromide, trypsin, chymotrypsin, papain, S. aureus V8 protease, $NaBH_4$; acetylation, deamidation, formylation, methylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends, attachment of chemical moieties to the amino acid backbone, chemical modifications of N-linked or O-linked carbohydrate chains, and addition of an N-terminal methionine residue as a result of vectors and constructs adapted for expression of the recombinant plasminogen polypeptides, for example for expression in prokaryotic cultured host cells. In some embodiments, the recombinant plasminogen also can be modified, for example with an affinity label (e.g., His-tags, GST-tags) or a detectable label such as an enzymatic, fluorescent, or isotopic label.

D. Vectors and Host Cells

In other aspects, the present invention also relates to kits and vectors that include the recombinant plasminogen molecules of the present invention; to cultured host cells which are genetically engineered with the recombinant vectors; and to the recombinant expression of the plasminogen polypeptides by recombinant techniques. In one embodiment, the method for preparing plasminogen or a plasmin prepared therefrom comprises expressing the recombinant plasminogen using a recombinant expression system.

The origin of the host cell for protein expression is not to be limited, for example the host cell can be exemplified by microorganisms such as bacteria (e.g., those belonging to the genus Escherichia and those belonging to the genus Bacillus) and yeast (e.g., the genus Saccharomyces and the genus Pichia). For example, the genus Escherichia includes, but is not limited to, Escherichia coli (E. coli) K12DH1, M103, JA221, HB101, X600, XL-1 Blue and JM109. For example, the genus Bacillus includes, but is not limited to, Bacillus subtilis MI114 and 207-21. For example, the yeast includes, but is not limited to, Saccharomyces cerevisiae AH22, AH22R.sup.-, NA87-11A and DKD-5D and Pichia pastoris. U.S. Pat. No. 6,068,995 is herein incorporated by reference for its teaching of producing a protein by way of a host cell capable of expressing the desired protein.

For example, a molecule having the plasminogen coding sequence (e.g., SEQ ID NO:1) can be inserted into a cloning vector appropriate for expression in a host cell. The cloning vector can be constructed so as to provide the appropriate regulatory functions required for the efficient transcription, translation, and processing of the coding sequence. Suitable host cells for expressing the DNA encoding the plasminogen include prokaryote, yeast, or higher eukaryotic cells. Suitable prokaryotes include e.g., bacteria such as archaebacteria and eubacteria. Preferred bacteria are eubacteria, such as Gram-negative or Gram-positive organisms, for example, Enterobacteriaceae such as E. coli. Further, the vector can be, for example, a plasmid, a phage, a viral or retroviral vector. Retroviral vectors can be replication competent or replication defective. In the latter case, viral propagation generally will occur only in complementing cultured host cells. In one embodiment, the recombinant expression system is an E. coli-based expression system.

In addition to prokaryotes, eukaryotic microbes such as filamentous fungi or yeast also can be suitable expression hosts for plasminogen-encoding vectors. For example, Saccharomyces cerevisiae can be used. In another embodiment, the recombinant expression system is a Pichia-based expression system. However, a number of other genera, species, and strains are commonly available and useful herein.

Suitable host cells appropriate for the expression of the DNA encoding the plasminogen also can be derived from multicellular organisms. Examples of invertebrate cells include plant (e.g., from the duckweed family such as Lemna) and insect cells. Plant cell cultures of cotton, corn, potato, soybean, petunia, tomato, and tobacco also can be utilized as hosts. Regulatory and signal sequences compatible with plant cells are available. U.S. Pat. No. 6,815,184 is herein incorporated by reference for its teaching of expressing a polypeptide in duckweed.

A plasminogen expression vector can be introduced into the host cells and host cells cultured in conventional nutrient media modified as appropriate for inducing promoters, selecting transformants, or amplifying the genes encoding the desired plasminogen sequences. Numerous methods of transfection are known to the ordinarily skilled artisan, for example, calcium phosphate and electroporation. Depending on the host cell used, transformation is performed using standard techniques appropriate to such cells. For example, if prokaryotic cells are used to produce plasminogen, they can be cultured in suitable media in which the promoter can be constitutively or artificially induced as described generally, e.g., in Sambrook et al., Molecular Cloning: A Laboratory Manual (Cold Spring Harbor Laboratory Press, New York 1989). Thus, recombinant constructs can be introduced into cultured host cells using well-known techniques such as infection, transduction, transfection, transvection, electroporation and transformation.

In some embodiments, polynucleotides coding for the recombinant plasminogen can be joined to a vector containing a selectable marker for propagation in a cultured host. Preferred are vectors comprising cis-acting control regions to the polynucleotide coding the plasminogen. Appropriate trans-acting factors can be supplied by the cultured host, supplied by a complementing vector or supplied by the vector itself upon introduction into the cultured host. In some embodiments, the vectors provide for specific expression, which can be inducible and/or cell type-specific. In one embodiment, among such vectors are those inducible by environmental factors that are easy to manipulate, such as temperature and nutrient additives.

Non-limiting examples of expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

DNA inserts can be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs can include a translation initiating at the beginning and a termination codon (UAA, UGA or UAG) appropriately positioned at the end of the polypeptide to be translated.

As indicated, the expression vectors can include at least one selectable marker. Such markers include dihydrofolate reductase or neomycin resistance for eukaryotic cell culture and tetracycline or ampicillin resistance genes for culturing in E. coli and other bacteria. Non-limiting examples of appropriate cultured hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture media and conditions for the above-described cultured host cells are known in the art.

For example, in other embodiments, the recombinant expression system is a mammalian-based expression system. Mammalian cell lines available as hosts for expression are known in the art including immortalized cell lines available from the American Type Culture Collection (ATCC). Exemplary mammalian host cells include, but are not limited to, primate cell lines and rodent cell lines, including transformed cell lines. Preferably for stable integration of the vector DNA, and for subsequent amplification of the integrated vector DNA, both by conventional methods, Chinese hamster ovary (CHO) cells are employed as a mammalian host cell of choice. Other suitable cell lines include, but are not limited to, HeLa cells, baby hamster kidney (BHK) cells, monkey kidney cells (COS-1), human hepatocellular carcinoma cells (e.g., Hep G2), human adenovirus transformed 293 cells, mouse L-929 cells, HaK hamster cell lines, murine 3T3 cells derived from Swiss, Balb-c or NIH mice and a number of other cell lines. Another suitable mammalian cell line is the CV-1 cell line. Normal diploid cells, cell strains derived from in vitro culture of primary tissue, as well as primary explants, are also suitable. Candidate cells may be genotypically deficient in the selection gene, or may contain a dominantly acting selection gene.

For example, the host cells can be transformed with the one or more vectors carrying the plasminogen DNA, e.g. by methods known in the art, and can then be cultured under suitable conditions if desired, with amplification of one or both introduced genes. The expressed plasminogen can then be recovered and purified from the culture medium (or from the cell, for example if expressed intracellularly) by methods known to one of skill in the art.

Vectors suitable for replication in mammalian cells can include viral replicons, or sequences that ensure integration of the sequence encoding plasminogen into the host genome. Suitable vectors can include, for example, those derived from simian virus SV40, retroviruses, bovine papilloma virus, vaccinia virus, and adenovirus. The components of the vectors, e.g. replicons, selection genes, enhancers, promoters, and the like, may be obtained from natural sources or synthesized by known procedures.

A suitable vector, for example, can be one derived from vaccinia viruses. In this case, the heterologous DNA is inserted into the vaccinia genome. Techniques for the insertion of foreign DNA into the vaccinia virus genome are known in the art, and utilize, for example, homologous recombination. The insertion of the heterologous DNA is generally into a gene which is non-essential in nature, for example, the thymidine kinase gene (tk), which also provides a selectable marker.

Mammalian expression vectors can comprise one or more eukaryotic transcription units that are capable of expression in mammalian cells. For example, the transcription unit can comprise at least a promoter element to mediate transcription of foreign DNA sequences. Suitable promoters for mammalian cells are known in the art and include viral promoters such as that from simian virus 40 (SV40), cytomegalovirus (CMV), Rous sarcoma virus (RSV), adenovirus (ADV), and bovine papilloma virus (BPV).

The transcription unit also can comprise a termination sequence and poly(A) addition sequences operably linked to the plasminogen sequence. The transcription unit also can comprise an enhancer sequence for increasing the expression of plasminogen.

Optionally, sequences that allow for amplification of the gene also can be included, as can sequences encoding selectable markers. Selectable markers for mammalian cells are known in the art, and include for example, thymidine kinase, dihydrofolate reductase (together with methotrexate as a DHFR amplifier), aminoglycoside phosphotransferase, hygromycin B phosphotransferase, asparagine synthetase, adenosine deaminase, metallothionein, and antibiotic resistant genes such as neomycin. Or, for example, the vector DNA can comprise all or part of the bovine papilloma virus genome and be carried in cell lines such as C127 mouse cells as a stable episomal element.

In one embodiment, the recombinant plasminogen can be prepared using the PER.C6® technology (Crucell, Holland, The Netherlands). Expression of recombinant proteins is disclosed by, e.g., U.S. Pat. No. 6,855,544, which is herein incorporated by reference for its teaching of methods and compositions for the production of recombinant proteins in a human cell line.

Among vectors preferred for use in bacteria include e.g., pET24b or pET22b available from Novagen, Madison, Wis. (pET-24b(+) and pET-22b(+)=pET Expression System 24b (Cat. No. 69750) and 22b (Cat. No. 70765), respectively, EMD Biosciences, Inc., Novagen Brand, Madison, Wis.; pQE70, pQE60 and pQE-9, available from Qiagen Inc., Valencia, Calif.; pBS vectors, PHAGESCRIPT vectors, BLUESCRIPT vectors, pNH8A, pNH16a, pNH18A, pNH46A, available from Stratagene, La Jolla, Calif.; and ptrc99a, pKK223-3, pKK233-3, pDR540, pRIT5 available from Pharmacia (now Pfizer, Inc., New York, N.Y.). Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Bacterial promoters suitable for use in the present invention include the *E. coli* lacI and lacZ promoters, the T3 and T7 promoters, the gpt promoter, the lambda PR and PL promoters, and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In some embodiments, introduction of a vector construct into the cultured host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology, $2^{nd}$ Edition (1995).

Transcription of the DNA encoding the plasminogens of the present invention by higher eukaryotes can be increased by inserting an enhancer sequence into the vector. Enhancers are cis-acting elements of DNA, usually about from 10 to 300 bp that act to increase transcriptional activity of a promoter in a given cultured host cell-type. Examples of enhancers include the SV40 enhancer, which is located on the late side of the replication origin at by 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals can be incorporated into the expressed polypeptide. The signals can be endogenous to the polypeptide or they can be heterologous signals.

In various embodiments, the plasminogens can be expressed in a modified form, such as a fusion protein, and can include not only secretion signals, but also additional heterologous functional regions. For instance, a region of additional amino acids, particularly charged amino acids, can be added to the N-terminus, for example, the polypeptide to improve stability and persistence in the cultured host cell, during purification, or during subsequent handling and storage. Also, peptide moieties can be added to the polypeptide to facilitate purification. Such regions can be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP 0 464 533 A1 (Canadian counterpart, 2,045,869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties. On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery for example, human proteins have been fused with Fc portions for the purpose of high-throughput screening assays (such as hIL5-receptor, to identify antagonists of hIL-5). See, Bennett, D., et al., *J. Molecular Recognition,* 8:52-58 (1995) and Johanson, K. et al., *J. Biol. Chem.,* 270(16):9459-9471 (1995).

In one embodiment, insoluble plasminogen is isolated from the prokaryotic host cells in a suitable isolation buffer. For example, the host cells can be exposed to a buffer of suitable ionic strength to solubilize most host proteins, but in which aggregated plasminogen is substantially insoluble, and disrupting the cells so as to release the inclusion bodies and make them available for recovery by, for example, centrifugation. This technique is known to one of ordinary skill in the art, and a variation is described, for example, in U.S. Pat. No. 4,511,503, which is incorporated by reference herein for its teaching of a method of solubilizing heterologous protein, produced in an insoluble refractile form in a recombinant host cell culture. In one embodiment, the step of expressing the recombinant plasminogen comprises performing the expression system under an expression condition sufficient to produce a recombinant plasminogen inclusion body.

Without being held to a particular theory, it is believed that expression of a recombinant protein, in e.g. *E. coli,* frequently results in the intracellular deposition of the recombinant protein in insoluble aggregates called inclusion bodies. Deposition of recombinant proteins in inclusion bodies can be advantageous both because the inclusion bodies accumulate highly purified recombinant protein and because protein sequestered in inclusion bodies is protected from the action of bacterial proteases.

Generally, host cells (e.g., *E. coli* cells) are harvested after an appropriate amount of growth and suspended in a suitable buffer prior to disruption by lysis using techniques such as, for example, mechanical methods (e.g., sonic oscillator) or by chemical or enzymatic methods. Examples of chemical or enzymatic methods of cell disruption include spheroplasting, which comprises the use of lysozyme to lyse bacterial wall, and osmotic shock, which involves treatment of viable cells with a solution of high tonicity and with a cold-water wash of low tonicity to release the polypeptides.

Following host cell disruption, the suspension is typically centrifuged to pellet the inclusion bodies. The resulting pellet contains substantially all of the insoluble polypeptide fraction, but if the cell disruption process is not complete, it may also contain intact cells or broken cell fragments. Completeness of cell disruption can be assayed by resuspending the pellet in a small amount of the same buffer solution and examining the suspension with a phase-contrast microscope. The presence of broken cell fragments or whole cells indicates that additional disruption is necessary to remove the fragments or cells and the associated non-refractile polypeptides. After such further disruption, if required, the suspension can be again centrifuged and the pellet recovered, resuspended, and analyzed. The process can be repeated until visual examination reveals the absence of broken cell fragments in the pelleted material or until further treatment fails to reduce the size of the resulting pellet. Once obtained from the solubilized inclusion bodies or at a later stage of purification, the plasminogen can be suitably refolded in accordance with the present invention. The degree of any unfolding can be determined by chromatography including reversed phase-high performance liquid chromatography (RP-HPLC).

If the plasminogen is not already in soluble form before it is to be refolded, it may be solubilized by incubation in a solubilization buffer comprising chaotropic agent (e.g., urea, guanidine) and reducing agent (e.g., glutathione, DTT, cysteine) in amounts necessary to substantially solubilize the plasminogen. This incubation takes place under conditions of plasminogen concentration, incubation time, and incubation temperature that will allow solubilization of the plasminogen to occur. Measurement of the degree of solubilization of the plasminogen in the buffer can be carried out by turbidity determination, by analyzing plasminogen fractionation between the supernatant and pellet after centrifugation on reduced SDS gels, by protein assay (e.g., the Bio-Rad protein assay kit), or by high performance liquid chromatography (HPLC). In one embodiment, the method of preparing the recombinant plasminogen further comprises contacting the recombinant plasminogen inclusion body with a solubilization buffer under a solubilization condition sufficient to obtain a solubilized recombinant plasminogen inclusion body.

The pH of the solubilization buffer can be alkaline, preferably at least about pH 7.5, with the preferred range being about pH 7.5 to about pH 11. The concentration of plasminogen in the buffered solution for solubilization must be such that the plasminogen will be substantially solubilized and partially or fully reduced and denatured. Alternatively, the plasminogen may be initially insoluble. The exact amount to employ will depend, e.g., on the concentrations and types of other ingredients in the buffered solution, particularly the type and amount of reducing agent, the type and amount of chaotropic agent, and the pH of the buffer. For example, the concentration of plasminogen can be increased if the concentration of reducing agent, e.g., glutathione, is concurrently increased.

In other embodiments, the method of preparing the plasminogen further comprises contacting the solubilized recombinant plasminogen inclusion body with a refolding solution under a refolding condition to obtain a composition comprising the recombinant plasminogen. In some embodiments, it is desirable to produce a more concentrated solubilized protein solution prior to dilution refolding. For example, in one embodiment, the plasminogen is diluted with a refolding buffer, preferably at least about five fold, more preferably at least about ten to about twenty fold. In other embodiments, the plasminogen is dialyzed against the refolding buffer.

The concentration of plasminogen in the refolding buffer can be such that the ratio of correctly folded to misfolded conformer recovered will be maximized, as determined by HPLC, RIA, or bioassay. The refolding incubation is carried out to maximize the yield of correctly folded plasminogen conformer and the ratio of correctly folded plasminogen conformer to misfolded plasminogen conformer recovered, as determined by RIA or HPLC, and to minimize the yield of multimeric, associated plasminogen as determined by mass balance, for example.

In other embodiments, refolding is performed employing a high-pressure refolding technique. Thus, in some embodiments, the present invention provides a method for preparing plasminogen, wherein the method comprises refolding comprising:

(a) adjusting total protein concentration in a mixture to a first concentration of at least about 0.01 mg/ml, wherein the mixture comprises a plasminogen;

(b) subjecting the mixture to a first pressure of about 0.25 kbar to about 12 kbar for a first time and a first temperature;

(c) subjecting the mixture to a second pressure of about 0.25 kbar to about 3.3 kbar for a second time; and (d) subjecting the mixture to a third pressure, whereby the plasminogen in the mixture is disaggregated and refolded.

High pressure refolding is disclosed in, e.g., U.S. Pat. No. 7,064,192, which is incorporated by reference herein for its teaching of a method of refolding protein aggregates and inclusion bodies.

In one embodiment, the first concentration is no greater than 500 mg/ml. In another embodiment, refolding comprises: contacting the mixture with a chaotropic agent at a second concentration of no greater than 8 M. In some embodiments, the second time is about 0.1 hours to about 12 hours. In other embodiments, the third pressure is about atmospheric pressure. In particular embodiments, subjecting the mixture to the first pressure is sufficient to disaggregate the plasminogen. In various other embodiments, the mixture comprises solubilized inclusion bodies corresponding to recombinantly prepared plasminogen.

For example, overexpression of recombinant plasminogen in *E. coli* can form inclusion bodies that correspond to relatively dense, insoluble particles of aggregated plasminogen protein. In one embodiment, once isolated, the inclusion bodies can be solubilized by a variety of techniques, or a combination of pressure and chaotropic agent (and optionally, also a reducing agent). Renaturation to a biologically proper plasminogen conformation can proceed under conditions of elevated pressure, and optionally in the presence of a non-denaturing (e.g., at ambient atmospheric pressures) concentration of chaotropic agent and/or redox reagents (e.g., dithiothreitol and oxidized glutathione).

For example, pressure can be generated using high-pressure nitrogen (e.g., 400 bar) connected to a 10-fold hydraulic intensifier equipment (High Pressure Equipment Company, Erie, Pa.). Time to reach the desired pressure can be about 10 min. The nitrogen input can be connected to a 10-fold hydraulic intensifier, which can be connected to a 2-liter cloverleaf reactor rated to about 30,000 psi (2 kbar). For higher pressures, equipment can be modified for higher ratings. Samples can be prepared in heat-sealed bulbs of SAMCO™ plastic transfer pipettes (Fisher Scientific, Pittsburgh, Pa.), for example, and placed in a 2 liter clover leaf reactor rated to 2,000 bar and filled with water. Samples can be slowly pressurized (over 10 minutes) to the final desired pressure. The depressurization rate can be about 10 bar per minute.

Another embodiment of the invention employs pressure-facilitated refolding of denatured plasminogen. In this embodiment, denatured plasminogen in solution is provided in the presence of denaturing amounts of a chaotropic agent. The plasminogen concentration in solution can be about 0.001 mg/ml to about 500 mg/ml, preferably about 0.1 mg/ml to about 25 mg/ml, more preferably about 1 mg/ml to about 10 mg/ml. The chaotropic agent concentration can be about 2 M to about 8 M. The denatured plasminogen solution can be incubated at elevated pressure in the pressure range effective for facilitating renaturation, which, in some embodiments, can be about 0.25 kbar to about 3.3 kbar, preferably from about 2 kbar to about 3.3 kbar. While under pressure, the concentration of chaotropic agent can be reduced by any suitable means, for example, by dilution or by dialysis. Incubation can take place for a time sufficient to permit re-folding of the plasminogen. At the end of the pressure incubation period, the pressure can be reduced to about atmospheric pressure. In other embodiments, redox agents, stability agents, surfactants and the like can be added to the solution.

In one embodiment, the refolding composition can be subjected to one or more filtering or diafiltering steps following the step of refolding but prior to further downstream processing to eliminate or substantially reduce aggregated forms of recombinant plasminogen following the refolding step. For example, refolding mixtures can be passed through a depth filter, then diafiltrated, followed by a subsequent filtration prior to any downstream chromatography. In some embodiments, recovery of plasminogen activity through one or more sequential filtration and/or diafiltration is at least about 70%, preferably at least about 80%, 90%, or more. In one embodiment, the method for preparing the plasminogen further comprises diafiltering the composition subsequent to the step of refolding and prior to the step of contacting with the cation-exchange medium.

In other embodiments, aggregated recombinant plasminogen is selectively precipitated by adding an appropriate concentration of polyethylene glycol (PEG) or a salt of a sulfate to the refolding mixture. Under the appropriate conditions, the aggregated protein can be rendered insoluble by the added PEG or salt, and most of the correctly refolded recombinant protein can be maintained in solution. Following removal of the precipitated protein aggregates by either centrifugation or filtration, the resulting supernatant/filtrate can be further processed. For example, in one embodiment, at the completion of the refolding step, solid PEG or salt (e.g., ammonium sulfate or a nonvolatile salt of sulfate such as sodium or potassium) can be added to an appropriate concentration, and the mixture mixed to dissolve the PEG or salt and to allow the resultant precipitation of aggregated protein to proceed. Following a precipitation time, the precipitate can be removed by one or more clarification methods (e.g., depth filtration, centrifugation, microfiltration, etc., and combinations thereof), preferably by depth filtration. The resulting filtrate can then be subjected to further processing to prepare recombinant plasminogen.

Examples of PEG include, but are not limited to, PEG 200, PEG 300, PEG 400, PEG 600, PEG 1000, PEG 2000, PEG 3350, PEG 4000, PEG 4600, PEG 5000, PEG 6000, and PEG 8000. In one embodiment, a PEG is added to a refolding solution under a precipitation condition, wherein the refolding solution comprises the plasminogen and aggregated polypeptides, wherein the plasminogen is refolded plasminogen, wherein the precipitation condition is sufficient to precipitate all or a substantial portions of the aggregated proteins. In other embodiments, the PEG is added to achieve final concentrations of PEG of at least about 1% (w/v), illustratively, about 1, 2, 3, 4, 5, 6, 7, 8, 9, 10, 11, 12, 13, 14, 15, 16, 17, 18, 19, and 20% (w/v). In some embodiments, a first PEG precipitation is performed and at least one further PEG precipitation.

In other embodiments, ammonium sulfate (e.g., solid ammonium sulfate) is added to the refolding solution to achieve final concentrations of ammonium sulfate corresponding to at least about 1% saturation, illustratively, at least about 1, 5, 10, 15, 20, 25, 30, 35, 40, 45, 50, 55, 60, and 70%.

In one embodiment, the resulting filtrate (following PEG or salt precipitation) can be contacted with a suitable hydrophobic interaction chromatography medium under a suitable hydrophobic interaction condition sufficient such that the hydrophobic interaction chromatography medium preferentially captures the plasminogen. The hydrophobic interaction medium can be a solid phase that binds the plasminogen. The hydrophobic interaction chromatography medium can be selected from any of the group of chromatography media commonly described as hydrophobic interaction media. The medium can possess a chemistry or a ligand coupled thereto that can allow for selective or preferential capture of the plasminogen. Useful chromatography media comprise a support and one or more ligand(s) bound thereto that provide(s) the selective or preferential binding capability for the plasminogen. Useful supports include, by way of illustrative example, polysaccharides such as agarose and cellulose, organic polymers such as polyacrylamide, methylmethacrylate, and polystyrene-divinylbenzene copolymers. It should be recognized that it is not intended herein to imply that only organic substrates are suitable for medium substrate use, since inorganic support materials such as silica and glasses also can be used.

In some embodiments, the hydrophobic interaction medium is in the form of beads, which can be generally spherical, or alternatively the second affinity medium can be usefully provided in particulate or divided forms having other regular shapes or irregular shapes. In one embodiment, the medium is in the form of a membrane. The hydrophobic interaction medium can be of porous or nonporous character, and the medium can be compressible or incompressible. Preferred hydrophobic interaction media will be physically and chemically resilient to the conditions employed in the purification process. A wide variety of hydrophobic interaction media, for example, those wherein the coupled ligand is a phenyl, octyl, or butyl moiety, are known in the art.

In one embodiment, the hydrophobic interaction medium comprises a ligand coupled to a support, wherein the ligand is a phenyl moiety, wherein the support is an agarose. For example, hydrophobic interaction chromatography can be performed in a phenyl-Sepharose™ column format.

In some embodiments, following removal of the precipitated plasminogen aggregates by either centrifugation or filtration, the resulting supernatant/filtrate comprising the correctly refolded recombinant plasminogen, optionally, is captured and purified directly by hydrophobic interaction chromatography.

If desired, the use of selective precipitation and/or hydrophobic interaction chromatography can, but need not, replace the one or more filtering/diafiltering steps of the refolding mixture thereby providing an alternative approach to purification of the recombinant protein.

In some embodiments, following the step(s) of subjecting the refolding mixture to one or more filtering/diafiltering steps and/or a selective precipitation steps and/or hydrophobic interaction chromatography, the resulting solution comprising the recombinant plasminogen can be further purified by contacting the resulting solution with the cation-exchange medium (e.g., SP-SEPHAROSE™) and/or the first affinity medium (e.g., ECH-Lysine column).

Following one or more preparation steps in accordance with the present invention, the plasminogen thus prepared can be activated to obtain plasmin or stored at a suitable temperature (e.g., −20° C., −80° C.) prior to activation of the plasminogen.

Thus, in particular embodiments, the present invention provides a method for preparing plasminogen, the method comprising:
(a) expressing a recombinant plasminogen using a recombinant expression system under an expression condition;
(b) contacting the recombinant plasminogen with a solubilization buffer under a solubilization condition sufficient to obtain a solubilized recombinant plasminogen;

(c) contacting the solubilized recombinant plasminogen with a refolding solution under a refolding condition to obtain a composition comprising the recombinant plasminogen;

(d) diafiltering the composition subsequent to step (c);

(e) contacting the composition with a cation-exchange medium under an ion-exchange condition that is sufficient for the cation-exchange medium to bind the recombinant plasminogen;

(f) eluting the recombinant plasminogen captured by the cation-exchange medium to obtain a cation-exchange medium eluate comprising the recombinant plasminogen;

(g) contacting the cation-exchange medium eluate with a first affinity medium under a first affinity condition that is sufficient for the first affinity medium to bind the recombinant plasminogen; and (h) eluting the recombinant plasminogen bound by the first affinity medium to obtain a plasminogen solution comprising the recombinant plasminogen.

In one embodiment, the expression condition is sufficient to provide a recombinant plasminogen inclusion body. In some embodiments, the recombinant plasminogen inclusion body can be contacted with a solubilization buffer under a solubilization condition sufficient to obtain a solubilized recombinant plasminogen inclusion body. In other embodiments, the solubilized recombinant plasminogen inclusion body can be contacted with a refolding solution under a refolding condition to obtain a composition comprising the recombinant plasminogen.

II. Plasmin

In other aspects, the present invention provides a method for preparing plasmin. In one embodiment, the method comprises contacting a plasmin composition with an affinity medium (e.g., benzamidine-SEPHAROSE™), wherein the plasmin composition comprises plasmin prepared by activating a plasminogen with a plasminogen activator. In some embodiments, the plasminogen is prepared in accordance with the present invention. In one embodiment, the plasminogen is a recombinant plasminogen prepared in accordance with the present invention.

A. Converting Plasminogen to Plasmin

In some embodiments, the method for preparing plasmin comprises contacting the plasminogen with a plasminogen activator in an activation solution under an activation condition sufficient to convert the plasminogen to a plasmin.

Generally, the plasminogen can be activated (i.e., cleaved to provide plasmin) using a catalytic concentration of a plasminogen activator (e.g., streptokinase, urokinase, tPA, trypsin), which can be soluble and/or immobilized. In some embodiments, the activation of the plasminogen can occur at about 4° C. or more, e.g., about 4, 10, 20, 25, 37 or more degrees celsius and typically can take at least several minutes or more, preferably at least about 1, 2, 4, or more hours. The plasminogen can be cleaved in the presence of one or more reagents including stabilizers and/or excipients such as omega-amino acids, salts, sucrose, alcohols (e.g., ethanol, methanol, 1,2-propanediol, 1,3-propanediol, glycerol, ethylene glycol), and combinations thereof. The omega-amino acids can include lysine, epsilon amino caproic acid (∈-ACA), tranexamic acid, poly-lysine, arginine and combinations or analogues thereof. Stabilizing agents are described by, e.g., U.S. Patent Publication No. 20030012778, which is herein incorporated by reference in its entirety.

In one embodiment, the plasminogen activator is a soluble plasminogen activator. In another embodiment, the method for preparing plasmin comprises contacting the plasminogen with a plasminogen activator in an activation solution under an activation condition sufficient to convert the plasminogen to a plasmin, wherein the plasminogen activator is an immobilized plasminogen activator.

For example, the plasminogen activator can be adsorbed onto a suitable matrix. For example, it has been reported that streptokinase is still capable of activating plasminogen to plasmin when streptokinase is bound tightly to nitrocellulose (Kulisek et al., Anal. Biochem. 177:78-84 (1989)). Also, adsorption of streptokinase to a suitable ion-exchange resin can render it immobilized and still capable of activating plasminogen.

Immobilized streptokinase also is discussed by Rimon et al., Biochem. Biophy. Acta 73:301 (1963) using a diazotized copolymer of p-aminophenylalanine and leucine. These authors utilized the immobilized streptokinase to study the mechanism of activation of plasminogen. Sugitachi et al., Thromb. Haemost. (Stuttg.) 39:426 (1978) discuss the immobilization of the plasminogen activator, urokinase, on nylon. U.S. Pat. No. 4,305,926, incorporated herein by reference for its teaching of immobilized plasminogen activator, proposes immobilization of streptokinase onto a biocompatible polymer such as a nylon, Dacron, collagen, polyvinylpyrrolidine, or copolymeric p-aminophenylalanine and leucine.

In one embodiment, the streptokinase is immobilized on a surface using an affinity tag as described in U.S. Pat. No. 6,406,921, which is incorporated herein by reference for its teaching of immobilizing streptokinase. The surface can be either organic or inorganic, biological or non-biological, or any combination of these materials. In one embodiment, the surface is transparent or translucent. Numerous materials are suitable for use as a surface. For example, the surface can comprise a material selected from a group consisting of silicon, silica, quartz, glass, controlled pore glass, carbon, alumina, titanium dioxide, germanium, silicon nitride, zeolites, and gallium arsenide. Many metals such as gold, platinum, aluminum, copper, titanium, and their alloys are also options for surfaces. In addition, many ceramics and polymers can also be used. Polymers which may be used as surfaces include, but are not limited to, the following: polystyrene; poly(tetra)fluorethylene; (poly)vinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PMI); polyalkenesulfone (PAS); polyhydroxyethylmethacrylate; polydimethylsiloxane; polyacrylamide; polyimide; co-block-polymers; and Eupergit™ Photoresists, polymerized Langmuir-Blodgett films, and LIGA structures may also serve as surfaces in the present invention.

In some embodiments, the activation condition is sufficient to convert all or a substantial amount of the plasminogen to a plasmin thereby providing a composition comprising the plasmin.

B. Anion-Exchange Chromatography

In other aspects, the present invention provides a method for preparing a plasmin. The method comprises: contacting a composition comprising the plasmin with an anion exchanger whereby, if present in the composition, a proteinaceous material having an isoelectric point below that of the plasmin is separated from the plasmin.

Without being held to any particular theory, it is believed that for any one proteinaceous material there will be a pH at which the overall number of negative charges equals the number of positive charges. This is the protein's isoelectric point (or pI), i.e., the pH at which the protein carries no net charge. Above its pI, the protein will have a net negative charge and bind to an anion exchanger.

In a preferred embodiment, the plasmin that is present in the composition is a product of a plasminogen having been activated by a plasminogen activator. For example, a recombinant plasminogen or a blood-derived plasminogen can be contacted with a plasminogen activator (e.g., a streptokinase) to provide the plasmin. In one embodiment, the composition comprising the plasmin is an activation solution that has been pH-adjusted, if necessary, prior to contacting with the anion exchanger.

In another embodiment, the composition comprising the plasmin is an eluate or a flow-through solution of a chromatography step (e.g., affinity chromatography using benzamidine), wherein the eluate or flow-through solution has been pH-adjusted, if necessary, prior to contacting with the anion exchanger.

The proteinaceous material to be separated from the plasmin has a pI below that of the plasmin's pI. In some embodiments, the proteinaceous material is the plasminogen activator (e.g., streptokinase) or a fragment thereof, wherein the composition comprising the plasmin is contacted with an anion-exchange medium under an anion-exchange condition sufficient to obtain an anion-exchanger flow-through comprising the plasmin, wherein the anion-exchange condition is such that the anion-exchange medium selectively or preferentially binds the plasminogen activator or a fragment thereof relative to the plasmin.

Without being held to any particular theory, it is believed that proteolysis of streptokinase as a consequence of its activation of plasminogen occurs following streptokinase contact with plasminogen. In addition to the formation of plasmin, streptokinase fragments of varying molecular weights can form upon activation of the plasminogen by the streptokinase.

In one embodiment, the proteinaceous material is a streptokinase fragment having a molecular weight of less than about 45 kD as determined by gel electrophoresis under denaturing conditions, for example. In another embodiment, the fragment has a molecular weight of about 40, 25, 15, 10 kD or less. In some embodiments, the fragment has a molecular weight of about 15 kD.

In one embodiment, prior to the contacting of the composition comprising the plasmin with the anion exchanger, the pH of the composition is adjusted to be less than the pI of the plasmin but greater than the pI of the proteinaceous material to be separated from the plasmin. In some embodiments, the pH of the composition is adjusted to be about 5.0 to about 10.0, illustratively, about: 10, 9.9, 9.8, 9.7, 9.6, 9.5, 9.4, 9.3, 9.2, 9.1, 9, 8.9, 8.8, 8.7, 8.6, 8.5, 8.4, 8.3, 8.2, 8.1, 8, 7.9, 7.8, 7.7, 7.6, 7.5, 7.4, 7.3, 7.2, 7.1, 7, 6.9, 6.8, 6.7, 6.6, 6.5, 6.4, 6.3, 6.2, 6.1, 6, 5.9, 5.8, 5.7, 5.6, 5.5, 5.4, 5.3, 5.2, 5.1, and 5. In another embodiment, the pH of the composition is adjusted to be about 6.5 to about 7. In other embodiments, the pH of the composition is adjusted to be about 7 to about 8. In still further embodiments, the pH of the composition is adjusted to be about 6.5 to about 8.

In various embodiments, the proteinaceous material is a plasminogen activator or a fragment thereof. In one embodiment, the composition comprising the plasmin is an activation solution in which a plasminogen is converted by a plasminogen activator to form the plasmin. In some embodiments, the activation solution (comprising the plasmin formed therein) is directly contacted with the anion exchanger, wherein prior to the contacting, the activation solution is pH-adjusted, if necessary. In another embodiment, prior to contacting the activation solution with the exchanger, the activation solution is subjected to one or more plasmin purification steps such as, but not limited to, filtration, affinity chromatography, ion exchange chromatography, and/or hydrophobic interaction chromatography. Accordingly, in some embodiments, an eluate or flow-through composition obtained from the one or more plasmin purification steps can be contacted with the anion exchanger following an appropriate pH adjustment of the eluate or the flow-through composition, if necessary.

For example, in one embodiment, wherein the plasmin comprises a pI of about 9 or greater, wherein the material to be separated is a streptokinase fragment (e.g., a fragment having a molecular weight of about 15 kD or less) having a pI of about 5, the pH of the composition can be adjusted to be about 6 to about 8 to effect binding of the fragment (i.e., the material), but not the plasmin, to the exchanger.

By way of another example, in other embodiments, wherein the plasmin comprises a pI of about 7 to about 8, wherein the material to be separated is a streptokinase fragment (e.g., a fragment having a molecular weight of about 15 kD or less) having a pI of about 5, the pH of the composition can be adjusted to be about 6 to about 7 to effect binding of the fragment (i.e., the material), but not the plasmin, to the exchanger.

In some embodiments, the methods may be carried out in batch or as continuous processes.

In other embodiments, the flow-through solution obtained from the anion exchanger can be subjected to further processing including further purification of the plasmin contained therein and/or reduction of any pathogens that may be contaminating the plasmin. In some embodiments, further purification is effected by additional filtration steps (e.g., nanofiltration) and/or chromatography steps including, but not limited to, affinity chromatography, ion exchange chromatography, and hydrophobic interaction chromatography.

In some embodiments, the method for preparing plasmin comprises contacting the activation solution with an anion-exchange medium under an anion-exchange condition to obtain an anion-exchanger flow-through comprising the plasmin, wherein the anion-exchange condition is such that the anion-exchange medium selectively or preferentially binds the plasminogen activator relative to the plasmin.

The anion-exchange medium can be a solid phase that binds the plasminogen activator present in the activation solution. The anion-exchange chromatography medium can be selected from any of the group of chromatography media commonly described as anion-exchange media, preferably a strong anion exchanger. The medium can possess a chemistry or a ligand coupled thereto that can allow for selective or preferential capture of the plasminogen activator from the activation solution. Useful chromatography media comprise a support and one or more ligand(s) bound thereto that provide(s) the selective or preferential binding capability for the plasminogen activator. Useful supports include, by way of illustrative example, polysaccharides such as agarose and cellulose, organic polymers such as polyacrylamide, methylmethacrylate, and polystyrene-divinylbenzene copolymers. It should be recognized that it is not intended herein to imply that only organic substrates are suitable for medium substrate use, since inorganic support materials such as silica and glasses also can be used.

In some embodiments, the anion-exchange medium is in the form of beads, which can be generally spherical, or alternatively the anion-exchange medium can be usefully provided in particulate or divided forms having other regular shapes or irregular shapes. In one embodiment, the medium is in the form of a membrane. The anion-exchange medium can be of porous or nonporous character, and the medium can be compressible or incompressible. Preferred anion-exchange media will be physically and chemically resilient to the conditions employed in the purification process including pumping and cross-flow filtration, and temperatures, pH, and other aspects of the various compositions employed. A wide variety of anion-exchange media, for example, those wherein the coupled ligand is quaternaryammonium (Q) or qauternaryaminoethyl (QAE), are known in the art.

In one embodiment, the anion-exchange medium comprises a ligand coupled to a support, wherein the ligand is quaternaryammonium, wherein the support is a membrane. For example, anion-exchange chromatography can be performed in a Q-membrane or Q-Sepharose™ column format. In one embodiment, the anion-exchanger is a Q-membrane.

In other embodiments, the anion-exchange medium comprises a ligand coupled to a support, wherein the ligand is quaternary amine or ammonium, wherein the support is a membrane. For example, anion-exchange chromatography can be performed in a Q-membrane or Q-Sepharose™ column format. In one embodiment, the anion-exchanger is a Q-membrane. Commercially available anion exchange membrane adsorbers include Sartorius Sartobind® Q (Sarorius, Bohemia, N.Y.), Mustang® Q Port (Pall Corporation, Washington, N.Y.), and ChromaSorb™ (Millipore, Billerica, Mass.). In another embodiment, the anion exchanger is a Sartobind® MA 5 Q membrane.

In other embodiments, the flow-through solution obtained from the anion exchanger comprises an amount of the plasminogen activator or fragment thereof that is less than the amount of that which was present in the composition prior to contacting with the anion exchanger. In one embodiment, the resulting plasmin composition is substantially free of the proteinaceous material having a pI less than the pI of the plasmin.

In some embodiments, the plasmin that is present in the flow-through solution of the anion exchanger will typically have a purity of at least about 50% (by weight), illustratively, at least about: 50%, 60%, 70%, 80%, 90%, 95%, 99%, or greater.

In other embodiments, the flow-through solution of the anion exchanger is substantially free of the proteinaceous material, wherein the substantially free of the proteinaceous material is characterized as levels of the proteinaceous material that are below limits of detection by a Western blot.

In another embodiment, at least about 50%, illustratively, at least about: 50%, 60%, 70%, 80%, 90%, 95%, 99%, or greater of a streptokinase fragment is removed from the plasmin-containing composition that is loaded onto the anion exchanger thereby providing a resulting plasmin composition substantially free of the fragment. In some embodiments, the streptokinase fragment has a molecular weight (e.g., as determined by SDS-PAGE) of about 15 kD or less).

In one embodiment, the flow-through from the anion exchanger can be pH-adjusted, e.g. to an acidic pH (e.g., about 3.4). In some embodiments, this pH-adjusted flow-through comprising the plasmin can be subsequently concentrated and/or diafiltered by ultrafiltration/diafiltration.

By way of another example, the anion exchange flow-through can be dialyzed with water and acidified with glacial acetic acid. In some embodiments, any acid providing a pharmaceutically acceptable acidified carrier (e.g., having a low buffering capacity buffer and having a pH between about 2.5 to about 4.0) can be used. For example, also contemplated within the scope of this invention is the use of other acids and amino acids such as, but not limited to, inorganic acids, carboxylic acids, aliphatic acids and amino acids including, but not limited to, formic acid, acetic acid, citric acid, lactic acid, malic acid, tartaric acid, benzoic acid, serine, threonine, valine, glycine, glutamine, isoleucine, β-alanine and derivatives thereof, either singly or any combination thereof, that will maintain the pH in the pharmaceutically acceptable carrier of about 2.5 to about 4.0.

C. Affinity Chromatography

A plasmin composition comprising plasmin can be purified by affinity chromatography using an affinity medium that binds the plasmin contained in the composition. For example, in some embodiments, the anion-exchange medium flow-through is contacted with a second affinity medium under a second affinity condition sufficient to bind the plasmin contained in the flow-through. In particular embodiments, the second affinity condition is such that the affinity medium selectively or preferentially binds the plasmin relative to the plasminogen activator that may be present.

The second affinity medium can be a solid phase that binds the plasmin. The second affinity chromatography medium can be selected from any of the group of chromatography media commonly described as second affinity media. The medium can possess a chemistry or a ligand coupled thereto that can allow for selective or preferential capture of the plasminogen activator from the activation solution. Useful chromatography media comprise a support and one or more ligand(s) bound thereto that provide(s) the selective or preferential binding capability for the plasminogen activator. Useful supports include, by way of illustrative example, polysaccharides such as agarose and cellulose, organic polymers such as polyacrylamide, methylmethacrylate, and polystyrene-divinylbenzene copolymers. It should be recognized that it is not intended herein to imply that only organic substrates are suitable for medium substrate use, since inorganic support materials such as silica and glasses also can be used.

In some embodiments, the second affinity medium is in the form of beads, which can be generally spherical, or alternatively the second affinity medium can be usefully provided in particulate or divided forms having other regular shapes or irregular shapes. In one embodiment, the medium is in the form of a membrane. The second affinity medium can be of porous or nonporous character, and the medium can be compressible or incompressible. Preferred second affinity media will be physically and chemically resilient to the conditions employed in the purification process including pumping and cross-flow filtration, and temperatures, pH, and other aspects of the various compositions employed. A wide variety of second affinity media, for example, those wherein the coupled ligand is benzamidine, are known in the art.

In one embodiment, the second affinity medium comprises a ligand coupled to a support, wherein the ligand is benzamidine, wherein the support is agarose. For example, second affinity chromatography in accordance with the present invention can be carried out using benzamidine-Sepharose™ column format. Because the plasmin that is formed is a serine protease, in other embodiments, other affinity-type media having similar properties as benzamidine (e.g., a serine protease adsorbent material) also can be used.

For example, in other embodiments, the plasmin obtained from the cleaved plasminogen can be contained in a solution comprising one or more reagents (e.g., amino acids, sodium chloride, glycerol) that allow for stability of the solution for several days at neutral pH before the solution is applied to a benzamidine-SEPHAROSE™ column. The flow-through pool can contain both non-activated plasminogen and inactive auto-degradation products of plasmin.

Plasmin bound by an affinity medium can be eluted with an acid buffer or with a substantially neutral pH excipient solution. For example, the plasmin bound to benzamidine-SEPHAROSE® can be eluted with an acidic buffer such as glycine buffer. When a substantially neutral pH excipient solution is used to elute the bound plasmin, the final eluted plasmin solution can be substantially free of degraded plasmin. Typically, the substantially neutral pH excipient solution has a pH of value of between about 6.5 to about 8.5. However, the pH of the solution can range from about 2.5 to about 9.0. In particular embodiments, the pH can be from about 3.0 to about 7.5. In other embodiments, the pH can be about 6.0. Examples of excipients include omega-amino acids, including lysine, epsilon amino caproic acid, tranexamic acid, polylysine, arginine, and analogues and combinations thereof, salts such as sodium chloride, and active site inhibitors such as bezamidine.

An appropriate concentration of salt can be represented by a conductivity from about 5 mS/cm to about 100 mS/cm. Generally, the salt concentration can be varied somewhat inversely in relation to acidity, i.e. lower pH solutions can work well with lower salt and solutions having higher pH (within the ranges discussed above) can work well with higher salt concentrations. When the salt is sodium chloride, the concentration can be from about 50 mM to about 1000 mM, or from about 100 mM to about 200 mM. When the solution is at about pH 6.0, the concentration of sodium chloride can be about 150 mM. Thus, in some embodiments, upon the completion of the activation of the recombinant plasminogen, the plasmin composition can be filtered and further stabilized for several days at neutral pH by the addition of excipients such as omega-amino acids and sodium chloride prior to benzamidine-SEPHAROSE™ chromatography.

In some embodiments, eluted plasmin can be buffered with a low pH, low buffering capacity agent. The low pH, low buffering capacity agent typically comprises a buffer of either an amino acid, a derivative of at least one amino acid, an oligopeptide which includes at least one amino acid, or a combination of the above. Additionally the low pH, low buffering capacity agent can comprise a buffer selected from acetic acid, citric acid, hydrochloric acid, carboxcylic acid, lactic acid, malic acid, tartaric acid, benzoic acid, serine, threonine, methionine, glutamine, alanine, glycine, isoleucine, valine, alanine, aspartic acid, derivatives or combinations thereof. The buffer can be present at a concentration such that the pH of the acidified plasmin can be raised to neutral pH by adding serum to the composition in an amount no more than about 4 to 5 times the volume of acidified plasmin.

In other embodiments, the concentration of plasmin in the buffered solution can range from about 0.01 mg/ml to about 50 mg/ml of the total solution. The concentration of the buffer can range from about 1 nM to about 50 mM. Of course, these ranges may be broadened or narrowed depending upon the buffer chosen, or upon the addition of other reagents such as additives or stabilizing agents. The amount of buffer added is typically that which will bring the acidified plasmin solution to have a pH between about 2.5 to about 4.

The acidified plasmin solution may be further stabilized by the addition of a stabilizing agent such as a polyhydric alcohol, pharmaceutically acceptable carbohydrates, salts, glucosamine, thiamine, niacinamide, or combinations thereof. The stabilizing salts can be selected from the group consisting of sodium chloride, potassium chloride, magnesium chloride, calcium chloride and combinations thereof. Sugars or sugar alcohols may also be added, such as glucose, maltose, mannitol, sorbitol, sucrose, lactose, trehalose, and combinations thereof.

Concentrations of carbohydrate added to stabilize the acidified plasmin solution include a range from about 0.2% w/v to about 20% w/v. Ranges for a salt, glucosamine, thiamine, niacinamide and their combinations can range from about 0.01 M to about 1 M.

Plasmin formulated according to the invention in buffered acidified water has been found to be extremely stable. It can be kept in this form for months without substantial loss of activity or the appearance of degradation products of a proteolytic or acidic nature. At 4° C., plasmin is stable for at least nine months. Even at room temperature, plasmin is stable for at least two months. Long-term stability at room temperature can allow this formulation to be compatible with long regimens of thrombolytic administration. For example, 36 hours administration of thrombolytics such as tissue plasminogen activator or urokinase is common in treatment of peripheral arterial occlusions.

In a preferred embodiment, the plasmin contained in the acidified plasmin solution is a reversibly inactive plasmin. The ability of a buffered acidified plasmin to become fully active upon transfer to physiological pH is evidenced by its activity in the caseinolytic assay and also in the $I^{125}$-fibrin-labelled clot lysis assays. Both of these assays can be performed at pH 7.4, and there can be complete recovery of recombinant plasmin activity during the change of pH and passing through the isoelectric points (pH9.3 and 9.5). This is because recombinant plasmin is formulated in a low buffering capacity solvent and when added to a buffered solution (e.g., PBS, plasma) it can adopt the neutral pH instantly and the precipitation that usually accompanies the slow passage through the isoelectric point, does not occur.

D. Hydrophobic Interaction Chromatography

In some embodiments, the method for preparing plasmin can further comprise hydrophobic interaction chromatography. In one embodiment, hydrophobic chromatography is optional. In other embodiments, the method for preparing plasmin comprises contacting the second affinity medium eluate comprising the plasmin with a hydrophobic interaction chromatography medium under a hydrophobic interaction condition sufficient such that the hydrophobic interaction chromatography medium preferentially binds the plasminogen activator relative to the plasmin. In particular embodiments, the hydrophobic interaction condition is such that the hydrophobic interaction medium selectively or preferentially binds the plasminogen activator, if present, relative to the plasmin.

The hydrophobic interaction medium can be a solid phase that binds the plasmin. The hydrophobic interaction chromatography medium can be selected from any of the group of chromatography media commonly described as hydrophobic interaction media. The medium can possess a chemistry or a ligand coupled thereto that can allow for selective or preferential capture of the plasminogen activator. Useful chromatography media comprise a support and one or more ligand(s) bound thereto that provide(s) the selective or preferential binding capability for the plasminogen activator. Useful supports include, by way of illustrative example, polysaccharides such as agarose and cellulose, organic polymers such as polyacrylamide, methylmethacrylate, and polystyrene-divinylbenzene copolymers. It should be recognized that it is not intended herein to imply that only organic substrates are suitable for medium substrate use, since inorganic support materials such as silica and glasses also can be used.

In some embodiments, the hydrophobic interaction medium is in the form of beads, which can be generally spherical, or alternatively the second affinity medium can be usefully provided in particulate or divided forms having other regular shapes or irregular shapes. In one embodiment, the medium is in the form of a membrane. The hydrophobic interaction medium can be of porous or nonporous character, and the medium can be compressible or incompressible. Preferred hydrophobic interaction media will be physically and chemically resilient to the conditions employed in the purification process. A wide variety of hydrophobic interaction media, for example, those wherein the coupled ligand is an octyl, phenyl, or butyl moiety, are known in the art.

In one embodiment, the hydrophobic interaction medium comprises a ligand coupled to a support, wherein the ligand is an octyl moiety, wherein the support is an agarose. For example, hydrophobic interaction chromatography can be performed in an octyl-SEPHAROSE™ column format. In particular embodiments, the composition comprising the plasmin is prepared to about 0.1 M in ammonium sulfate and subjected to hydrophobic interaction chromatography, e.g. in a column format using a resin such as octyl-SEPHAROSE™.

In one embodiment, the octyl-SEPHAROSE™ flow-through comprising plasmin can be subjected to nanofiltration. For example, the flow-through can be subjected to pre-filtration with a 0.1 micron filter capsule, and then subjected to nanofiltration, e.g. using an ASAHI NF (normal flow) 1.0 $m^2$ 15N membrane (PLANOVA filters, Asahi Kasei America, Inc., Buffalo Grove, Ill.). Implementing nanofiltration further downstream in the process, after octyl hydrophobic interaction chromatography, can improve throughput and membrane flux properties due to a more pure feedstream. In some embodiment, the step of nanofiltration subsequent to hydrophobic interaction chromatography is optional.

III. Therapeutics and Kits

In other aspects, the plasminogens and/or the plasmins prepared therefrom can be formulated for therapeutic use, for example in accordance with the methods described in U.S. Pat. No. 6,964,764; and Novokhatny, V., et al., *J. Thromb. Haemost.* 1(5):1034-41 (2003), both incorporated herein by reference. For example, a low-pH (from about 2.5 to about 4), low-buffering capacity buffer can be used for formulation of plasmin prepared in accordance with the present invention. In some embodiments, the plasminogen and/or the plasmin prepared therefrom can be used to treat a variety of thrombotic diseases or conditions, for example, according to the methods as described in U.S. Pat. Nos. 6,355,243 and 6,969,515, each incorporated herein by reference for its teaching of treatment methods. Additionally, other methods and formulations known to those of skill in the art, as practiced with plasmin, mini-plasmin, and/or micro-plasmin, can be used to formulate the plasminogen and/or the plasmin prepared therefrom of the present invention for therapeutic administration.

In still further aspects, the present invention provides kits comprising the recombinant plasminogens and/or the plasmins prepared therefrom described herein. Such kits can generally comprise, in one or more separate compartments, a pharmaceutically acceptable formulation of the plasminogen and/or the plasmin prepared therefrom. The kits also can further comprise other pharmaceutically acceptable formulations. The kits can have a single container, or they may have distinct container for each desired component. Kits comprising reagents necessary for preparing the recombinant plasminogens and/or the plasmins derived therefrom also are contemplated, for example reagents such as, but not limited to, expression vectors, recombinant host cells comprising the expression vectors, and plasminogen activators. Further, wherein the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided.

The following examples are given only to illustrate the present process and are not given to limit the invention. One skilled in the art will appreciate that the examples given only illustrate that which is claimed and that the present invention is only limited in scope by the appended claims.

EXAMPLES

Example 1

Preparing Recombinant Plasminogen

An expression vector comprising the DNA encoding the recombinant plasminogen polypeptide shown in SEQ ID NO:1 (see also shaded amino acid sequence shown in FIG. 2) was transformed into a variety of cells including BL21(DE3) RIL (Stratagene, La Jolla, Calif.), BL21(DE3) (genotype: F$^-$ompT hsdS$_B$ (r$_B^-$m$_B^-$) gal dcm (DE3)) (EMB Biosciences, Inc., San Diego, Calif.), and BLR(DE3) (genotype: F$^-$ompT hsdS$_B$ (r$_B^-$m$_B^-$) gal dcm (DE3) Δ(srl-recA)306::Tn10(Tet$^R$)), and protein over-expression following induction by 1 mM IPTG (isopropyl-beta-D-thiogalactopyranoside) was analyzed by SDS-PAGE. Expression estimates were at least about 250 mg/L cell culture in shaker flasks.

Cell type BL21(DE3) RIL is engineered to express rare *E. coli* tRNAs coding for Arg, Ile, and Leu. Further, both BL21 (DE3) and BLR(DE3) are B strain *E. coli* that is classified as non-pathogenic to humans and animals based on the absence of virulence and colonization factors. BLR(DE3) cells lack the recA gene for DNA recombination, and induction of lamba phage has not been reported with these cells. A research cell bank of the recombinant plasminogen construct in BLR(DE3) cells was produced and tested for purity, identity, and induction of bacteriophage at Charles River Laboratories (Malvern, Pa.). The testing confirmed the identity and purity of the research cell bank and the cells passed the phage induction test with no phage observed (data not shown).

Production of recombinant plasminogen (i.e., based on SEQ ID NO:1) was confirmed in larger scale expression in which cells were lysed and both soluble protein and purified inclusion bodies were examined by SDS-PAGE.

The following typical protocol has been used for expression of recombinant plasminogen:

A single colony of *E. coli* cells (e.g., BL21(DE3) RIL, BL21(DE3), or BLR(DE3) containing the recombinant plasminogen vector was used to inoculate 5 ml of LB/kanamycin (30 µg/ml) and was incubated for 8 hours at 37° C. on a shaker. After that, a 50 µl-aliquot was taken form the cultured bacterial suspension for further growth in fresh media. The procedure was repeated after 16 hours with 6 ml of bacterial culture and 250 ml of the media. Cultures were grown at 37° C. with shaking to an OD600 nm of ~1.0, and IPTG was added to 1 mM final concentration. Cultures were grown for an additional 5 hours. Cells were harvested by centrifugation at 5,000×g and cell pellets were dissolved in 20 mM Tris pH 8.0 containing 20 mM EDTA and frozen at −80° C.

To purify recombinant plasminogen, cell pellets were thawed and buffer added until the solution volume was approximately ½0th that of the original cell culture volume. After that, lysozyme was added to a final concentration of 0.5 mg/ml and the cells were stirred rapidly at 4° C. for 10-15 minute. Then, Triton X-100 was added to 1% final concentration and stirring continued for another 10 min. DNAse I (0.05 mg/ml) and MgCl$_2$ (2.5 mM) were added and stirring was continued at 4° C. for 30 minutes or until the solution was no longer viscous. The final solution was centrifuged at 4° C. for 30 min at 15,000×g and the supernatant was discarded. The cell pellet was washed three times with wash solution (50 mM Tris-HCl, pH 7.4 containing 10 mM EDTA, 1% Triton-X-100, and 0.5 M urea)

The recombinant plasminogen comprises the amino acid sequence shown in FIG. 1. The primary structure of the recombinant plasminogen begins at $Met_{69}$ and has the linker sequence VPQ in place of ILE at positions 160-162 (human plasminogen numbering system); the latter change was incorporated to make the linker region joining the kringle to the serine protease domain identical to that of the native kringle 5-serine protease sequence. The N-terminal sequence of the recombinant plasminogen yields N-termini of $Lys_{78}$ and $Val_{79}$ after activation by SK and cleavage of the pre-activation peptide. The mean yield of inclusion bodies isolated from 100 L of culture was 2.17±0.63 kg (n=3), which contained approximately 20% recombinant plasminogen protein by weight.

Example 2

Solubilizing and Refolding of Plasminogen

Crushed, frozen inclusion bodies (26 g) were added to 480 ml of cold solubilization buffer (7 M urea, 10 mM reduced glutathione, 10 mM Tris, 0.25 M arginine, 2 mM EDTA, pH 7.5), and this suspension was stirred vigorously at 6° C. for 4 hr. This solution of solubilized inclusion bodies was then diluted 1:20 into cold refolding buffer [0.5 M urea, 1.0 mM each of reduced and oxidized glutathione, 0.5 M arginine, 1.0 mM EDTA, 5.0 mM ε-ACA, 50 mM Tris, pH 8.0] and stirred for 17 hr in the cold. The recombinant plasminogen concentration in this refolding milieu was approximately 0.5 mg/ml.

Solubilized inclusion bodies were analyzed by reducing SDS-PAGE; based upon densitometric analysis of Coomassie Blue-stained gels, approximately 70% of the total protein was estimated to be recombinant plasminogen (FIG. 4, Lane 2). Thus, deposit of expressed recombinant plasminogen in inclusion bodies provided relatively pure target protein at the beginning of this process.

The refolding procedure was carried out at protein concentration of about 0.5 g/L. Solubilized/reduced recombinant plasminogen from inclusion bodies was oxidatively refolded, by dilution refolding, to catalytically-active protein (determined in the presence of stoichiometric SK) having a specific activity of 0.34; this corresponds to an estimated yield of 34% for the refolding step (relative to total protein). If the refolding yield is normalized based only upon the content of recombinant plasminogen protein present in inclusion bodies, it increases to approximately 48%.

Example 3

Filtration/Diafiltration

The refolding mixture in example 2 was clarified by passing through a 0.054 $m^2$ Millipore Millistak Pod+A1HC depth filter. This filtrate was further filtered through a 0.01 $m^2$ Millipore Express SHC Opticap XL 150 filter (0.5/0.2 µm). Diafiltration of this latter filtrate was performed with two 0.11 $m^2$ 30 kDa GE Healthcare Kvick cassettes. The diafiltration buffer was 10 mM Tris, 1.0 mM EDTA, 5.0 mM ε-ACA, 50 mM urea, pH 9.0. Between 37 and 40 L of buffer exchange was required to reach the target conductivity of 1-2 mS/cm.

Refolding mixtures were first passed through a depth filter, to remove particulate aggregates of protein, and were then diafiltered. A subsequent filtration prior to chromatography was done to safeguard against fouling of the down-stream cation-exchange chromatography. Recovery of recombinant plasminogen activity through these three sequential filtration/diafiltration/filtration steps was approximately 81%.

Example 4

Polyethylene (PEG) Precipitation

Solid polyethylene glycol (PEG) was added to a refolding composition (an undialyzed refolding composition comprising 0.5 M arginine and 0.85 M urea) of recombinant plasminogen to precipitate aggregated protein that may be present following oxidative refolding.

Figure 6:
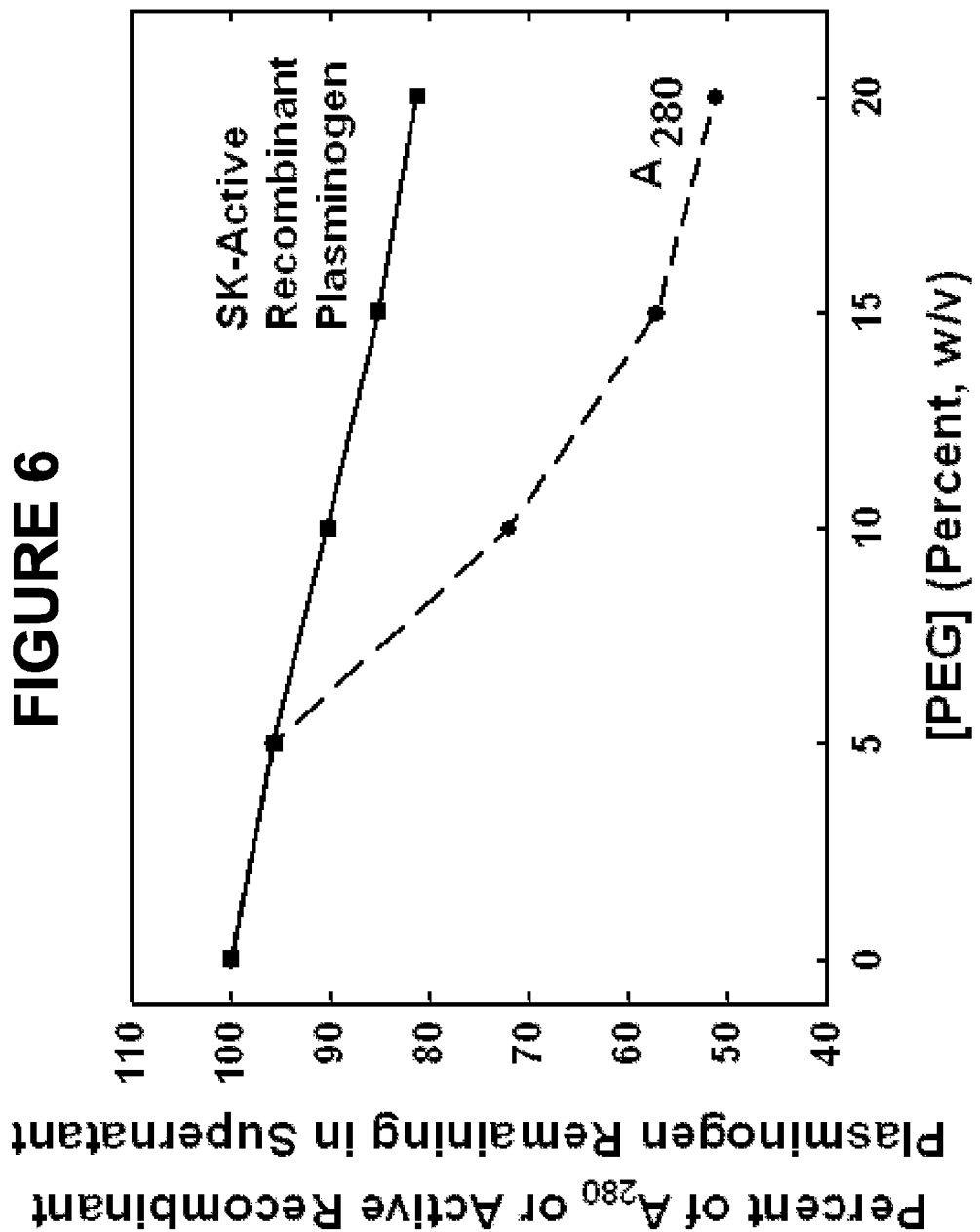
FIG. 6 is a graph showing the percentage of initial soluble total protein ($A_{280}$) and recombinant plasminogen activity remaining in solution after addition of solid polyethylene glycol (PEG) to the indicated concentrations and removal of formed precipitate by centrifugation.

Amounts of solid PEG were added to cold (5° C.) 50-ml portions of refolding mixture, with vigorous stirring, to achieve final concentrations of PEG of 5, 10, 15 or 20% (w/v). Stirring was continued for 60 minutes to ensure complete solubilization of the PEG. These samples, as well as a sample of the original refolding mixture to which no PEG had been added, were centrifuged at 16,000 rpm for 30 minutes to pellet any precipitate that had formed. The clear supernatants were collected and assessed for total protein content (by measurement of $A_{280}$) and for content of active recombinant plasminogen (by SK-activation assay, DiaPharma, West Chester, Ohio) and were analyzed by size-exclusion high-performance liquid chromatography (SEC-HPLC). The results are summarized in Table 1 and FIG. 6 and show that addition of PEG resulted in: (i.) relatively selective precipitation of protein that was not active recombinant plasminogen; (ii.) a resultant increase in the specific activity of the recombinant plasminogen that remained soluble; and (iii.) elimination of aggregated protein. These results demonstrate that addition of PEG to undialyzed refolding mixture caused precipitation of some protein (that was not active recombinant plasminogen) and preserved most of the active-SK-active recombinant plasminogen in solution. Moreover, SEC-HPLC demonstrated that addition of PEG to the undialyzed refolding mixture resulted in a progressive reduction in aggregated protein and in a corresponding increase in monomeric recombinant plasminogen in the PEG supernatants. The results indicate that PEG somewhat selectively precipitated incorrectly refolded or aggregated recombinant plasminogen and, thereby, enriched correctly refolded recombinant plasminogen in the PEG supernatant. The specific activity of SK-active recombinant plasminogen in this undialyzed refolding mixture increased from 0.33 to 0.53 in the 20% PEG supernatant. The results indicated that PEG precipitation is a viable method for selectively eliminating at least a portion of the SK-inactive recombinant plasminogen present in refolding mixtures prior to a chromatography or an SK-activation step.

TABLE 1

PEG Precipitation Analysis

| Sample | Col. 1 | Col. 2 | Col. 3 | Col. 4 | Col. 5 | Col. 6 | Col. 7 | Col. 8 |
|---|---|---|---|---|---|---|---|---|
| 0% PEG Supernatant | 1.349 | 0.812 | 0.266, 0.259 | 0.328, 0.319 | '100' | '100' | 41.5 | 52.5 |
| 5% PEG Supernatant | 1.305 | 0.786 | 0.255, 0.257 | 0.324, 0.327 | 96.7 | 97.5 | 60.6 | 39.5 |
| 10% PEG Supernatant | 0.987 | 0.595 | 0.241, 0.242 | 0.405, 0.407 | 73.2 | 92.0 | 86.9 | 13.1 |
| 15% PEG Supernatant | 0.789 | 0.475 | 0.227, 0.229 | 0.478, 0.482 | 58.5 | 86.9 | 98.6 | 1.4 |
| 20% PEG Supernatant | 0.691 | 0.416 | 0.219, 0.216 | 0.526, 0.519 | 51.2 | 82.9 | 99.8 | 0.2 |

In Table 1:
Column 1, $A_{280}$ of PEG supernatant;
Column 2, concentration of total recombinant plasminogen present in PEG supernatant, calculated by dividing the $A_{280}$ value by the extinction coefficient of 1.66 for a 1.0-mg/ml solution of recombinant plasminogen;
Column 3, concentration of SK-active recombinant plasminogen present in PEG supernatant (duplicate assay values);
Column 4, specific activity of SK-active recombinant plasminogen, calculated by dividing values in Column 3 by corresponding values in Column 2 (duplicate values based upon duplicate assays);
Column 5, percent of original $A_{280}$ value remaining in PEG supernatant;
Column 6, percent of original SK-active plasminogen remaining in PEG supernatant;
Column 7, percentage of total recombinant plasminogen present in the PEG supernatant as monomeric recombinant plasminogen (based upon SEC-HPLC);
Column 8, percentage of total recombinant plasminogen present in PEG supernatant as aggregated protein (based upon SEC-HPLC).

Example 5

Ammonium Sulfate Precipitation

Solid ammonium sulfate was added to a refolding composition (an undialyzed refolding composition comprising 0.5 M arginine and 0.85 M urea) of recombinant plasminogen to precipitate aggregated protein that may be present following oxidative refolding.

Figure 7:
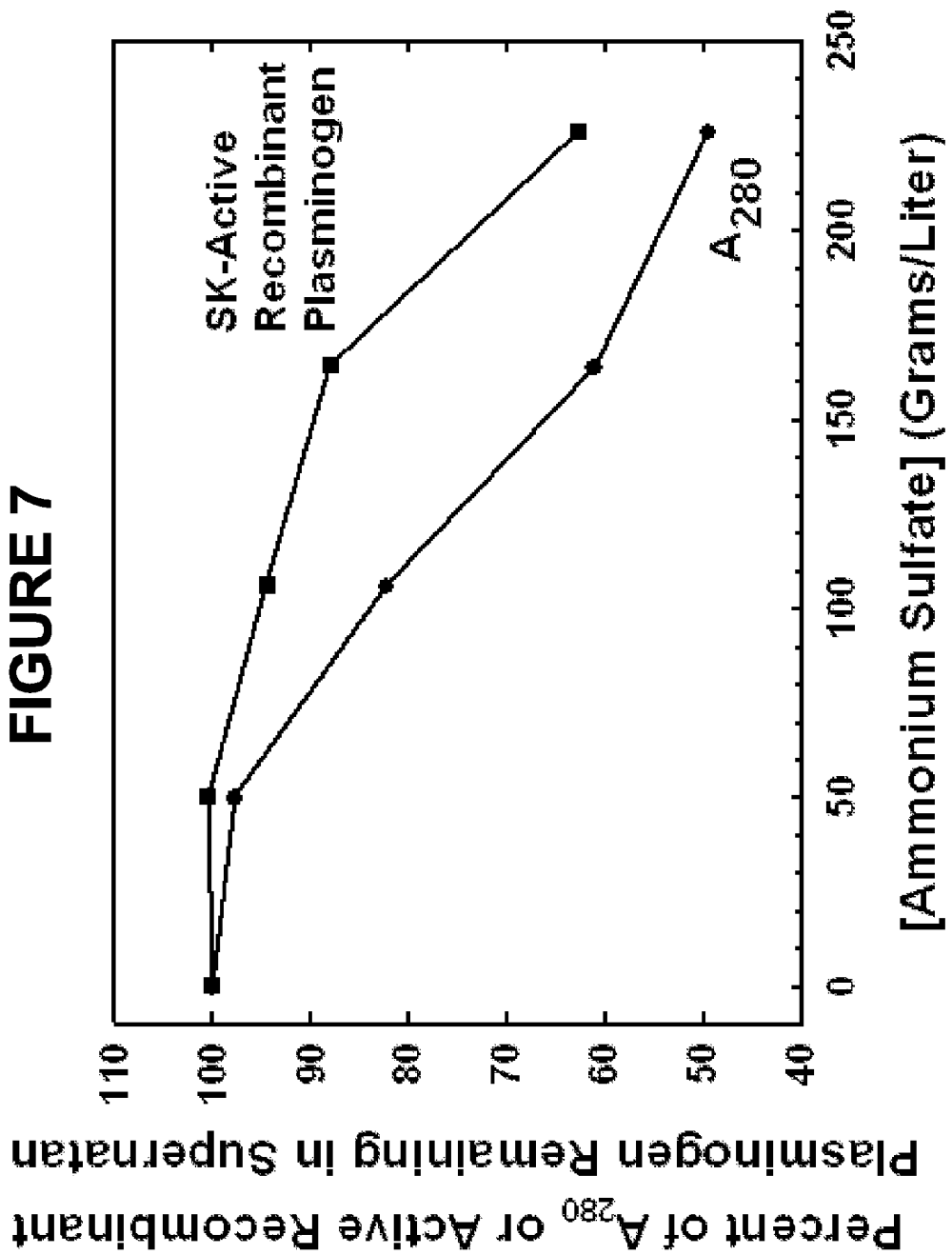
FIG. 7 is a graph showing the percentage of initial soluble total protein ($A_{280}$) and recombinant plasminogen activity remaining in solution after addition of solid ammonium sulfate to the indicated concentrations and removal of formed precipitate by centrifugation.

Solid ammonium sulfate was added to cold (5° C.) 50-ml portions of refolding mixture, with vigorous stirring, to achieve final concentrations of ammonium sulfate corresponding to 10, 20, 30 or 40% saturation, respectively. Stirring was continued for 60 minutes to ensure complete solubilization of the ammonium sulfate. These samples, as well as a sample of the original refolding mixture to which no ammonium sulfate had been added, were centrifuged at 16,000 rpm for 30 minutes to pellet any precipitate that had formed. The clear supernatants were collected and assessed for total protein content (by measurement of $A_{280}$) and for content of active recombinant plasminogen (by SK-activation assay, DiaPharma, West Chester, Ohio), and were analyzed by size-exclusion high-performance liquid chromatography (SEC-HPLC). The results are summarized in Table 2 and FIG. 7 and show that addition of ammonium sulfate resulted in: (i.) relatively selective precipitation of protein that was not active recombinant plasminogen; (ii.) a resultant increase in the specific activity of the recombinant plasminogen that remained soluble; and (iii.) elimination of aggregated protein. These results demonstrate that addition of ammonium to undialyzed refolding mixture caused precipitation of some protein (that was not active recombinant plasminogen) and preserved most of the active-SK-active recombinant plasminogen in solution. Moreover, size-exclusion high-performance liquid chromatography (SEC-HPLC) demonstrated that addition of ammonium to the undialyzed refolding mixture resulted in a progressive reduction in aggregated protein and in a corresponding increase in monomeric recombinant plasminogen in the ammonium sulfate supernatants. The results indicate that ammonium sulfate somewhat selectively precipitated incorrectly refolded or aggregated recombinant plasminogen and, thereby, enriched correctly refolded recombinant plasminogen in the ammonium sulfate supernatant. The specific activity of SK-active recombinant plasminogen in this undialyzed refolding mixture increased from 0.33 to 0.48 in the 30% saturated ammonium sulfate supernatant; addition of a higher amount of ammonium sulfate had the apparent effect of causing significant precipitation of SK-active recombinant plasminogen. The results indicated that ammonium sulfate precipitation is a viable method for selectively eliminating at least a portion of the SK-inactive recombinant plasminogen present in refolding mixtures prior to a chromatography or an SK-activation step.

TABLE 2

Ammonium Sulfate ($AmSO_4$) Precipitation Analysis

| Sample | Col. 1 | Col. 2 | Col. 3 | Col. 4 | Col. 5 | Col. 6 | Col. 7 | Col. 8 |
|---|---|---|---|---|---|---|---|---|
| 0% $AmSO_4$ Supernatant | 1.349 | 0.812 | 0.270, 0.272 | 0.333, 0.335 | '100' | '100' | 46.1 | 44.5 |
| 10% $AmSO_4$ Supernatant | 1.316 | 0.793 | 0.274, 0.270 | 0.346, 0.340 | 97.6 | 100.4 | 49.1 | 48.2 |
| 20% $AmSO_4$ Supernatant | 1.109 | 0.668 | 0.256, 0.256 | 0.383, 0.383 | 82.2 | 94.5 | 94.6 | 5.4 |
| 30% $AmSO_4$ Supernatant | 0.824 | 0.496 | 0.236, 0.241 | 0.476, 0.486 | 61.1 | 88 | 99.1 | 0.9 |

TABLE 2-continued

Ammonium Sulfate (AmSO$_4$) Precipitation Analysis

| Sample | Col. 1 | Col. 2 | Col. 3 | Col. 4 | Col. 5 | Col. 6 | Col. 7 | Col. 8 |
|---|---|---|---|---|---|---|---|---|
| 40% AmSO$_4$ Supernatant | 0.669 | 0.403 | 0.170, 0.170 | 0.422, 0.422 | 49.6 | 62.7 | 100 | 0 |

In Table 2:
Column 1, A$_{280}$ of ammonium sulfate supernatant;
Column 2, concentration of total recombinant plasminogen present in ammonium sulfate supernatant, calculated by dividing the A$_{280}$ value by the extinction coefficient of 1.66 for a 1.0-mg/ml solution of recombinant plasminogen;
Column 3, concentration of SK-active recombinant plasminogen present in ammonium sulfate supernatant (duplicate assay values);
Column 4, specific activity of SK-active recombinant plasminogen, calculated by dividing values in Column 3 by corresponding values in Column 2 (duplicate values based upon duplicate assays);
Column 5, percent of original A$_{280}$ value remaining in ammonium sulfate supernatant;
Column 6, percent of original SK-active plasminogen remaining in ammonium sulfate supernantant;
Column 7, percentage of total recombinant plasminogen present in the ammonium sulfate supernatant as monomeric recombinant plasminogen (based upon SEC-HPLC);
Column 8, percentage of total recombinant plasminogen present in ammonium sulfate supernatant as aggregated protein (based upon SEC-HPLC).

Example 6

Hydrophobic Interaction Chromatography Following Ammonium Sulfate Precipitation

Solid (NH$_4$)$_2$SO$_4$ was added to a recombinant plasminogen-containing refolding composition (pH 8.0) to 1M. The precipitate formed was removed by filtration (0.45 μm) and the post-filtration solution was contacted with the following hydrophobic interaction chromatography media:

Run 1. HiTrap™ Phenyl Sepharose FF: Load: 25 ml (A280: 0.839); Flow-through (FT)/Wash: 49.4 g (A$_{280}$: 0.266); Eluate: 96 well plate with fractions.

Run 2. HiTrap™ Octyl Sepharose FF: Load: 25 ml (A280: 0.839); Flow-through (FT)/Wash: 49.6 g (A$_{280}$: 0.407); Eluate: 96 well plate with fractions. This run did not show any real eluate peak.

Run 3. HiTrap™ Butyl Sepharose FF: Load: 25 ml (A280: 0.839); Flow-through (FT)/Wash: 49.05 g (A$_{280}$: 0.215); Eluate: 96 well plate with fractions.

Run 4. HiTrap™ Phenyl Sepharose HP: Load: 25 ml (A280: 0.839); Flow-through (FT)/Wash: 49.01 g (A$_{280}$: 0.183); Eluate: 96 well plate with fractions.

Chromatography: Buffer A: 25 mM Tris-HCl, pH 8.0, 1 mM EDTA, and 1 M (NH$_4$)$_2$SO$_4$; and Buffer B: 25 mM Tris-HCl, pH 8.0, and 1 mM EDTA (100-0% reverse gradient in 40 CV at 1 ml/min). Fractions were collected at the 1 ml scale.

The following fractions from the runs were subjected to dialysis for at least two days against 10 mM Tris-HCl, pH 9.0, and 1 mM EDTA at 4° C.: Fraction #1—Phenyl Sepharose FF (B1-B11); Fraction #2—Phenyl Sepharose FF (B12-D5); Fraction #3—Phenyl Sepharose FF (D6-D11); Fraction #4—Phenyl Sepharose FF flow-through; Fraction #5—Octyl Sepharose flow-through; Fraction #6—Column load; Fraction #7—Butyl Sepharose (A6-B12); Fraction #8—Butyl Sepharose (C1-C7); Fraction #9—Butyl Sepharose (C8-D12); Fraction #10—Butyl Sepharose flow-through; Fraction #11—Phenyl Sepharose HP (A12-B12); Fraction #12—Phenyl Sepharose HP(C1-D1); Fraction #13—Phenyl Sepharose HP flow-through; and Fraction #14—Column load.

Figure 8:
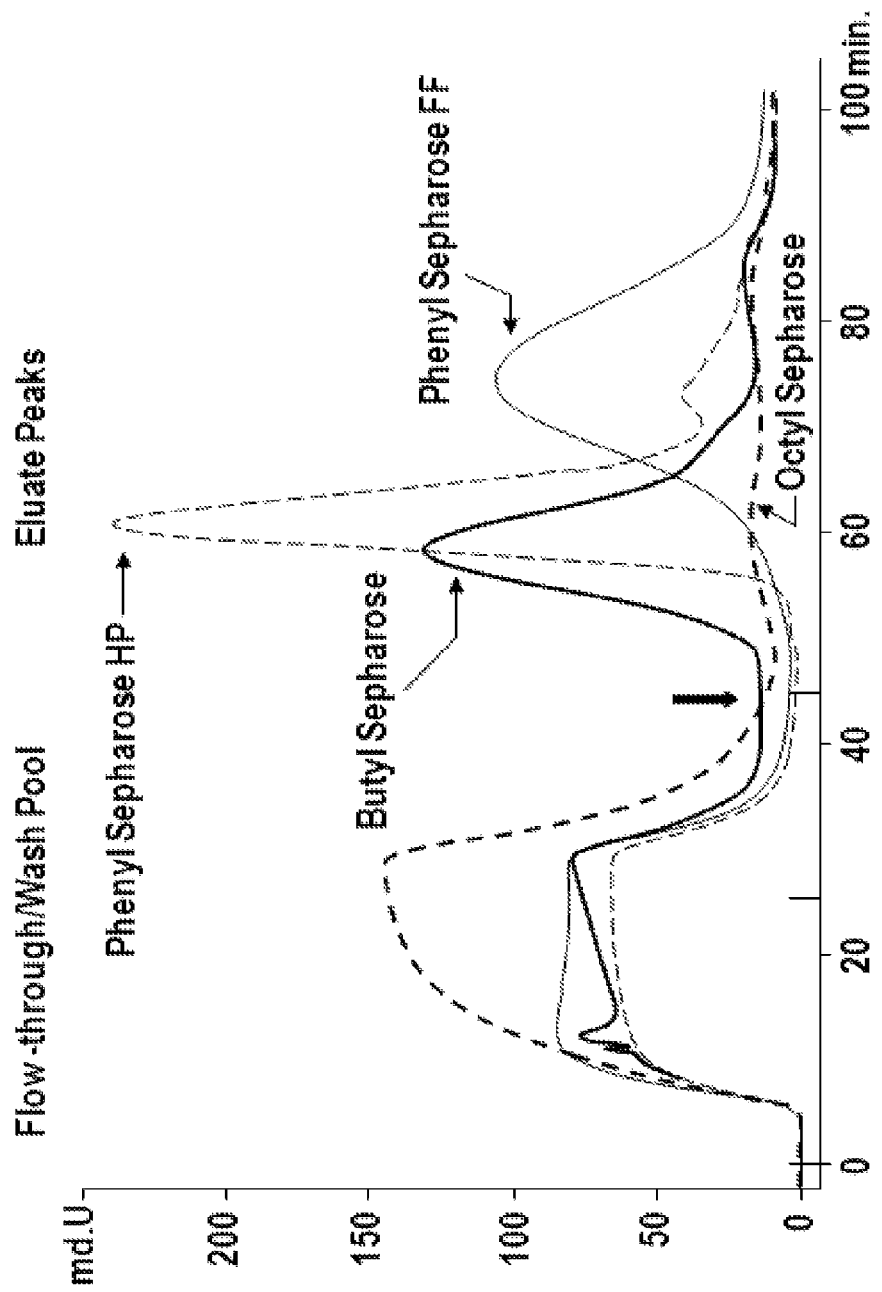
FIG. 8 is an overlay of chromatograms ($A_{280}$ absorbance traces) of hydrophobic interaction chromatography (HIC) resin screening experiments demonstrating the direct capture of recombinant plasminogen (TAL6003Z) from ammonium sulfate precipitated refolds. The start of the elution phase of each run is denoted by the black arrow and coincides with the onset of fraction collection.

The A$_{280}$ absorbance traces of the four hydrophobic interaction chromatography runs are shown in FIG. 8. Potency analysis of selected fractions showed that the Phenyl Sepharose FF (B12-D5) pooled Fraction #2 had a specific activity of 0.91, while the flow-through pool Fraction #4 had a specific of 0.003. Similarly, the specific activity of the Phenyl Sepharose HP (A12-B12) pooled Fraction #11 was 1.01, while the specific activity of the flow-through Fraction #13 for this run was negligible. Fraction #7, Butyl Sepharose (A6-B12), had a specific activity of 0.61, Fraction #8, Butyl Sepharose (C1 -C7) a specific activity of 0.21, and Fraction #10, Butyl Sepharose flow-through a specific activity of 0.05. No capture peak was achieved with the Octyl Sepharose resin, and the flow-through Fraction #5 from this run had a specific activity of 0.42.

The result show that the supernatant/filtrate from the ammonium sulfate precipitation step is amenable to direct application to hydrophobic interaction chromatography. Phenyl Sepharose FF, Phenyl Sepharose HP, and Butyl Sepharose FF are able to selectively capture most of the active recPlasminogen protein from the refold mixture, evident by a high specific activity in the eluate fractions and a low specific activity in the flow-through pools. Thus, for example, following ammonium sulfate precipitation, the precipitate can be clarified by one or more methods (e.g., depth filtration, centrifugation, microfiltration, etc., and/or combinations thereof) that remove all or a substantial amount of any precipitate, and the clarified filtrate comprising plasminogen can be subjected to hydrophobic interaction chromatography to capture the recombinant plasminogen contained therein.

Example 7

Cation-Exchange Chromatography

Refolded, diafiltered recombinant plasminogen was captured on a 206-ml column of SP Sepharose FF (GE Healthcare, Pittsburgh, Pa.) at room temperature. The column equilibration buffer was 25 mM Tris, 1.0 mM EDTA, pH 8.0. After the column was washed with 10 column volumes of equilibration buffer, the recombinant plasminogen was eluted with 25 mM Tris, 200 mM NaCl, 1.0 mM EDTA, pH 8.0.

The SP Sepharose column eluate provided nearly homogeneous recombinant plasminogen, having a specific activity of 0.98, with a recovery of approximately 89% of the recombinant plasminogen activity. This chromatography step was highly effective in reducing contamination of the recombinant plasminogen by host-cell protein as shown in Table 3.

TABLE 3

Purification of recombinant plasminogen from *E. coli* inclusion bodies

| Purification Step | Protein Concentration (mg/ml)[a] | Total Protein (mg)[a,b] | Total Activity (mg)[a,b] | Activity Recovered (%)[a,b] | Specific activity[c] | Host Cell Protein (ng/mg Protein) |
|---|---|---|---|---|---|---|
| Solubilized inclusion bodies | 8.88 ± 0.72 | 4,424 ± 356 | DND[d] | — | — | DND |
| Refolded plasminogen | 0.51 ± 0.05 | 5,133 ± 454 | 1,720 ± 46 | 33.6 ± 2.2 | 0.34 ± 0.02 | DND |
| (Post-refold filtrate plasminogen) | 0.38 ± 0.02 | 4,039 ± 274 | 1,604 ± 185 | 93.2 ± 9.9 | 0.40 ± 0.02 | DND |
| (Diafiltration retentate plasminogen) | 0.34 ± 0.03 | 3,386 ± 282 | 1,604 ± 252 | 99.8 ± 9.2 | 0.47 ± 0.04 | DND |
| (Pre-SP Sepharose filtrate plasminogen) | 0.32 ± 0.02 | 3,313 ± 132 | 1,379 ± 5 | 87.6 ± 15.0 | 0.42 ± 0.02 | 2,464 ± 897 |
| SP Sepharose eluate plasminogen | 2.29 ± 0.13 | 1,255 ± 25 | 1,225 ± 26 | 88.8 ± 1.9 | 0.98 ± 0.02 | 31.9 ± 20.5 |
| ECH Lysine eluate plasminogen | 5.96 ± 0.56 | 1,137 ± 104 | 1,194 ± 34 | 97.4 ± 0.7 | 1.05 ± 0.08 | 1.60 ± 1.4 |

[a]Values represent the mean ± the standard deviation from the mean for three different purification runs, each starting with a different batch of inclusion bodies.
[b]Values not corrected for volume of sample withdrawn for bioanalytical assays.
[c]Specific activity, mg of active recombinant plasminogen per mg of total protein.
[d]Analysis was not conducted on these samples.

Example 8

Affinity Chromatography

Recombinant plasminogen eluted from the SP Sepharose column was subsequently bound to, and eluted from, an ECH-Lysine Sepharose column. This latter affinity chromatography step also served to confirm that all or substantially all of the protein processed further downstream contains a correctly refolded lysine-binding site on the kringle domain.

The eluate from the SP Sepharose column was loaded on to a 295-ml column of ECH-Lysine Sepharose 4 FF (GE Healthcare, Pittsburgh, Pa.) at room temperature equilibrated with 50 mM Tris, 200 mM NaCl, 1.0 mM EDTA, pH 8.0. After the column was washed with 4 column volumes of equilibration buffer and then with 3 column volumes of wash 2 buffer (50 mM Tris, pH 8.0, and 1 mM EDTA), plasminogen was eluted with 50 mM Tris, 20 mM ε-ACA, 1.0 mM EDTA, pH 8.0. This column eluate was stored frozen at −80° C. until the next step of the purification process was initiated.

Almost quantitative recovery of the recombinant plasminogen was achieved from the ECH-Lysine Sepharose chromatography step, with a specific activity of unity. This affinity column was also effective in further reducing the content of host-cell protein.

Example 9

Activation of Plasminogen to Plasmin Using Soluble Streptokinase

Thawed recombinant plasminogen was activated with streptokinase (SK) for 4 hr at room temperature under the following solution conditions: 2.5 mg of plasminogen/ml; 12.5% (v/v) 1,2-propanediol; 200 mM ε-ACA; 87.5% (v/v) ECH-Lysine Sepharose elution buffer; 25 µg of SK/ml; pH 7.0.

SK was used to activate the recombinant plasminogen to plasmin in free solution. The conditions for activation were selected carefully to maximize activation of the recombinant plasminogen and to minimize autolysis. The specific activity of plasmin at the end of the 4-hr activation period was 0.77, indicating an approximately 80% yield at this step.

Example 10

Activation of Plasminogen to Plasmin Using Immobilized Recombinant Polyhistidine-Tagged Streptokinase Recombinant polyhistidine-tagged streptokinase (100 µg) in 10 mM Tris-HCl (pH 8.0) and 100 mM NaCl is added to 100 µl of immobilized metal ion affinity chromatography (IMAC) matrix. After incubation at 22° C. for 5 min, the slurry is applied to a Spin-X microcentrifuge spin column (Costar, Cambridge, Mass.) fitted with a 0.45-µm cellulose acetate filter. The matrix is pelleted by centrifugation at 2,000×g for 3 min and is subsequently washed several times with 20 mM Tris-HCl, pH 7.4. The matrix is removed from the Spin-X unit, placed in a microcentrifuge tube, and resuspended in 200 ml of 50 mM Tris-HCl buffer, pH 7.4.

An equimolar amount of the recombinant plasminogen is added to the immobilized streptokinase in an activating solution: 50 mM Tris-HCl buffer, pH 7.4. Samples are incubated at 22° C. and placed on a rotating platform to keep the matrix in suspension. Upon completion of activation, the activation solution is filtered from streptokinase-SEPHAROSE™ on a glass filter and immediately applied on Q-membrane or benzamidine-SEPHAROSE™ column. To monitor the progress of plasminogen activation, at different intervals a sample is selected and the reaction is terminated by the addition of 0.1 volumes of 10× stop buffer (1.0 M NaHCO$_3$, 1.0 M ε-aminocaproic acid [pH 9.4]). The sample is transferred to a Spin-X microcentrifuge tube and pelleted by centrifugation at 2,000×g for 3 mM Immobilized reactants are eluted by addition of 25 ul of 100 mM EDTA, followed by centrifugation at 5,000×g for 10 min. Reduced SDS-PAGE was carried out by conventional methodology.

Example 11

Anion Exchange Chromatography

The SK-activation mixture of Example 9 was diluted 1:1 with 200 mM ε-ACA/12.5% 1,2-propanediol and pH-adjusted to 9.0. This solution was passed through a Sartobind SingleSep Q Nano 1-ml membrane (Sartorius) at room temperature.

The activation solution was passed through a Q membrane to remove SK, with 91% recovery of plasmin; this separation is made possible by the disparate pI values for the recombinant plasmin (9.3 and 9.5) and SK (5.2). Based upon Western blot analysis of the load material and flow-through from this Q membrane, SK was reduced to below the level of quantification by this step.

Example 12

Affinity Chromatography

The Q membrane flow-through of Example 11 was supplemented with NaCl (to 0.5 M) and pH-adjusted to 7.0 prior to being loaded on to a 200-ml column of Benzamidine Sepharose 4 FF (high sub) (GE Healthcare, Pittsburgh, Pa.) equilibrated with 25 mM Tris, 500 mM NaCl, 250 mM ε-ACA, pH 7.0 at room temperature. After the column was washed with 5 column volumes of equilibration buffer, the plasmin was eluted with 200 mM sodium citrate, 200 mM ε-ACA, 300 mM NaCl, pH 3.0. This column eluate was collected in a vessel containing one column volume of elution buffer, for the purpose of rapidly lowering the pH (to 3.0) of plasmin present in the peak front.

The Q membrane flow-through was loaded on to a Benzamidine Sepharose column to bind active plasmin and to eliminate unreacted recombinant plasminogen and autolyzed plasmin. Plasmin activity was recovered with a yield of approximately 95% during this step.

Example 13

Ultrafiltration/Diafiltration

Plasmin present in the eluate from the Benzamidine Sepharose column was concentrated approximately 5-fold (to 5 mg/ml) and diafiltered against 5.0 mM sodium citrate (pH 3.3), using a 5 kDa Millipore Pellicon XL (0.005 m$^2$) membrane. Following diafiltration, this acidic plasmin solution was stored at −80° C.

Example 14

Plasmin Concentration, Activity and Purity

Total protein was quantified in upstream purification intermediates by the pyrogallol red method using a plasminogen standard that had been calibrated based upon its absorbance at 280 nm. The extinction coefficient for pure recombinant plasmin was calculated to be 1.66 mg$^{-1}$/ml based upon amino acid composition; absorbance at 280 nm was used to quantify plasmin protein in downstream purification intermediates. Plasminogen activity was assayed using the COAMATIC® Plasminogen kit (DiaPharma Group, Inc.). The latter kit was also used to assay plasmin activity but without addition of SK to the assay mixtures; these assays were calibrated and validated to measure the concentration of catalytically-active zymogen. Conventional SDS-PAGE was performed under reducing conditions. Size-exclusion HPLC was performed with a 7.8 mm×30 cm TSK-GEL G2000SW$_{XL}$, column (Tosoh BioScience) with 10 mM acetic acid, 100 mM NaCl, pH 3.4, as mobile phase. E. coli BL21 host-cell proteins were assayed with an ELISA kit from Cygnus Technologies. SK was estimated with a semi-quantitative Western blot using custom-prepared, affinity-purified rabbit anti-SK sera.

The primary criterion for purity of plasminogen and plasmin is the specific activity of the preparations, with a specific activity of 1.0 representing 100% pure protein. As shown in Tables 3 and 4, the specific activities of the plasminogen intermediate and the plasmin final product were both close to 1.0.

TABLE 4

| | Purification of plasmin from purified plasminogen | | | | | | |
|---|---|---|---|---|---|---|---|
| Purification step | Col. 1 (mg/ml) | Col. 2 (mg)$^{a,b}$ | Col. 3 (mg)$^{a,b}$ | Col. 4 (%)$^{a,b}$ | Col. 5 Specific activity$^c$ | Col. 6 (ng/mg Protein) | Col. 7 (μg/mg Protein) |
| Streptokinase-activated plasmin | 2.47 ± 0.01 | 636 ± 49 | 489 ± 47 | 82.9 ± 3.6 | 0.77 ± 0.03 | DND$^d$ | 4.2 ± 1.5 |
| Q membrane flow-through | 1.00 ± 0.01 | 574 ± 46 | 425 ± 30 | 91.1 ± 0.3 | 0.74 ± 0.01 | DND | <QL$^e$ |
| Benzamidine Sepharose eluate plasmin | 1.09 ± 0.08 | 472 ± 43 | 409 ± 37 | 96.1 ± 4.1 | 0.87 ± 0.03 | <12 | <QL |
| Ultrafiltered/diafiltered plasmin | 6.19 ± 0.28 | 459 ± 29 | 414 ± 11 | 101.7 ± 6.5 | 0.90 ± 0.05 | <0.9 | <QL |

In Table 4:
Column 1: Protein Concentration;
Column 2: Total Protein;
Column 3: Total Activity;
Column 4: Activity recovered in process step;
Column 5: Specific activity;
Column 6: Host cell protein;
Column 7: SK Concentration.
$^a$Values not corrected for volume of sample withdrawn for bioanalytical assays.

TABLE 4-continued

Purification of plasmin from purified plasminogen

| Purification step | Col. 1 (mg/ml) | Col. 2 (mg)[a,b] | Col. 3 (mg)[a,b] | Col. 4 (%)[a,b] | Col. 5 Specific activity[c] | Col. 6 (ng/mg Protein) | Col. 7 (µg/mg Protein) |
|---|---|---|---|---|---|---|---|

[b]Values represent the mean ± the standard deviation from the mean for three different purification runs.
[c]Specific activity, mg of active recombinant plasmin per mg of total protein.
[d]Analysis was not conducted on these samples.
[e]Below the level of quantification (0.15 µg/ml).

Figure 5:
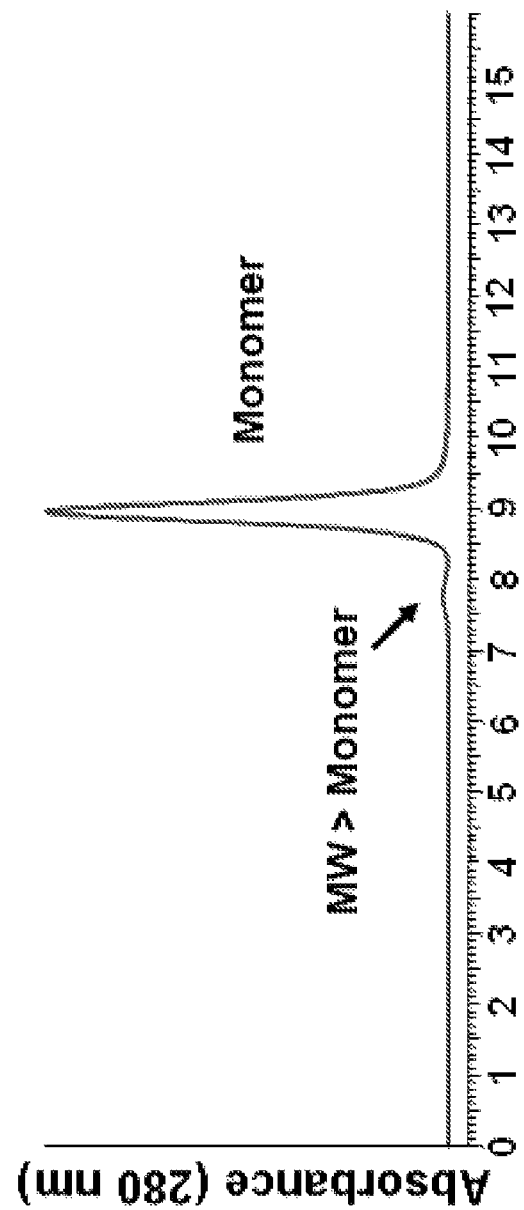
FIG. 5 shows a size-exclusion analysis of purified recombinant plasmin. Elution profiles ($A_{280}$) for the three preparations of purified recombinant plasmin are overlaid in the figure. Monomeric plasmin constituted 98.3±0.1% of the absorbance eluted from the column during each run. The remainder (1.7±0.1%) of the eluted absorbance was eluted before the main peak.

Corroborating these estimations of purity are the SDS-PAGE results presented in FIG. 4, which illustrate the progressive purification of plasminogen, conversion of single-chain plasminogen into two-chain plasmin by SK, and purification of plasmin. A small percentage of autolysis products was observed in the ultrafiltered/diafiltered plasmin at the end of the purification process (FIG. 4, lane 9). Size-exclusion HPLC analyses of the three samples of final product are overlaid in FIG. 5; this analysis demonstrated that 98% of the protein was eluted in the peak corresponding to monomeric plasmin. Host-cell protein was reduced to <0.8 ng/mg of purified plasmin. SK was reduced to below the level of quantification (<0.02 µg/mg of plasmin).

Recombinant plasminogen protein present in solubilized inclusion bodies was refolded into active protein with a yield of approximately 48%. The overall recovery of activity after ECH-Lysine Sepharose chromatography, based upon active, refolded zymogen, was 70%. The yield of plasmin activity, based upon starting zymogen activity, was 65%. Thus, the calculated overall yield of plasmin, based upon active, refolded zymogen, was 46% for the three purification runs presented in Tables 3 and 4.

Example 15

Anion Exchange Chromatography of Plasmin Prepared from Recombinant Plasminogen

A Q membrane chromatography was implemented immediately after activation of recombinant plasminogen to plasmin using SK. The SK activation mixture was pH-adjusted from about 7 to about 8, loaded onto the Q membrane equilibrated in pH 8 Tris buffer, and the flow-through containing plasmin was collected. Bench scale studies were performed and membrane loading conditions conducive to SK binding and plasmin recovery were identified. Samples from bench scale experiments were assayed for SK content and the sample purity was confirmed.

Example 16

Anion Exchange Chromatography of Plasmin Prepared from Plasma-Derived Plasminogen Blood-derived plasminogens and/or plasmins prepared therefrom, are disclosed by, e.g., U.S. Pat. Nos. 6,355,243, 6,964,764, 6,969,515, and 7,544,500; U.S. Patent Publication Nos. 2002/0192794 and 2003/0012778; and Deutsch et al., Science, 170:1095-6 (1970), each of which is herein incorporated by reference in its entirety. Accordingly, plasminogen is prepared from blood (e.g., plasma, serum) in order to provide a composition comprising the plasmin.

For example, plasminogen is prepared from Cohn Fraction II+III paste by affinity chromatography on Lys-SEPHAROSE as described by Deutsch et al. supra. For example, 200 g of a Cohn Fraction II+III paste is resuspended in 2 liter of 0.15M sodium citrate buffer, pH 7.8. The suspension is incubated overnight at 37° C., centrifuged at 14,000 rpm, filtered through fiberglass and mixed with 500 ml of Lys-SEPHAROSE 4B (Pharmacia). Binding of plasminogen is performed at room temperature for 2 hours. The Lys-SEPHAROSE is then be transferred onto a 2-liter glass filter, and washed several times with 0.15M sodium citrate containing 0.3M NaCl until the absorbance at 280 nm drops below 0.05. Bound plasminogen is eluted with three 200-ml portions of 0.2M ε-aminocaproic acid. Eluted plasminogen is precipitated with 0.4 g solid ammonium sulfate/ml of plasminogen solution. The precipitate of crude (80-85% pure) plasminogen can be stored at 4° C.

The ammonium sulfate precipitate of crude plasminogen is centrifuged at 14,000 rpm and resuspended in a minimal volume using 40 mM Tris, containing 10 mM lysine, 80 mM NaCl at pH 9.0 to achieve a final protein concentration of 10-15 mg/ml. The plasminogen solution is dialyzed overnight against the same buffer to remove ammonium sulfate. The dialyzed plasminogen solution (10-20 ml) is diluted with an equal volume of 100% glycerol and combined with an appropriate amount of a plasminogen activator, preferably streptokinase. The use of 50% glycerol can reduce autodegradation of plasmin formed during activation by the activator.

The plasminogen activation by the activator (e.g., streptokinase) is at room temperature for about 2 hours to about 24 hours or more. SDS-PAGE is performed under reducing conditions to monitor the progress of plasminogen activation. Upon completion of the activation, the activation solution comprising plasmin is filtered with a glass filter, if desired, and applied to an affinity adsorbent such as benzamidine-SEPHAROSE. Since the plasmin is a serine protease with trypsin-like specificity, benzamidine-Sepharose is an affinity adsorbent that can allow capture of the active plasmin. For example, a solution in 50% glycerol is applied to the 50 ml benzamidine-Sepharose column equilibrated with 0.05M Tris, pH 8.0, containing 0.5M NaCl with a flow rate of 3 ml/min. The column is run at 3 ml/min at 3-7° C. The front portion of the non-bound peak contains high-molecular weight impurities. The rest of the non-bound peak is represented by residual non-activated plasminogen and by inactive autodegradation products of plasmin.

To protect plasmin from inactivation at neutral pH conditions, acidic elution conditions are selected. The plasmin bound to benzamidine-Sepharose is eluted with, e.g., 0.2M glycine buffer, pH 3.0 containing 0.5M NaCl.

An eluate collected from a benzamidine Sepharose column was adjusted to pH about 6.5 to 7.0 and diluted 4-fold with water for injection (WFI). A Q membrane (Sartorius Sartobind MA 5 Q membrane) was equilibrated with equilibration buffer (62.5 mM ECAC, 37.5 mM NaCl, pH 6.5 to 7.0) and the diluted benzamidine eluate was loaded onto the Q membrane. The flow-through and rinse were collected, and the pH was immediately adjusted to pH 3.4 with 1 N HCl. This pH-adjusted flow-through was subsequently concentrated and diafiltered by UF/DF.

SDS-PAGE analysis confirmed that very little (~10% or less) of plasmin was bound to the Q membrane with the remainder being captured in the flow-through and rinse fractions (FIG. 9). And, Western blot analysis confirmed that the SK fragments present in the Q load were not present in the flow-through and rinse, but were present in the strip fraction when the Q membrane was treated with 62.5 mM EACA, 500 mM NaCl, pH 6.5. The Western blot was analyzed densitometrically and the results are shown in Table 5.

TABLE 5

Densitometric analysis of Western Blot lanes.

| Lane | Sample ID (samples tested neat) | 15 kD Conc. µg/ml |
|---|---|---|
| 1 | 1.0 µg/ml 15 kD standard | 1.000 |
| 2 | 0.5 µg/ml 15 kD standard | 0.500 |
| 3 | 0.15 µg/ml 15 kD standard | 0.150 |
| 4 | PBC 050 221 Benzamidine Load | >1.0 |
| 5 | PBC 060 221 Benzamidine Flow-through | >1.0 |
| 6 | PBC 070 221 Benzamidine Eluate | <0.15 |
| 7 | AJC 007 Benzamidine Load | 0.25 |
| 8 | AJC 008 Q Membrane Load, pH 6.5 | <0.15 |
| 9 | AJC 009 Q Membrane Flow-through, pH 6.5 | <0.15 |
| 10 | AJC 010 Q Membrane Wash, pH 6.5 | <0.15 |
| 11 | AJC 011 Q membrane Eluate, pH 6.5 | 0.46 |

The invention claimed is:

1. A method for preparing a recombinant plasminogen having a single kringle domain, a peptide linker sequence, an activation site, and a serine protease domain, wherein said single kringle domain is at least 90% identical to kringle 1 or kringle 4 of SEQ ID NO: 2; said peptide linker sequence between said single kringle domain and said serine protease domain consists of residues 91-94 of SEQ ID NO: 1; and said method comprises: contacting a composition comprising said recombinant plasminogen with a cation-exchange medium under a cation-exchange condition that is sufficient for said cation-exchange medium to bind said recombinant plasminogen; wherein said cation-exchange medium comprises a sulfopropyl ligand coupled to an agarose support.

2. The method of claim 1 further comprising: eluting the recombinant plasminogen bound by the cation-exchange medium to obtain a cation-exchange medium eluate comprising the recombinant plasminogen.

3. The method of claim 2 further comprising: contacting the cation-exchange medium eluate with a first affinity medium under a first affinity condition that is sufficient for the affinity medium to bind the recombinant plasminogen.

4. The method of claim 3, wherein the first affinity medium comprises a ligand coupled to a support, wherein the ligand has affinity for the recombinant plasminogen.

5. The method of claim 4, wherein the ligand is lysine, wherein the support is an agarose.

6. The method of claim 1 further comprising: expressing the recombinant plasminogen using a recombinant expression system.

7. The method of claim 6, wherein the step of expressing comprises performing the expression system under an expression condition sufficient to produce a recombinant plasminogen inclusion body.

8. The method of claim 7 further comprising: contacting the recombinant plasminogen inclusion body with a solubilization buffer under a solubilization condition sufficient to obtain a solubilized recombinant plasminogen inclusion body.

9. The method of claim 8 further comprising: contacting the solubilized recombinant plasminogen inclusion body with a refolding solution under a refolding condition to obtain a composition comprising the recombinant plasminogen.

10. The method of claim 1 further comprising: adding a polyethylene glycol (PEG) or a salt to a refolding solution under a precipitation condition, wherein the refolding solution comprises the recombinant plasminogen and aggregated polypeptides, wherein the recombinant plasminogen is refolded recombinant plasminogen, wherein the precipitation condition is sufficient to precipitate all or a substantial portion of the aggregated proteins.

* * * * *

SEQUENCE LISTING

```
<160> NUMBER OF SEQ ID NOS: 7

<210> SEQ ID NO 1
<211> LENGTH: 344
<212> TYPE: PRT
<213> ORGANISM: Homo sapiens

<400> SEQUENCE: 1

Met Arg Asp Val Val Leu Phe Glu Lys Lys Val Tyr Leu Ser Glu Cys
1               5                   10                  15

Lys Thr Gly Asn Gly Lys Asn Tyr Arg Gly Thr Met Ser Lys Thr Lys
            20                  25                  30

Asn Gly Ile Thr Cys Gln Lys Trp Ser Ser Thr Ser Pro His Arg Pro
        35                  40                  45

Arg Phe Ser Pro Ala Thr His Pro Ser Glu Gly Leu Glu Glu Asn Tyr
    50                  55                  60

Cys Arg Asn Pro Asp Asn Asp Pro Gln Gly Pro Trp Cys Tyr Thr Thr
65                  70                  75                  80

Asp Pro Glu Lys Arg Tyr Asp Tyr Cys Asp Val Pro Gln Cys Ala Ala
                85                  90                  95

Pro Ser Phe Asp Cys Gly Lys Pro Gln Val Glu Pro Lys Lys Cys Pro
            100                 105                 110

Gly Arg Val Val Gly Gly Cys Val Ala His Pro His Ser Trp Pro Trp
        115                 120                 125

Gln Val Ser Leu Arg Thr Arg Phe Gly Met His Phe Cys Gly Gly Thr
    130                 135                 140

Leu Ile Ser Pro Glu Trp Val Leu Thr Ala Ala His Cys Leu Glu Lys
145                 150                 155                 160

Ser Pro Arg Pro Ser Ser Tyr Lys Val Ile Leu Gly Ala His Gln Glu
                165                 170                 175

Val Asn Leu Glu Pro His Val Gln Glu Ile Glu Val Ser Arg Leu Phe
            180                 185                 190

Leu Glu Pro Thr Arg Lys Asp Ile Ala Leu Leu Lys Leu Ser Ser Pro
        195                 200                 205

Ala Val Ile Thr Asp Lys Val Ile Pro Ala Cys Leu Pro Ser Pro Asn
    210                 215                 220

Tyr Val Val Ala Asp Arg Thr Glu Cys Phe Ile Thr Gly Trp Gly Glu
225                 230                 235                 240

Thr Gln Gly Thr Phe Gly Ala Gly Leu Leu Lys Glu Ala Gln Leu Pro
                245                 250                 255
```

```
Val Ile Glu Asn Lys Val Cys Asn Arg Tyr Glu Phe Leu Asn Gly Arg
                260                 265                 270

Val Gln Ser Thr Glu Leu Cys Ala Gly His Leu Ala Gly Gly Thr Asp
                275                 280                 285

Ser Cys Gln Gly Asp Ser Gly Gly Pro Leu Val Cys Phe Glu Lys Asp
        290                 295                 300

Lys Tyr Ile Leu Gln Gly Val Thr Ser Trp Gly Leu Gly Cys Ala Arg
305                 310                 315                 320

Pro Asn Lys Pro Gly Val Tyr Val Arg Val Ser Arg Phe Val Thr Trp
                    325                 330                 335

Ile Glu Gly Val Met Arg Asn Asn
                340

<210> SEQ ID NO 2
<211> LENGTH: 810
<212> TYPE: PRT
<213> ORGANISM: Homo sapiens

<400> SEQUENCE: 2

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
                20                  25                  30

Leu Phe Ser Val Thr Lys Lys Gln Leu Gly Ala Gly Ser Ile Glu Glu
            35                  40                  45

Cys Ala Ala Lys Cys Glu Glu Asp Glu Glu Phe Thr Cys Arg Ala Phe
        50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
                100                 105                 110

Gly Thr Met Ser Lys Thr Lys Asn Gly Ile Thr Cys Gln Lys Trp Ser
            115                 120                 125

Ser Thr Ser Pro His Arg Pro Arg Phe Ser Pro Ala Thr His Pro Ser
130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                    165                 170                 175

Asp Ile Leu Glu Cys Glu Glu Glu Cys Met His Cys Ser Gly Glu Asn
                180                 185                 190

Tyr Asp Gly Lys Ile Ser Lys Thr Met Ser Gly Leu Glu Cys Gln Ala
            195                 200                 205

Trp Asp Ser Gln Ser Pro His Ala His Gly Tyr Ile Pro Ser Lys Phe
210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                    245                 250                 255

Cys Asp Ile Pro Arg Cys Thr Thr Pro Pro Pro Ser Ser Gly Pro Thr
                260                 265                 270

Tyr Gln Cys Leu Lys Gly Thr Gly Glu Asn Tyr Arg Gly Asn Val Ala
            275                 280                 285
```

```
Val Thr Val Ser Gly His Thr Cys Gln His Trp Ser Ala Gln Thr Pro
    290                 295                 300
His Thr His Asn Arg Thr Pro Glu Asn Phe Pro Cys Lys Asn Leu Asp
305                 310                 315                 320
Glu Asn Tyr Cys Arg Asn Pro Asp Gly Lys Arg Ala Pro Trp Cys His
                325                 330                 335
Thr Thr Asn Ser Gln Val Arg Trp Glu Tyr Cys Lys Ile Pro Ser Cys
            340                 345                 350
Asp Ser Ser Pro Val Ser Thr Glu Gln Leu Ala Pro Thr Ala Pro Pro
        355                 360                 365
Glu Leu Thr Pro Val Val Gln Asp Cys Tyr His Gly Asp Gly Gln Ser
    370                 375                 380
Tyr Arg Gly Thr Ser Ser Thr Thr Thr Thr Gly Lys Lys Cys Gln Ser
385                 390                 395                 400
Trp Ser Ser Met Thr Pro His Arg His Gln Lys Thr Pro Glu Asn Tyr
                405                 410                 415
Pro Asn Ala Gly Leu Thr Met Asn Tyr Cys Arg Asn Pro Asp Ala Asp
            420                 425                 430
Lys Gly Pro Trp Cys Phe Thr Thr Asp Pro Ser Val Arg Trp Glu Tyr
        435                 440                 445
Cys Asn Leu Lys Lys Cys Ser Gly Thr Glu Ala Ser Val Val Ala Pro
    450                 455                 460
Pro Pro Val Val Leu Leu Pro Asp Val Glu Thr Pro Ser Glu Glu Asp
465                 470                 475                 480
Cys Met Phe Gly Asn Gly Lys Gly Tyr Arg Gly Lys Arg Ala Thr Thr
                485                 490                 495
Val Thr Gly Thr Pro Cys Gln Asp Trp Ala Ala Gln Glu Pro His Arg
            500                 505                 510
His Ser Ile Phe Thr Pro Glu Thr Asn Pro Arg Ala Gly Leu Glu Lys
        515                 520                 525
Asn Tyr Cys Arg Asn Pro Asp Gly Asp Val Gly Gly Pro Trp Cys Tyr
    530                 535                 540
Thr Thr Asn Pro Arg Lys Leu Tyr Asp Tyr Cys Asp Val Pro Gln Cys
545                 550                 555                 560
Ala Ala Pro Ser Phe Asp Cys Gly Lys Pro Gln Val Glu Pro Lys Lys
                565                 570                 575
Cys Pro Gly Arg Val Val Gly Gly Cys Val Ala His Pro His Ser Trp
            580                 585                 590
Pro Trp Gln Val Ser Leu Arg Thr Arg Phe Gly Met His Phe Cys Gly
        595                 600                 605
Gly Thr Leu Ile Ser Pro Glu Trp Val Leu Thr Ala Ala His Cys Leu
    610                 615                 620
Glu Lys Ser Pro Arg Pro Ser Ser Tyr Lys Val Ile Leu Gly Ala His
625                 630                 635                 640
Gln Glu Val Asn Leu Glu Pro His Val Gln Glu Ile Glu Val Ser Arg
                645                 650                 655
Leu Phe Leu Glu Pro Thr Arg Lys Asp Ile Ala Leu Leu Lys Leu Ser
            660                 665                 670
Ser Pro Ala Val Ile Thr Asp Lys Val Ile Pro Ala Cys Leu Pro Ser
        675                 680                 685
Pro Asn Tyr Val Val Ala Asp Arg Thr Glu Cys Phe Ile Thr Gly Trp
690                 695                 700
```

-continued

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
            725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 3
<211> LENGTH: 79
<212> TYPE: PRT
<213> ORGANISM: Homo sapiens

<400> SEQUENCE: 3

Cys Lys Thr Gly Asn Gly Lys Asn Tyr Arg Gly Thr Met Ser Lys Thr
1               5                   10                  15

Lys Asn Gly Ile Thr Cys Gln Lys Trp Ser Ser Thr Ser Pro His Arg
            20                  25                  30

Pro Arg Phe Ser Pro Ala Thr His Pro Ser Glu Gly Leu Glu Glu Asn
        35                  40                  45

Tyr Cys Arg Asn Pro Asp Asn Asp Pro Gln Gly Pro Trp Cys Tyr Thr
    50                  55                  60

Thr Asp Pro Glu Lys Arg Tyr Asp Tyr Cys Asp Ile Leu Glu Cys
65                  70                  75

<210> SEQ ID NO 4
<211> LENGTH: 78
<212> TYPE: PRT
<213> ORGANISM: Homo sapiens

<400> SEQUENCE: 4

Cys Met His Cys Ser Gly Glu Asn Tyr Asp Gly Lys Ile Ser Lys Thr
1               5                   10                  15

Met Ser Gly Leu Glu Cys Gln Ala Trp Asp Ser Gln Ser Pro His Ala
            20                  25                  30

His Gly Tyr Ile Pro Ser Lys Phe Pro Asn Lys Asn Leu Lys Lys Asn
        35                  40                  45

Tyr Cys Arg Asn Pro Asp Arg Glu Leu Arg Pro Trp Cys Phe Thr Thr
    50                  55                  60

Asp Pro Asn Lys Arg Trp Glu Leu Cys Asp Ile Pro Arg Cys
65                  70                  75

<210> SEQ ID NO 5
<211> LENGTH: 78
<212> TYPE: PRT
<213> ORGANISM: Homo sapiens

<400> SEQUENCE: 5

Cys Leu Lys Gly Thr Gly Glu Asn Tyr Arg Gly Asn Val Ala Val Thr
1               5                   10                  15

Val Ser Gly His Thr Cys Gln His Trp Ser Ala Gln Thr Pro His Thr

```
                    20                  25                  30
His Asn Arg Thr Pro Glu Asn Phe Pro Cys Lys Asn Leu Asp Glu Asn
                35                  40                  45
Tyr Cys Arg Asn Pro Asp Gly Lys Arg Ala Pro Trp Cys His Thr Thr
     50                  55                  60
Asn Ser Gln Val Arg Trp Glu Tyr Cys Lys Ile Pro Ser Cys
65                  70                  75

<210> SEQ ID NO 6
<211> LENGTH: 78
<212> TYPE: PRT
<213> ORGANISM: Homo sapiens

<400> SEQUENCE: 6

Cys Tyr His Gly Asp Gly Gln Ser Tyr Arg Gly Thr Ser Ser Thr Thr
1               5                   10                  15
Thr Thr Gly Lys Lys Cys Gln Ser Trp Ser Ser Met Thr Pro His Arg
                20                  25                  30
His Gln Lys Thr Pro Glu Asn Tyr Pro Asn Ala Gly Leu Thr Met Asn
                35                  40                  45
Tyr Cys Arg Asn Pro Asp Ala Asp Lys Gly Pro Trp Cys Phe Thr Thr
     50                  55                  60
Asp Pro Ser Val Arg Trp Glu Tyr Cys Asn Leu Lys Lys Cys
65                  70                  75

<210> SEQ ID NO 7
<211> LENGTH: 80
<212> TYPE: PRT
<213> ORGANISM: Homo sapiens

<400> SEQUENCE: 7

Cys Met Phe Gly Asn Gly Lys Gly Tyr Arg Gly Lys Arg Ala Thr Thr
1               5                   10                  15
Val Thr Gly Thr Pro Cys Gln Asp Trp Ala Ala Gln Glu Pro His Arg
                20                  25                  30
His Ser Ile Phe Thr Pro Glu Thr Asn Pro Arg Ala Gly Leu Glu Lys
                35                  40                  45
Asn Tyr Cys Arg Asn Pro Asp Gly Asp Val Gly Gly Pro Trp Cys Tyr
     50                  55                  60
Thr Thr Asn Pro Arg Lys Leu Tyr Asp Tyr Cys Asp Val Pro Gln Cys
65                  70                  75                  80
```